US010086012B2

(12) United States Patent
Deisseroth et al.

(10) Patent No.: US 10,086,012 B2
(45) Date of Patent: Oct. 2, 2018

(54) CONTROL AND CHARACTERIZATION OF MEMORY FUNCTION

(75) Inventors: Karl Deisseroth, Stanford, CA (US); Inbal Goshen, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 5 days.

(21) Appl. No.: 13/882,705

(22) PCT Filed: Nov. 4, 2011

(86) PCT No.: PCT/US2011/059283
§ 371 (c)(1),
(2), (4) Date: Jul. 25, 2013

(87) PCT Pub. No.: WO2012/061681
PCT Pub. Date: May 10, 2012

(65) Prior Publication Data
US 2013/0343998 A1 Dec. 26, 2013

Related U.S. Application Data

(60) Provisional application No. 61/540,926, filed on Sep. 29, 2011, provisional application No. 61/410,732, filed on Nov. 5, 2010.

(51) Int. Cl.
*A61K 48/00* (2006.01)
*C12N 15/86* (2006.01)
*A61K 31/7088* (2006.01)
*A61K 38/17* (2006.01)
*A01K 67/027* (2006.01)

(52) U.S. Cl.
CPC ...... *A61K 31/7088* (2013.01); *A01K 67/0275* (2013.01); *A61K 38/1709* (2013.01); *A01K 2217/052* (2013.01); *C07K 2319/04* (2013.01); *C07K 2319/10* (2013.01)

(58) Field of Classification Search
CPC ............... A61K 48/00; A61K 48/0008; A61K 48/0058; C12N 15/861; C12N 15/86
USPC ............... 514/44 R; 435/320.1, 456
See application file for complete search history.

(56) References Cited

U.S. PATENT DOCUMENTS

| 2,968,302 A | 1/1961 | Fry et al. |
| 3,131,690 A | 5/1964 | Innis et al. |
| 3,499,437 A | 3/1970 | Balamuth et al. |
| 3,567,847 A | 3/1971 | Price |
| 4,343,301 A | 8/1982 | Indech |
| 4,559,951 A | 12/1985 | Dahl et al. |
| 4,616,231 A | 10/1986 | Autrey et al. |
| 4,865,042 A | 9/1989 | Umemura et al. |
| 4,879,284 A | 11/1989 | Lang et al. |
| 5,032,123 A | 7/1991 | Katz et al. |
| 5,041,224 A | 8/1991 | Ohyama et al. |
| 5,082,670 A | 1/1992 | Gage et al. |
| 5,249,575 A | 10/1993 | Di Mino et al. |
| 5,267,152 A | 11/1993 | Yang et al. |
| 5,290,280 A | 3/1994 | Daikuzono et al. |
| 5,330,515 A | 7/1994 | Rutecki et al. |
| 5,382,516 A | 1/1995 | Bush |
| 5,411,540 A | 5/1995 | Edell et al. |
| 5,445,608 A | 8/1995 | Chen et al. |
| 5,460,950 A | 10/1995 | Barr et al. |
| 5,460,954 A | 10/1995 | Lee et al. |
| 5,470,307 A | 11/1995 | Lindall |
| 5,495,541 A | 2/1996 | Murray et al. |
| 5,520,188 A | 5/1996 | Hennige et al. |
| 5,527,695 A | 6/1996 | Hodges et al. |
| 5,550,316 A | 8/1996 | Mintz |
| 5,641,650 A | 6/1997 | Turner et al. |
| 5,703,985 A | 12/1997 | Owyang et al. |
| 5,722,426 A | 3/1998 | Kolff |
| 5,738,625 A | 4/1998 | Gluck |
| 5,739,273 A | 4/1998 | Engelman et al. |

(Continued)

FOREIGN PATENT DOCUMENTS

| CN | 1079464 A | 12/1993 |
| CN | 1558222 A | 12/2004 |

(Continued)

OTHER PUBLICATIONS

Wang et al. (2007) PNAS, vol. 104(19), 8143-8148.*
Gradinaru et al. (2008) Brain Cell Biology, vol. 36, 129-139.*
Lanyi et al. (1990) J. Biol. Chem., vol. 265(3), 1253-1260.*
Hofherr et al. (2005) Journal of Cell Science, vol. 118, 1935-1943.*
Samuelson, (20110 Dialogues Clin. Neurosci., vol. 13, 346-351.*
Brewin (2011) Annu. Rev. Clin. Psychol., vol. 7, 203-227, Table I.*
Xiong et al., "Interregional connectivity to primary motor cortex revealed using MRI resting state images", Hum Brain Mapp, 1999, 8(2-3):151-156.
Ageta-Ishihara et al., "Chronic overload of SEPT4, a parkin substrate that aggregates in Parkinson's disease, cause behavioral alterations but not neurodegeneration in mice", Molecular Brain, 2013, vol. 6, 14 pages.

(Continued)

Primary Examiner — Anne Marie S Wehbe
(74) Attorney, Agent, or Firm — Bozicevic, Field & Francis LLP; Paula A. Borden

(57) ABSTRACT

Provided herein are devices and methods for reversibly controlling memory function in living non-human animals. Some variations of methods for affecting memory function comprise temporarily inhibiting neurons of the hippocampus (e.g., neurons of the dorsal CA1 field of the hippocampus) during the acquisition or retrieval of a memory. Alternatively or additionally, methods for reversibly affecting memory function comprise inhibiting neurons of the amygdala (e.g. basolateral amygdala) and/or neurons of the cingulate cortex (e.g., anterior cingulated cortex). Methods for disrupting the formation and recall of memories by inhibiting excitatory neurons expressing light-activated proteins are disclosed herein. One or more methods for reversibly affecting memory function described herein can be used to evaluate the effectiveness of pharmacological agents in treating PTSD and/or various memory disorders.

9 Claims, 11 Drawing Sheets

Specification includes a Sequence Listing.

(56) References Cited

U.S. PATENT DOCUMENTS

| | | |
|---|---|---|
| 5,741,316 A | 4/1998 | Chen et al. |
| 5,755,750 A | 5/1998 | Petruska et al. |
| 5,756,351 A | 5/1998 | Isacoff et al. |
| 5,782,896 A | 7/1998 | Chen et al. |
| 5,795,581 A | 8/1998 | Segalman et al. |
| 5,807,285 A | 9/1998 | Vaitekunas et al. |
| 5,816,256 A | 10/1998 | Kissinger et al. |
| 5,836,941 A | 11/1998 | Yoshihara et al. |
| 5,898,058 A | 4/1999 | Nichols |
| 5,939,320 A | 8/1999 | Littman et al. |
| 6,056,738 A | 5/2000 | Marchitto et al. |
| 6,057,114 A | 5/2000 | Akong |
| 6,108,081 A | 8/2000 | Holtom et al. |
| 6,134,474 A | 10/2000 | Fischell et al. |
| 6,161,045 A | 12/2000 | Fischell et al. |
| 6,180,613 B1 | 1/2001 | Kaplitt et al. |
| 6,253,109 B1 | 6/2001 | Gielen |
| 6,303,362 B1 | 10/2001 | Kay et al. |
| 6,334,846 B1 | 1/2002 | Ishibashi et al. |
| 6,336,904 B1 | 1/2002 | Nikolchev |
| 6,346,101 B1 | 2/2002 | Alfano et al. |
| 6,364,831 B1 | 4/2002 | Crowley |
| 6,377,842 B1 | 4/2002 | Pogue et al. |
| 6,436,708 B1 | 8/2002 | Leone et al. |
| 6,473,639 B1 | 10/2002 | Fischell et al. |
| 6,480,743 B1 | 11/2002 | Kirkpatrick et al. |
| 6,489,115 B2 | 12/2002 | Lahue et al. |
| 6,497,872 B1 | 12/2002 | Weiss et al. |
| 6,506,154 B1 | 1/2003 | Ezion et al. |
| 6,536,440 B1 | 3/2003 | Dawson |
| 6,551,346 B2 | 4/2003 | Crossley |
| 6,567,690 B2 | 5/2003 | Giller et al. |
| 6,597,954 B1 | 7/2003 | Pless et al. |
| 6,609,020 B2 | 8/2003 | Gill |
| 6,615,080 B1 | 9/2003 | Unsworth et al. |
| 6,631,283 B2 | 10/2003 | Storrie et al. |
| 6,632,672 B2 | 10/2003 | Calos |
| 6,647,296 B2 | 11/2003 | Fischell et al. |
| 6,685,656 B1 | 2/2004 | Duarte et al. |
| 6,686,193 B2 | 2/2004 | Maher et al. |
| 6,721,603 B2 | 4/2004 | Zabara et al. |
| 6,729,337 B2 | 5/2004 | Dawson |
| 6,780,490 B1 | 8/2004 | Tanaka et al. |
| 6,790,652 B1 | 9/2004 | Terry et al. |
| 6,790,657 B1 | 9/2004 | Arya |
| 6,805,129 B1 | 10/2004 | Pless et al. |
| 6,808,873 B2 | 10/2004 | Murphy et al. |
| 6,810,285 B2 | 10/2004 | Pless et al. |
| 6,889,085 B2 | 5/2005 | Dawson |
| 6,918,872 B2 | 7/2005 | Yokoi |
| 6,921,413 B2 | 7/2005 | Mahadevan-Jansen et al. |
| 6,969,449 B2 | 11/2005 | Maher et al. |
| 6,974,448 B2 | 12/2005 | Petersen |
| 7,045,344 B2 | 5/2006 | Kay et al. |
| 7,091,500 B2 | 8/2006 | Schnitzer |
| 7,144,733 B2 | 12/2006 | Miesenbock et al. |
| 7,175,596 B2 | 2/2007 | Vitek et al. |
| 7,191,018 B2 | 3/2007 | Gielen et al. |
| 7,211,054 B1 | 5/2007 | Francis et al. |
| 7,220,240 B2 | 5/2007 | Struys et al. |
| 7,298,143 B2 | 11/2007 | Jaermann et al. |
| 7,313,442 B2 | 12/2007 | Velasco et al. |
| 7,603,174 B2 | 10/2009 | De Ridder |
| 7,610,100 B2 | 10/2009 | Jaax et al. |
| 7,613,520 B2 | 11/2009 | De Ridder |
| 7,686,839 B2 | 3/2010 | Parker |
| 7,824,869 B2 | 11/2010 | Hegemann et al. |
| 7,883,536 B1 | 2/2011 | Bendett |
| 7,988,688 B2 | 8/2011 | Webb et al. |
| 8,386,312 B2 | 2/2013 | Pradeep et al. |
| 8,398,692 B2 | 3/2013 | Deisseroth et al. |
| 8,401,609 B2 | 3/2013 | Deisseroth et al. |
| 8,696,722 B2 | 4/2014 | Deisseroth et al. |
| 8,815,582 B2 | 8/2014 | Deisseroth et al. |
| 8,906,360 B2 * | 12/2014 | Deisseroth et al. ......... 424/93.2 |
| 8,926,959 B2 | 1/2015 | Deisseroth et al. |
| 9,057,734 B2 | 6/2015 | Cohen |
| 9,079,940 B2 | 7/2015 | Deisseroth et al. |
| 9,175,095 B2 | 11/2015 | Deisseroth et al. |
| 9,458,208 B2 | 10/2016 | Deisseroth et al. |
| 9,522,288 B2 | 12/2016 | Deisseroth et al. |
| 9,604,073 B2 | 3/2017 | Deisseroth et al. |
| 2001/0023346 A1 | 9/2001 | Loeb |
| 2002/0094516 A1 | 7/2002 | Calos et al. |
| 2002/0155173 A1 | 10/2002 | Chopp et al. |
| 2002/0164577 A1 | 11/2002 | Tsien et al. |
| 2002/0190922 A1 | 12/2002 | Tsao |
| 2002/0193327 A1 | 12/2002 | Nemerow et al. |
| 2003/0009103 A1 | 1/2003 | Yuste et al. |
| 2003/0026784 A1 | 2/2003 | Koch et al. |
| 2003/0040080 A1 | 2/2003 | Miesenbock et al. |
| 2003/0050258 A1 | 3/2003 | Calos |
| 2003/0082809 A1 | 5/2003 | Quail et al. |
| 2003/0088060 A1 | 5/2003 | Benjamin et al. |
| 2003/0097122 A1 | 5/2003 | Ganz et al. |
| 2003/0103949 A1 | 6/2003 | Carpenter et al. |
| 2003/0104512 A1 | 6/2003 | Freeman et al. |
| 2003/0125719 A1 | 7/2003 | Furnish |
| 2003/0144650 A1 | 7/2003 | Smith |
| 2003/0204135 A1 | 10/2003 | Bystritsky |
| 2003/0232339 A1 | 12/2003 | Shu et al. |
| 2004/0013645 A1 | 1/2004 | Monahan et al. |
| 2004/0015211 A1 | 1/2004 | Nurmikko et al. |
| 2004/0023203 A1 | 2/2004 | Miesenbock et al. |
| 2004/0034882 A1 | 2/2004 | Vale et al. |
| 2004/0039312 A1 | 2/2004 | Hillstead et al. |
| 2004/0049134 A1 | 3/2004 | Tosaya et al. |
| 2004/0068202 A1 | 4/2004 | Hansson et al. |
| 2004/0073278 A1 | 4/2004 | Pachys |
| 2004/0076613 A1 | 4/2004 | Mazarkis; et al. |
| 2004/0122475 A1 | 6/2004 | Myrick et al. |
| 2004/0203152 A1 | 10/2004 | Calos |
| 2004/0216177 A1 | 10/2004 | Jordan et al. |
| 2004/0267118 A1 | 12/2004 | Dawson |
| 2005/0020945 A1 | 1/2005 | Tosaya et al. |
| 2005/0027284 A1 | 2/2005 | Lozano et al. |
| 2005/0058987 A1 | 3/2005 | Shi et al. |
| 2005/0088177 A1 | 4/2005 | Schreck et al. |
| 2005/0107753 A1 | 5/2005 | Rezai et al. |
| 2005/0112759 A1 | 5/2005 | Radisic et al. |
| 2005/0119315 A1 | 6/2005 | Fedida et al. |
| 2005/0124897 A1 | 6/2005 | Chopra |
| 2005/0143295 A1 | 6/2005 | Walker et al. |
| 2005/0143790 A1 | 6/2005 | Kipke et al. |
| 2005/0153885 A1 | 7/2005 | Yun et al. |
| 2005/0197679 A1 | 9/2005 | Dawson |
| 2005/0202398 A1 | 9/2005 | Hegemann et al. |
| 2005/0215764 A1 | 9/2005 | Tuszynski et al. |
| 2005/0240127 A1 | 10/2005 | Seip et al. |
| 2005/0267011 A1 | 12/2005 | Deisseroth et al. |
| 2005/0267454 A1 | 12/2005 | Hissong et al. |
| 2005/0279354 A1 | 12/2005 | Deutsch et al. |
| 2006/0025756 A1 | 2/2006 | Francischelli et al. |
| 2006/0034943 A1 | 2/2006 | Tuszynski |
| 2006/0057192 A1 | 3/2006 | Kane |
| 2006/0057614 A1 | 3/2006 | Heintz |
| 2006/0058671 A1 | 3/2006 | Vitek et al. |
| 2006/0058678 A1 | 3/2006 | Vitek et al. |
| 2006/0100679 A1 | 5/2006 | DiMauro et al. |
| 2006/0106543 A1 | 5/2006 | Deco et al. |
| 2006/0155348 A1 | 7/2006 | deCharms |
| 2006/0161227 A1 | 7/2006 | Walsh et al. |
| 2006/0167500 A1 | 7/2006 | Towe et al. |
| 2006/0179501 A1 | 8/2006 | Chan et al. |
| 2006/0184069 A1 | 8/2006 | Vaitekunas |
| 2006/0190044 A1 | 8/2006 | Libbus et al. |
| 2006/0206172 A1 | 9/2006 | DiMauro et al. |
| 2006/0216689 A1 | 9/2006 | Maher et al. |
| 2006/0236525 A1 | 10/2006 | Sliwa et al. |
| 2006/0241697 A1 | 10/2006 | Libbus et al. |
| 2006/0253177 A1 | 11/2006 | Taboada et al. |
| 2006/0271024 A1 | 11/2006 | Gertner et al. |
| 2007/0027443 A1 | 2/2007 | Rose et al. |
| 2007/0031924 A1 | 2/2007 | Li et al. |

(56) References Cited

U.S. PATENT DOCUMENTS

| | | |
|---|---|---|
| 2007/0054319 A1 | 3/2007 | Boyden et al. |
| 2007/0060915 A1 | 3/2007 | Kucklick |
| 2007/0060984 A1 | 3/2007 | Webb et al. |
| 2007/0135875 A1 | 6/2007 | Demarais et al. |
| 2007/0156180 A1 | 7/2007 | Jaax et al. |
| 2007/0191906 A1 | 8/2007 | Iyer et al. |
| 2007/0196838 A1 | 8/2007 | Chesnut et al. |
| 2007/0197918 A1 | 8/2007 | Vitek et al. |
| 2007/0219600 A1 | 9/2007 | Gertner et al. |
| 2007/0220628 A1 | 9/2007 | Glassman et al. |
| 2007/0239080 A1 | 10/2007 | Schaden et al. |
| 2007/0239210 A1 | 10/2007 | Libbus et al. |
| 2007/0253995 A1 | 11/2007 | Hildebrand |
| 2007/0260295 A1 | 11/2007 | Chen et al. |
| 2007/0261127 A1 | 11/2007 | Deisseroth et al. |
| 2007/0282404 A1 | 12/2007 | Cottrell et al. |
| 2007/0295978 A1 | 12/2007 | Coushaine et al. |
| 2008/0020465 A1 | 1/2008 | Padidam |
| 2008/0027505 A1 | 1/2008 | Levin et al. |
| 2008/0033569 A1 | 2/2008 | Ferren et al. |
| 2008/0046053 A1 | 2/2008 | Wagner et al. |
| 2008/0050770 A1 | 2/2008 | Zhang et al. |
| 2008/0051673 A1 | 2/2008 | Kong et al. |
| 2008/0060088 A1 | 3/2008 | Shin et al. |
| 2008/0065158 A1 | 3/2008 | Ben-Ezra et al. |
| 2008/0065183 A1 | 3/2008 | Whitehurst et al. |
| 2008/0077200 A1 | 3/2008 | Bendett et al. |
| 2008/0085265 A1 | 4/2008 | Deisseroth et al. |
| 2008/0088258 A1 | 4/2008 | Ng |
| 2008/0103551 A1 | 5/2008 | Masoud |
| 2008/0119421 A1 | 5/2008 | Tuszynski et al. |
| 2008/0125836 A1 | 5/2008 | Streeter et al. |
| 2008/0167261 A1 | 7/2008 | Sclimenti |
| 2008/0175819 A1 | 7/2008 | Kingsman et al. |
| 2008/0176076 A1 | 7/2008 | Van Veggel et al. |
| 2008/0200749 A1 | 8/2008 | Zheng et al. |
| 2008/0221452 A1 | 9/2008 | Njemanze |
| 2008/0227139 A1 | 9/2008 | Deisseroth et al. |
| 2008/0228244 A1 | 9/2008 | Pakhomov et al. |
| 2008/0262411 A1 | 10/2008 | Dobak |
| 2008/0287821 A1 | 11/2008 | Jung et al. |
| 2008/0290318 A1 | 11/2008 | Van Veggel et al. |
| 2009/0030930 A1 | 1/2009 | Pradeep et al. |
| 2009/0088680 A1 | 4/2009 | Deisseroth et al. |
| 2009/0093403 A1 | 4/2009 | Zhang et al. |
| 2009/0099038 A1 | 4/2009 | Deisseroth et al. |
| 2009/0112133 A1 | 4/2009 | Deisseroth et al. |
| 2009/0118800 A1 | 5/2009 | Deisseroth et al. |
| 2009/0148861 A1 | 6/2009 | Pegan et al. |
| 2009/0157145 A1 | 6/2009 | Cauller |
| 2009/0069261 A1 | 10/2009 | Dodge et al. |
| 2009/0131837 A1 | 10/2009 | Zhang et al. |
| 2009/0254134 A1 | 10/2009 | Nikolov et al. |
| 2009/0268511 A1 | 10/2009 | Birge et al. |
| 2009/0306474 A1 | 12/2009 | Wilson |
| 2009/0319008 A1 | 12/2009 | Mayer |
| 2009/0326603 A1 | 12/2009 | Boggs |
| 2010/0009444 A1 | 1/2010 | Herlitze et al. |
| 2010/0016783 A1 | 1/2010 | Bourke et al. |
| 2010/0021982 A1 | 1/2010 | Herlitze |
| 2010/0145418 A1 | 6/2010 | Zhang et al. |
| 2010/0146645 A1 | 6/2010 | Vasar et al. |
| 2010/0190229 A1 | 7/2010 | Deisseroth et al. |
| 2010/0209352 A1 | 8/2010 | Hultman et al. |
| 2010/0234273 A1 | 9/2010 | Deisseroth et al. |
| 2011/0021270 A1 | 1/2011 | Vo-Dinh et al. |
| 2011/0092800 A1 | 4/2011 | Yoo et al. |
| 2011/0105998 A1 | 5/2011 | Zhang et al. |
| 2011/0112179 A1 | 5/2011 | Deisseroth et al. |
| 2011/0112463 A1 | 5/2011 | Silver et al. |
| 2011/0125077 A1 | 5/2011 | Denison et al. |
| 2011/0125078 A1 | 5/2011 | Denison et al. |
| 2011/0159562 A1 | 6/2011 | Deisseroth et al. |
| 2011/0165681 A1 | 7/2011 | Boyden et al. |
| 2011/0166632 A1 | 7/2011 | Deisseroth et al. |
| 2011/0172653 A1 | 7/2011 | Deisseroth et al. |
| 2011/0233046 A1 | 9/2011 | Nikolenko et al. |
| 2011/0301529 A1 | 12/2011 | Deisseroth et al. |
| 2011/0311489 A1 | 12/2011 | Deisseroth et al. |
| 2012/0093772 A1 | 4/2012 | Horsager et al. |
| 2012/0121542 A1 | 5/2012 | Chuong et al. |
| 2012/0165904 A1 | 6/2012 | Deisseroth et al. |
| 2012/0253261 A1 | 10/2012 | Poletto et al. |
| 2013/0019325 A1 | 1/2013 | Deisseroth et al. |
| 2013/0030275 A1 | 1/2013 | Seymour et al. |
| 2013/0144359 A1 | 6/2013 | Kishawi et al. |
| 2013/0286181 A1 | 10/2013 | Betzig et al. |
| 2015/0112411 A1 | 4/2015 | Beckman et al. |

FOREIGN PATENT DOCUMENTS

| | | |
|---|---|---|
| CN | 102076866 A | 5/2011 |
| CN | 103313752 A | 9/2013 |
| CN | 103476456 A | 12/2013 |
| EP | 1197144 | 4/2002 |
| EP | 1 334 748 | 8/2003 |
| EP | 1444889 | 8/2004 |
| EP | 1873566 | 1/2008 |
| JP | 2006-295350 | 10/1994 |
| JP | H 09505771 A | 6/1997 |
| JP | 2004534508 | 11/2004 |
| JP | 2005034073 A | 2/2005 |
| JP | 2006217866 | 8/2006 |
| JP | 2007530027 A | 11/2007 |
| JP | 2008010422 A | 1/2008 |
| JP | 2010227537 A | 10/2010 |
| JP | 2012508581 | 4/2012 |
| WO | WO 1995/005214 | 2/1995 |
| WO | WO 1996/032076 | 10/1996 |
| WO | WO 2000/027293 | 5/2000 |
| WO | WO 2001-025466 | 4/2001 |
| WO | WO 03/106486 A2 | 2/2003 |
| WO | WO 2013/016486 | 2/2003 |
| WO | WO 2003-040323 | 5/2003 |
| WO | WO 2003/046141 | 6/2003 |
| WO | WO 2003-084994 | 10/2003 |
| WO | WO 2003-102156 | 12/2003 |
| WO | WO 2004/033647 | 4/2004 |
| WO | WO 2005/093429 | 10/2005 |
| WO | WO 2006/103678 | 10/2006 |
| WO | WO 2007-024391 | 3/2007 |
| WO | WO 2007-131180 | 11/2007 |
| WO | WO 2008/014382 | 1/2008 |
| WO | WO 2008/086470 | 7/2008 |
| WO | WO 2008/106694 | 9/2008 |
| WO | WO 2009/025819 | 2/2009 |
| WO | WO 2009/072123 | 6/2009 |
| WO | WO2009/119782 | 10/2009 |
| WO | WO 2009-131837 | 10/2009 |
| WO | WO 2009/148946 | 12/2009 |
| WO | WO 2010/006049 | 1/2010 |
| WO | WO 2010/011404 A3 | 1/2010 |
| WO | WO 2010/056970 | 5/2010 |
| WO | WO-2010123993 | 10/2010 |
| WO | WO 2011/005978 | 1/2011 |
| WO | WO 2011/066320 A3 | 6/2011 |
| WO | WO 2011/106783 | 9/2011 |
| WO | WO 2011-116238 A2 | 9/2011 |
| WO | WO 2011/127088 A3 | 10/2011 |
| WO | WO 2012/032103 | 3/2012 |
| WO | WO 2012/061676 | 5/2012 |
| WO | WO2012/061681 | 5/2012 |
| WO | WO2012/061684 | 5/2012 |
| WO | WO2012/061688 | 5/2012 |
| WO | WO2012/061690 | 5/2012 |
| WO | WO 2012/061741 | 5/2012 |
| WO | WO 2012/061744 | 5/2012 |
| WO | 2012/106407 | 8/2012 |
| WO | WO 2012/134704 A2 | 10/2012 |
| WO | WO 2013/003557 | 1/2013 |
| WO | WO 2013/090356 | 6/2013 |
| WO | WO 2013/126521 | 8/2013 |
| WO | WO 2013/126762 | 8/2013 |
| WO | WO 2013/142196 | 9/2013 |

(56) References Cited

FOREIGN PATENT DOCUMENTS

| WO | WO 2014/081449 | 5/2014 |
|---|---|---|
| WO | WO 2014/117079 | 7/2014 |
| WO | WO 2016/019075 | 2/2016 |

OTHER PUBLICATIONS

Axoclamp-28 Microelectrode claim theory and operation. Accessed from https://physics.ucsd.edu/neurophysics/Manuals/Axon%20Instruments/Axoclamp-2B_Manual.pdf on Dec. 12, 2014.
Cowan et al., "Targeting gene expression to endothelium in transgenic animals: a comparison of the human ICAM-2, PECAM-1, and endoglin promoters", Xenotransplantation, 2003, vol. 10, pp. 223-231.
Definition of Psychosis (2015).
Ebert et al., "A Moloney MLV-rat somatotropin fusion gene produces biologically active somatotropin in a transgenic pig", Mol. Endocrinology, 1988, vol. 2, pp. 277-283.
Hammer et al., "Spontaneous inflammatory disease in transgenic rats expressing HLA-B27 and Human $\beta_2$m: an animal model of HLA-B27-associated human disorders", Cell, 1990, vol. 63, pp. 1099-1112.
Karra, et al. "Transfection Techniques for Neuronal Cells", The Journal of Neuroscience, 2010, vol. 30, No. 18, pp. 6171-6177.
Kelder et al., "Glycoconjugates in human and transgenic animal milk", Advances in Exp. Med. and Biol., 2001, vol. 501, pp. 269-278.
Mullins et al., "Fulminant hypertension in transgenic rats harbouring the mouse Ren-2 gene", Nature, 1990, vol. 344, pp. 541-544.
Mullins et al., "Expression of the DBA/2J Ren-2 gene in the adrenal gland of transgenic mice", EMBO, 1989, vol. 8, pp. 4065-4072.
Taurog et al., "HLA-B27 in inbred and non-inbred transgenic mice", J. Immunol., 1988, vol. 141, pp. 4020-4023.
Wall, "Transgenic livestock: Progress and prospects for the future", Theriogenology, 1996, vol. 45, pp. 57-68.
Wang, et al., "High-speed mapping of synaptic connectivity using photostimulation in Channelrhodopsin-2 transgenic mice", Proceedings of the National Academy of Sciences, 2007, vol. 104, No. 19, pp. 8143-8148.
Written opinion of PCT Application No. PCT/US2011/059383 (dated May 9, 2012).
Shibasaki et al., "Effects of body temperature on neural activity in the hippocampus: Regulation of resting membrane potentials by transient receptor potential vanilloid 4," The Journal of Neuroscience, 2007, 27(7):1566-1575.
Takahashi, et al., "Induction of Pluripotent Stem Cells from Mouse Embryonic and Adult Fibroblast Cultures by Defined Factors", 2006, Cell, vol. 126, pp. 663-676.
Hikida et al., "Increased sensitivity to cocaine by cholinergic cell ablation in nucleus accumbens", PNAS, Nov. 2001, 98(23): 13351-13354.
Hikida et al., "Acetylcholine enhancement in the nucleus accumbens prevents addictive behaviors of cocaine and morphine", PNAS, May 2003, 100(10):6169-6173.
Kitabatake et al., "Impairment of reward-related learning by cholinergic cell ablation in the striatum", PNAS, Jun. 2003, 100(13):7965-7970.
Tamai, "Progress in Pathogenesis and Therapeutic Research in Retinitis Pigmentosa and Age Related Macular Degeneration", Nippon Ganka Gakkai Zasshi, vol. 108, No. 12, Dec. 2004 (Dec. 2004), pp. 750-769.
Fiala et al., "Optogenetic approaches in neuroscience", Current Biology, Oct. 2010, 20(20):R897-R903.
Gradinaru et al., "Optical deconstruction of parkinsonian neural circuitry", Science, Apr. 2009, 324(5925):354-359.
Liu et al., "Optogenetics 3.0", Cell, Apr. 2010, 141(1):22-24.
Malin et al., "Involvement of the rostral anterior cingulate cortex in consolidation of inhibitory avoidance memory: Interaction with the basolateral amygdala", Neurobiol Learning Mem, 2007, 87(2):295-302.
Mayford et al., "Control of memory formation through regulated expression of CAMKII Transgene", Science, Dec. 1996, 274:1678-1683.
Schroll et al., "Light-induced activation of distinct modulatory neurons triggers appetitive or aversive learning in *drosophila* larvae", Current Biology, Sep. 2006, 16(17):1741-1747.
Fox et al., "A gene neuron expression fingerprint of C. elegans embryonic motor neurons", BMC Genomics, 2005, 6(42):1-23.
Nonet, "Visualization of synaptic specializations in live C. elegans with synaptic vesicle protein-GFP fusions", J. Neurosci. Methods, 1999, 89:33-40.
Synapse, Chapter 13, http://michaeldmann.net/mann13.html, downloaded Apr. 2014.
Cazillis et al., "VIP and PACAP induce selective neuronal differentiation of mouse embryonic stem cells", Eur J Neurosci, 2004, 19(4):798-808.
Morelli et al., "Neuronal and glial cell type-specific promoters within adenovirus recombinants restrict the expression of the apoptosis-inducing molecule Fas ligand to predetermined brain cell types, and abolish peripheral liver toxicity", Journal of General Virology, 1999, 80:571-583.
Babin et al., "Zebrafish Models of Human Motor Neuron Diseases: Advantages and Limitations", Progress in Neurobiology (2014), 118:36-58.
Santana et al., "Can Zebrafish Be Used as Animal Model to Study Alzheimer's Disease?" Am. J. Neurodegener. Dis. (2012), 1(1):32-48.
Sheikh et al., "Neurodegenerative Diseases: Multifactorial Conformational Diseases and Their Therapeutic Interventions", Journal of Neurodegenerative Diseases (2013), Article ID 563481:1-8.
Suzuki et al., "Stable Transgene Expression from HSV Amplicon Vectors in the Brain: Potential Involvement of Immunoregulatory Signals", Molecular Therapy (2008), 16(10):1727-1736.
Thomas et al., "Progress and Problems with the Use of Viral Vectors for Gene", Nat. Rev. Genet. (2003), 4(5):346-358.
Berke, et al. "Addiction, Dopamine, and the Molecular Mechanisms of Memory", Molecular Plasticity, 2000, vol. 25: pp. 515-532.
Goshen et al. "Dynamics of Retrieval Strategies for Remote Memories", Cell, 2011, vol. 147: pp. 678-589.
Jimenez S.A & Maren S. et al/ "Nuclear disconnection within the amygdala reveals a direct pathway to fear", Learning Memory, 2009, vol. 16: pp. 766-768.
Ehrlich I. et al. "Amygdala inhibitory circuits and the control of fear memory", Neuron, 2009. Friedrich Meischer Institute, vol. 62: pp. 757-771.
Berndt et al. "Bi-stable neural state switches", Nature Neuroscience, 2009, vol. 12, No. 2: pp. 229-234.
Simmons et al. "Localization and function of NK3 subtype Tachykinin receptors of layer pyramidal neurons of the guinea-pig medial prefrontal cortex", Neuroscience, 2008, vol. 156, No. 4: pp. 987-994.
Davis; "The many faces of epidermal growth factor repeats," The New Biologist; vol. 2, No. 5, pp. 410-419 (1990).
De Palma, et al.; "In Vivo Targeting of Tumor Endothelial Cells by Systemic Delivery of Lentiviral Vectors"; Human Gene Therapy; vol. 14, pp. 1193-1206 (Aug. 10, 2003).
EBI accession No. UNIPROT: A7U0Y6; "SubName: Full= Bacteriorhodopsin"; (Aug. 10, 2010).
Ihara, et al.; "Evolution of the Archaeal Rhodopsins: Evolution Rate Changes by Gene Duplication and Functional Differentiation"; J. Mol. Biol.; vol. 285, pp. 163-174 (1999).
Kaiser; "Clinical research. Death prompts a review of gene therapy vector"; Science; 317(5838):580 (Aug. 3, 2007).
Kay; "State-of-the-art gene-based therapies: the road ahead"; Nature Reviews Genetics; vol. 12, pp. 316-328 (May 2011).
Singer; "Light Switch for Bladder Control"; Technology Review; pp. 1-2 (Sep. 14, 2009).
Skolnick, et al.; "From genes to protein structure and function: novel applications of computational approaches in the genomic era"; Trends Biotechnol; vol. 18, No. 1, pp. 34-39 (Jan. 2000).

(56) References Cited

OTHER PUBLICATIONS

Soofiyani, et al.; "Gene Therapy, Early Promises, Subsequent Problems, and Recent Breakthroughs"; Advanced Pharmaceutical Bulletin; vol. 3, No. 2, pp. 249-255 (2013).
U.S. Appl. No. 13/555,981, filed Jul. 23, 2012, Deisseroth, et al.
U.S. Appl. No. 13/622,809, filed Sep. 19, 2012, Deisseroth, et al.
U.S. Appl. No. 13/623,612, filed Sep. 20, 2012, Deisseroth, et al.
U.S. Appl. No. 13/718,243, filed Dec. 18, 2012, Deisseroth, et al.
U.S. Appl. No. 13/763,119, filed Feb. 8, 2013, Deisseroth, et al.
U.S. Appl. No. 13/763,132, filed Feb. 8, 2013, Deisseroth, et al.
U.S. Appl. No. 13/772,732, filed Feb. 21, 2013, Deisseroth, et al.
U.S. Appl. No. 13/847,653, filed Mar. 20, 2013, Deisseroth, et al.
U.S. Appl. No. 13/847,785, filed Mar. 20, 2013, Deisseroth, et al.
U.S. Appl. No. 13/849,913, filed Mar. 25, 2013, Deisseroth, et al.
U.S. Appl. No. 13/850,426, filed Mar. 26, 2013, Deisseroth, et al.
U.S. Appl. No. 13/850,428, filed Mar. 26, 2013, Deisseroth, et al.
U.S. Appl. No. 13/850,436, filed Mar. 26, 2013, Deisseroth, et al.
U.S. Appl. No. 13/850,709, filed Mar. 26, 2013, Deisseroth, et al.
U.S. Appl. No. 13/854,750, filed Apr. 1, 2013, Deisseroth, et al.
U.S. Appl. No. 13/854,754, filed Apr. 1, 2013, Deisseroth, et al.
U.S. Appl. No. 13/855,413, filed Apr. 2, 2013, Deisseroth, et al.
U.S. Appl. No. 13/875,966, filed May 2, 2013, Deisseroth, et al.
U.S. Appl. No. 13/882,566, filed Nov. 4, 2011, Deisseroth, et al.
U.S. Appl. No. 13/882,666, filed Nov. 4, 2011, Deisseroth, et al.
U.S. Appl. No. 13/882,670, filed Nov. 4, 2011, Deisseroth, et al.
U.S. Appl. No. 13/882,703, filed Nov. 4, 2011, Deisseroth, et al.
U.S. Appl. No. 13/882,719, filed Nov. 4, 2011, Deisseroth, et al.
Tam, B. et al., "Identification of an Outer Segment Targeting Signal in the COOH Terminus of Rhodopsin Using Transgenic Xenopus laevis", The Journal of Cell Biology, 2000, vol. 151, No. 7, pp. 1369-1380.
U.S. Appl. No. 11/459,636, filed Jul. 24, 2006, published as US 2007-0261127.
U.S. Appl. No. 11/459,638, filed Jul. 24, 2006, published as US 2007-0054319.
U.S. Appl. No. 11/651,422, filed Jan. 9, 2007, published as US 2008-0085265.
U.S. Appl. No. 12/031,651, filed Feb. 14, 2008, issued as U.S. Pat. No. 8,401,609 on Mar. 19, 2013.
U.S. Appl. No. 12/185,624, filed Aug. 4, 2008, published as US 2009-0088680.
U.S. Appl. No. 12/187,927, filed Aug. 7, 2008, published as US 2009-0099038.
U.S. Appl. No. 12/263,026, filed Oct. 31, 2008, published as US 2009-0112133.
U.S. Appl. No. 12/263,044, filed Oct. 31, 2008, published as US 2009-0118800.
U.S. Appl. No. 12/522,520, filed Jan. 8, 2010, issued as U.S. Pat No. 8,398,692 on Mar. 19, 2013.
U.S. Appl. No. 12/522,528, filed Apr. 6, 2010, published as US 2010-0190229.
U.S. Appl. No. 12/715,259, filed Mar. 1, 2010, published as US 2010-0234273.
U.S. Appl. No. 12/988,567, filed Dec. 7, 2010, published as US 2011-0105998.
U.S. Appl. No. 12/993,605, filed Jan. 20, 2011, published as US 2011-0112179.
U.S. Appl. No. 12/996,753, filed Mar. 10, 2011, published as US 2011-0166632.
U.S. Appl. No. 12/997,140, filed Feb. 7, 2011, published as US 2011-0159562.
U.S. Appl. No. 12/997,158, filed Feb. 7, 2011, published as US 2011-0172653.
U.S. Appl. No. 13/128,979, filed Jul. 28, 2011, published as US 2011-0311489.
U.S. Appl. No. 13/208,419, filed Aug. 12, 2011, published as US 2011-0301529.
U.S. Appl. No. 13/299,727, filed Nov. 18, 2011, published as US 2012-0165904.
U.S. Appl. No. 13/555,981, filed Jul. 23, 2013.
U.S. Appl. No. 13/577,565, filed Sep. 14, 2012, published as US 2013-0019325.
U.S. Appl. No. 13/622,809, filed Sep. 18, 2012.
U.S. Appl. No. 13/623,612, filed Sep. 20, 2013.
U.S. Appl. No. 13/718,243, filed Dec. 18, 2012.
U.S. Appl. No. 13/763,119, filed Feb. 8, 2013.
U.S. Appl. No. 13/763,132, filed Feb. 8, 2013.
U.S. Appl. No. 13/772,732, filed Feb. 21, 2013.
U.S. Appl. No. 13/847,653, filed Mar. 20, 2013.
U.S. Appl. No. 13/847,785, filed Mar. 20, 2013.
U.S. Appl. No. 13/849,913, filed Mar. 25, 2013.
U.S. Appl. No. 13/850,426, filed Mar. 26, 2013.
U.S. Appl. No. 13/850,428, filed Mar. 26, 2013.
U.S. Appl. No. 13/850,436, filed Mar. 26, 2013.
U.S. Appl. No. 13/850,709, filed Mar. 26, 2013.
U.S. Appl. No. 13/854,750, filed Apr. 1, 2013.
U.S. Appl. No. 13/854,754, filed Apr. 1, 2013.
U.S. Appl. No. 13/855,413, filed Apr. 2, 2013.
U.S. Appl. No. 13/882,566, filed Nov. 4, 2011.
U.S. Appl. No. 13/882,666, filed Nov. 4, 2011.
U.S. Appl. No. 13/882,670, filed Nov. 4, 2011.
U.S. Appl. No. 13/822,703, filed Nov. 4, 2011.
U.S. Appl. No. 13/875,966, filed May 2, 2013.
U.S. Appl. No. 13/882,719, filed Nov. 4, 2011.
Adamantidis, et al., "Optogenetic Interrogation of Dopaminergic Modulation of the Multiple Phases of Reward-Seeking Behavior", J. Neurosci, 2011, vol. 31, No. 30, pp. 10829-10835.
Han, et al., "Multiple-Color Optical Activation, Silencing, and Desynchronization of Neural Activity with Single-Spike Temporal Resolution", PLoS One, 2007, vol. 2, No. 3, pp. 1-12.
Kinoshita, et al., "Optogenetically Induced Supression of Neural Activity in the Macaque Motor Cortex", Poster Sessions Somatomotor System, Others,2010, pp. 141-154.
Rein, et al., "The Optogenetic (r)evolution", Mol. Genet. Genomics, 2012, vol. 287, No. 2, pp. 95-109.
Remy, et al., "Depression in Parkinson's Disease: Loss of Dopamine and Noradrenaline Innervation in the Limbic System", Brain, 2005, vol. 128 (Pt 6), pp. 1314-1322.
Tsai, et al., "Phasic Firing in Dopaminergic Neurons in Sufficient for Behavioral Conditioning", Science, 2009, vol. 324, pp. 1080-1084.
Zhao, et al., "Improved Expression of Halorhodopsin for Light-Induced Silencing of Neuronal Activity", Brain Cell Biology, 2008, vol. 36 (1-4), pp. 141-154.
Lanyi et al. "The primary structure of a Halorhodopsin from *Natronobacterium Pharaonis*" Journal of Biological Chemistry 1990, vol. 265, No. 3, p. 1253-1260.
Hofherr et al. "Selective Golgi export of Kir2.1 controls the stoichiometry of functional Kr2.x channel heteromers" Journal of Cell Science, 2005, vol. 118, p. 1935-1943.
Loetterle, et al., "Cerebellar Stimulation: Pacing the Brain", American Journal of Nursing, 1975, vol. 75, No. 6, pp. 958-960.
Balint, et al., "The Nitrate Transporting Photochemical Reaction Cycle of the Pharaonis Halorhodopsin", Biophysical Journal, 2004, vol. 86, pp. 1655-1663.
Gradinaru, et al., Molecular and Cellular Approaches for Diversifying and Extending Optogenetics, Cell, 2010, vol. 141, No. 1, pp. 154-165.
RecName: Full=Halorhodopsin; Short=HR; Alt Name: Full=NpHR; XP002704922, retrieved from EBI accession No. UNIPROT: P15647. Database accession No. P15647. Apr. 1, 1990.
"*N. pharaonis halorhodopsin* (hop) gene, complete cds.", XP002704883, retrieved from EBI accession No. EMBL: J05199. Database accession No. J05199. Nov. 22, 1990.
"Subname: Fluu=Bacteriorhodopsin"; XP002704863, retrieved from EBI accession No. UNIPROT: B0R5N9. Database accession No. B0R5N9. Apr. 8, 2008.
Zhang, et al., "The Microbial Opsin Family of Optogenetic Tools", Cell, 2011, vol. 147, No. 7, pp. 1146-1457.
Gradinaru et al., "Targeting and readout strategies for fast optical neural control in vitro and in vivo", J Neuroscience, 2007, 27(52):14231-14238.

(56) References Cited

OTHER PUBLICATIONS

Wang, et al., "Molecular Determinants Differentiating Photocurrent Properties of Two Channelrhodopsins from Chlamydomonas", 2009, The Journal of Biological Chemistry, vol. 284, No. 9, pp. 5685-5696.

Delaney et al., "Evidence for a long-lived 13-cis-containing intermediate in the photocycle of the leu 93 → ala bacteriorhodopsin mutant", J. Physical Chemistry B, 1997, vol. 101, No. 29, pp. 5619-5621.

Fenno et al., "The development and application of optogenetics", Annual Review of Neuroscience, 2011, vol. 34, No. 1, pp. 389-412.

Gunaydin et al., "Ultrafast optogenetic control", Nature Neuroscience, 2010, vol. 13, No. 3, pp. 387-392.

Hira et al., "Transcranial optogenetic stimulation for functional mapping of the motor cortex", J Neurosci Methods, 2009, vol. 179, pp. 258-263.

Lalumiere, R., "A new technique for controlling the brain: optogenetics and its potential for use in research and the clinic", Brain Stimulation, 2011, vol. 4, pp. 1-6.

Lin, "A users guide to channelrhodopsin variants: features, limitations and future developments", Exp Physiol, 2010, vol. 96, No. 1, pp. 19-25.

Mancuso et al., "Optogenetic probing of functional brain circuitry", Experimental Physiology, 2010, vol. 96.1, pp. 26-33.

Peralvarez-Marin et al., "Inter-helical hydrogen bonds are essential elements for intra-protein signal transduction: The role of Asp115 in bacteriorhodopsin transport function", J. Mol. Biol., 2007, vol. 368, pp. 666-676.

Pinkham et al., "Neural bases for impaired social cognition in schizophrenia and autism spectrum disorders", Schizophrenia Research, 2008, vol. 99, pp. 164-175.

Sohal et al., "Parvalbumin neurons and gamma rhythms enhance cortical circuit performance", Nature, 2009, vol. 459, No. 7247, pp. 698-702.

Yizhar et al., "Optogenetics in neural systems", Neuron Primer, 2011, vol. 71, No. 1, pp. 9-34.

Li et al., "Surface Expression of Kv1 Channels is Governed by a C-Terminal Motif", J. Biol. Chem. (2000), 275(16):11597-11602.

Lonnerberg et al. "Regulatory Region in Choline Acetyltransferase Gene Directs Developmental and Tissue-Specific Expression in Transgenic mice", Proc. Natl. Acad. Sci. USA (1995), 92(9):4046-4050.

Varo et al.,"Light-Driven Chloride Ion Transport by Halorhodopsin from Natronobacterium pharaonis. 2. Chloride Release and Uptake, Protein Conformation Change, and Thermodynamics", Biochemistry (1995), 34(44):14500-14507.

Deisseroth, et al., "Controlling the Brain with Light", Scientific American, 2010, vol. 303, pp. 48-55.

Douglass, et al., "Escape Behavior Elicited by Single, Channelrhodopsin-2-evoked Spikes in Zebrafish Somatosensory Neurons", Curr Biol., 2008, vol. 18, No. 15, pp. 1133-1137.

Sineshchekov, et al., "Two Rhodopsins Mediate Phototaxis to Low and High Intensity Light in Chlamydomas Reinhardtil", PNAS, 2002, vol. 99, No. 13, pp. 8689-8694.

Tønnese, et al., "Optogenetic Control of Epileptiform Activity", PNAS, 2009, vol. 106, No. 29, pp. 12162-12167.

Berndt et al., "Structure-Guided Transformation of Channelrhodopsin into a Light-Activated Chloride Channel", Science (Apr. 2014), 344(6182):420-424.

Chow et al., "Optogenetics and Translational Medicine", Science Translational Medicine (Mar. 2013), 5(177):177ps5.

Eijkelkamp, et al. "Neurological perspectives on voltage-gated sodium channels", Brain (Sep. 2012), 135(Pt 9):2585-2612.

Garrido et al., "A targeting motif involved in sodium channel clustering at the axonal initial segment", Science (Jun. 2003), 300(5628):2091-4.

Han; et al., "Two-color, bi-directional optical voltage control of genetically-targeted neurons", CoSyne (2007), Abstract Presentation, Poster III-67, p. 269, Presented Feb. 24, 2007.

Hustler; et al., "Acetylcholinesterase staining in human auditory and language cortices: regional variation of structural features", Cereb Cortex (Mar.-Apr. 1996), 6(2):260-70.

Iyer et al., "Virally mediated optogenetic excitation and inhibition of pain in freely moving nontransgenic mice", Nat Biotechnol., (Mar. 2014), 32(3):274-8.

Ji et al., "Light-evoked Somatosensory Perception of Transgenic Rats that Express Channelrhodopsin-2 in Dorsal Root Ganglion Cells", PLoS One (2012), 7(3):e32699.

Jennings et al., "Distinct extended amygdala circuits for divergent motivational states," Nature (Apr. 2013), 496 (7444):224-8.

Kim et al., "PDZ domain proteins of synapses", Nature Reviews Neuroscience, (Oct. 2004), 5(10):771-81.

Kim et al., "Diverging neural pathways assemble a behavioural state from separable features in anxiety" Nature (Apr. 2013), 496(7444):219-23.

Kokel et al., "Photochemical activation of TRPA1 channels in neurons and animals", Nat Chem Biol (Apr. 2013), 9(4):257-63.

Lammel et al., "Input-specific control of reward and aversion in the ventral tegmental area", Nature (Nov. 2012), 491 (7423): 212-7.

Liske et al., "Optical inhibition of motor nerve and muscle activity in vivo", Muscle Nerve (Jun. 2013), 47(6):916-21.

Llewellyn et al., "Orderly recruitment of motor units under optical control in vivo", Nature Medicine, (Oct. 2010), 16 (10):1161-5.

Mattis et al., "Principles for applying optogenetic tools derived from direct comparative analysis of microbial opsins", Nat Methods (Dec. 2011), 9(2):159-72.

Mourot et al., "Rapid Optical Control of Nociception with an Ion Channel Photoswitch", Nat Methods (Feb. 2012), 9 (4):396-402.

Nieh et al., "Optogenetic dissection of neural circuits underlying emotional valence and motivated behaviors", Brain Research, (May 2012), 1511:73-92.

Slamovits et al., "A bacterial proteorhodopsin proton pump in marie eukaryotes", Nature Communications (Feb. 2011), 2:183.

Towne et al., "Efficient transduction of non-human primate motor neurons after intramuscular delivery of recombinant AAV serotype 6", Gene Ther. (Jan. 2010), 17(1):141-6.

Towne et al., "Optogenetic control of targeted peripheral axons in freely moving animals", PLoS One (Aug. 2013), 8(8):e72691.

Towne et al., "Recombinant adeno-associated virus serotype 6 (rAAV2/6)-mediated gene transfer to nociceptive neurons through different routes of delivery", Mol Pain (Sep. 2009), 5:52.

Wang et al., "Mrgprd-Expressing Polymodal Nociceptive Neurons Innervate Most Known Classes of Substantia Gelatinosa Neurons", J Neurosci (Oct. 2009), 29(42):13202-13209.

Williams et al., "From optogenetic technologies to neuromodulation therapies", Sci Transl Med. (Mar. 2013), 5 (177):177ps6.

Arenkiel, et al. "In vivo light-induced activation of neural circuitry in transgenic mice expressing Channelrhodopsin-2", Neuron, 2007, 54:205-218.

Milella et al. "Opposite roles of dopamine and orexin in quinpirole-induced excessive drinking: a rat model of psychotic polydipsia" Psychopharmacology, 2010, 211:355-366.

Marin, et al., The Amino Terminus of the Fourth Cytoplasmic Loop of Rhodopsin Modulates Rhodopsin-Transduction Interaction, The Journal of Biological Chemistry, 2000, vol. 275, pp. 1930-1936.

Aebischer, et al. "Long-Term Cross-Species Brain Transplantation of a Polymer-Encapsulated Dopamine-Secreting Cell Line", Experimental Neurology, 1991, vol. 111, pp. 269-275.

Ahmad, et al. "The Drosophila rhodopsin cytoplasmic tail domain is required for maintenance of rhabdomere structure." The FASEB Journal, 2007, vol. 21, p. 449-455.

Airan, et al., "Temporally Precise in vivo Control of Intracellular Signaling", 2009, Nature, vol. 458, No. 7241, pp. 1025-1029.

Akirav, et al. "The role of the medial prefrontal cortex-amygdala circuit in stress effects on the extinction of fear", Neural Plasticity, 2007: vol. 2007 Article ID:30873, pp. 1-11.

Ang, et at. "Hippocampal CA1 Circuitry Dynamically Gates Direct Cortical Inputs Preferentially at Theta Frequencies." The Journal of Neurosurgery, 2005, vol. 25, No. 42, pp. 9567-9580.

Araki, et al. "Site-Directed Integration of the cre Gene Mediated by Cre Recombinase Using a Combination of Mutant lox Sites", Nucleic Acids Research, 2002, vol. 30, No. 19, pp. 1-8.

(56) References Cited

OTHER PUBLICATIONS

Aravanis, et al. "An optical neural interface: in vivo control of rodent motor cortex with integrated fiberoptic and optogenetic technology," J. Neural. Eng., 2007, vol. 4(3):S143-S156.
Argos, et al. "The integrase family of site-specific recombinases: regional similarities and global diversity", The EMBO Journal, 1986, vol. 5, No. 2, pp. 433-440.
Bamberg et al. "Light-driven proton or chloride pumping by halorhodopsin." Proc. Natl. Academy Science USA, 1993, vol. 90, No. 2, p. 639-643.
Banghart, et al. "Light-activated ion channels for remote control of neuronal firing". Nature Neuroscience, 2004, vol. 7, No. 12 pp. 1381-1386.
Basil et al. "Is There Evidence for Effectiveness of Transcranial Magnetic Stimulation in the Treatment of Psychiatric Disorders?" Psychiatry, 2005, pp. 64-69.
Bebbington et al., The use of vectors based on gene amplification for the expression of cloned genes in mammalian cells in "DNA cloning" vol. 3, Academic Press, New York, 1987.
Benabid "Future strategies to restore brain functions," Conference proceedings from Medicine Meets Millennium: World Congress of Medicine and Health, 2000, 6 pages.
Benoist et al. "In vivo sequence requirements of the SV40 early promotor region" Nature (London), 1981, vol. 290(5804): pp. 304-310.
Berges et al., "Transduction of Brain by Herpes Simplex Virus Vectors", Molecular Therapy, 2007, vol. 15, No. 1: pp. 20-29.
Berridge et al., "The Versatility and Universality of Calcium Signaling", Nature Reviews: Molecular Cell Biology, 2000, vol. 1: pp. 11-21.
Bocquet et al. "A prokaryotic proton-gated ion channel from the nicotinic acetylcholine receptor family." Nature Letters, 2007, vol. 445, p. 116-119.
Boyden, et al. "Millisecond-timescale, genetically targeted optical control of neural activity" Nature Neuroscience, 2005, vol. 8, No. 9: pp. 1263-1268.
Bi, et al. "Ectopic Expression of a Microbial-Type Rhodopsin Restores Visual Responses in Mice with Photoreceptor Degeneration", Neuron, 2006, vol. 50, No. 1: pp. 23-33.
Bi, et al. "Synaptic Modifications in Cultured Hippocampal Neurons: Dependence on Spike Timing, Synaptic Strength, and Postsynaptic Cell Type", Journal of Neuroscience, 1998, vol. 18, No. 24: pp. 10464-1 0472.
Blomer et al., "Highly Efficient and Sustained Gene Transfer in Adult Neurons with Lentivirus Vector", Journal of Virology,1997, vol. 71, No. 9: pp. 6641-6649.
Braun, "Two Light-activated Conductances in the Eye of the Green Alga *Volvox carteri*", 1999, Biophys J., vol. 76, No. 3, pp. 1668-1678.
Brinton, et al. "Preclinical analyses of the therapeutic potential of allopregnanolone to promote neurogenesis in vitro and in vivo in transgenic mouse model of Alzheimer's disease." Current Alzheimer Research, 2006, vol. 3, No. 1: pp. 11-17.
Brosenitsch et al, "Physiological Patterns of Electrical Stimulation Can Induce Neuronal Gene Expression by Activating N-Type Calcium Channels," Journal of Neuroscience, 2001, vol. 21, No. 8, pp. 2571-2579.
Brown, et al. "Long-term potentiation induced by θ frequency stimulation is regulated by a protein phosphate-operated gate." The Journal of Neuroscience, 2000, vol. 20, No. 21, pp. 7880-7887.
Callaway, et al. "Photostimulation using caged glutamate reveals functional circuitry in living brain slices", Proc. Natl. Acad. Sci. USA., 1993, vol. 90: pp. 7661-7665.
Campagnola et al. "Fiber-coupled light-emitting diode for localized photostimulation of neurons expressing channelrhodopsin-2." Journal of Neuroscience Methods , 2008, vol. 169, Issue 1. Abstract only.
Cardin, et al. "Driving Fast spiking Cells Induces Gamma Rhythm and Controls Sensory Responses", 2009, Nature, vol. 459, vol. 7247, pp. 663-667.
Cenatiempo "Prokaryotic gene expression in vitro: transcription-translation coupled systems", Biochimie, 1986, vol. 68(4): pp. 505-515.
Claudio et al. "Nucleotide and deduced amino acid sequences of Torpedo californica acetylcholine receptor gamma subunit." PNAS USA,1983, vol. 80, p. 1111-1115.
Collingridge et al. "Inhibitory post-synaptic currents in rat hippocampal CA1 neurones." J. Physiol., 1984, vol. 356, pp. 551-564.
Covington, et al. "Antidepressant Effect of Optogenetic Stimulation of the Medial Prefrontal Cortex." Journal of Neuroscience, 2010, vol. 30(48), pp. 16082-16090.
Crouse, et al. "Expression and amplification of engineered mouse dihydrofolate reductase minigenes" Mol. Cell. Biol. , 1983, vol. 3(2): pp. 257-266.
Cucchiaro et al., "Phaseolus vulgaris leucoagglutinin (PHA-L): a neuroanatomical tracer for electron microscopic analysis of synaptic circuitry in the cat's dorsal lateral geniculate nucleus" J. Electron. Microsc. Tech., 1990, 15 (4):352-368.
Cucchiaro et al., "Electron-Microsoft Analysis of Synaptic Input from the Perigeniculate Nucleus to A-Lamine of the Lateral Geniculate Nucleus in Cats", The Journal of Comparitive Neurology, 1991, vol. 310, pp. 316-336.
Cui, et al., "Electrochemical deposition and characterization of conducting polymer polypyrrole/PSS on multichannel neural probes," Sensors and Actuators, 2001, vol. 93(1): pp. 8-18.
Date, et al. "Grafting of Encapsulated Dopamine-Secreting Cells in Parkinson's Disease: Long-Term Primate Study", Cell Transplant, 2000, vol. 9, pp. 705-709.
Dalva, et al. "Rearrangements of Synaptic Connections in Visual Cortex Revealed by Laser Photostimulation", Science, 1994,vol. 265, pp. 255-258.
Dederen, et al. "Retrograde neuronal tracing with cholera toxin B subunit: comparison of three different visualization methods", Histochemical Journal, 1994, vol. 26, pp. 856-862.
De Foubert et al. "Fluoxetine-Induced Change in Rat Brain Expression of Brain-Derived Neurotrophic Factor Varies Depending on Length of Treatment," Neuroscience, 2004, vol. 128, pp. 597-604.
Deisseroth et al., "Signaling from Synapse to Nucleus: Postsynaptic CREB Phosphorylation During Multiple Forms of Hippocampal Synaptic Plasticity", Neuron, 1996, vol. 16, pp. 89-101.
Deisseroth et al., "Translocation of Calmodulin to the Nucleus Supports CREB Phosphorylation in Hippocampal Neurons", Nature, 1998, vol. 392, pp. 198-202.
Deisseroth et al., "Signaling from Synapse to Nucleus: the logic Behind the Mechanisms", Currrent Opinion in Neurobiology, 2003, vol. 13, pp. 354-65.
Deisseroth et al., "Excitation-neurogenesis Coupling in Adult Neural Stem/Progenitor Cells", 2004, Neuron, vol. 42, pp. 535-552.
Deisseroth "Next-generation optical technologies for illuminating genetically targeted brain circuits," The Journal of Neuroscience, 2006, vol. 26, No. 41, pp. 10380-10386.
Denk, W., et al. "Anatomical and functional imaging of neurons using 2-photon laser scanning microscopy", Journal of Neuroscience Methods, 1994, vol. 54, pp. 151-162.
Ditterich, et al. "Microstimulation of visual cortex affects the speed of perceptual decisions", 2003, Nature Neuroscience, vol. 6, No. 8, pp. 891-898.
Dittgen, et al. "Lentivirus-based genetic manipulations of cortical neurons and their optical and electrophysiological monitoring in vivo", PNAS, 2004, vol. 101, No. 52, pp. 18206-18211.
Emerich, et al. "A Novel Approach to Neural Transplantation in Parkinson's Disease: Use of Polymer-Encapsulated Cell Therapy", Neuroscience and Biobehavioral Reviews, 1992, vol. 16, pp. 437-447.
Ensell, et al. "Silicon-based microelectrodes for neurophysiology, micromachined from silicon-on-insulator wafers," Med. Biol. Eng. Comput., 2000, vol. 38, pp. 175-179.
Eisen, "Treatment of amyotrophic lateral sclerosis", Drugs Aging, 1999; vol. 14, No. 3, pp. 173-96.
Ernst, et al. "Photoactivation of Channelrhodopsin", 2008, vol. 283, No. 3, pp. 1637-1643.
Evanko "Optical excitation yin and yang" Nature Methods, 2007, 4:384.

(56) References Cited

OTHER PUBLICATIONS

Esposito et al. "The integrase family of tyrosine recombinases: evolution of a conserved active site domain", Nucleic Acids Research, 1997, vol. 25, No. 18, pp. 3605-3614.
Fabian et al. "Transneuronal transport of lectins" Brain Research, 1985, vol. 344, pp. 41-48.
Falconer et al. "High-throughput screening for ion channel modulators," Journal of Biomolecular Screening, 2002, vol. 7, No. 5, pp. 460-465.
Farber, et al. "Identification of Presynaptic Neurons by Laser Photostimulation", Science, 1983, vol. 222, pp. 1025-1027.
Feng, et al. "Imaging Neuronal Subsets in Transgenic Mice Expressing Multiple Spectral Variants of GFP", Neuron, 2000, vol. 28, pp. 41-51.
Fisher, J. et al. "Spatiotemporal Activity Patterns During Respiratory Rhythmogenesis in the Rat Ventrolateral Medulla," The Journal of Neurophysiol, 2006, vol. 95, pp. 1982-1991.
Fitzsimons et al., "Promotors and Regulatory Elements that Improve Adeno-Associated Virus Transgene Expression in the Brain", 2002, Methods, vol. 28, pp. 227-236.
Foster, "Bright blue times," Nature, 2005, vol. 433, pp. 698-699.
Genbank Accession No. DQ094781 (Jan. 15, 2008).
Gelvich et al. "Contact flexible microstrip applicators (CFMA) in a range from microwaves up to short waves," IEEE Transactions on Biomedical Engineering, 2002, vol. 49, Issue 9: 1015-1023.
Gigg, et al. "Glutamatergic hippocampal formation projections to prefrontal cortex in the rat are regulated by GABAergic inhibition and show convergence with glutamatergic projections from the limbic thalamus," Hippocampus, 1994, vol. 4, No. 2, pp. 189-198.
Gilman, et al. "Isolation of sigma-28-specific promoters from *Bacillus subtilis* DNA" Gene, 1984, vol. 32(1-2): pp. 11-20.
Glick et al. "Factors affecting the expression of foreign proteins in *Escherichia coli*", Journal of Industrial Microbiology, 1987, vol. 1(5): pp. 277-282.
Goekoop, R. et al. "Cholinergic challenge in Alzheimer patients and mild cognitive impairment differentially affects hippocampal activation—a pharmacological fMRI study." Brain, 2006, vol. 129, pp. 141-157.
Gold, et al. "Representation of a perceptual decision in developing oculomotor commands", Nature, 2000, vol. 404, pp. 390-394.
Gonzalez, et al., "Cell-Based Assays and Instrumentation for Screening Ion-Channel Targets", DDT, 1999, vol. 4, No. 9, pp. 431439.
Gordon, et al. "Regulation of Thy-1 Gene Expression in Transgenic Mice", Cell, 1987, vol. 50, pp. 445-452.
Gorelova et al., "The course of neural projection from the prefrontal cortex to the nucleus accumbens in the rat", Neuroscience, 1997, vol. 76, No. 3, pp. 689-706.
Gottesman et al."Bacterial regulation: global regulatory networks," Ann. Rev. Genet. , 1984, vol. 18, pp. 415-441.
Gradinaru, et al. "ENpHR: a Natronomonas Halorhodopsin Enhanced for Optogenetic Applications", 2008, Brain Cell Biol., vol. 36 (1-4), pp. 129-139.
Greenberg, et al. "Three-year outcomes in deep brain stimulation for highly resistant obsessive-compulsive disorder," Neuropsychopharmacology, 2006, vol. 31, pp. 2384-2393.
Gregory, et al. "Integration site for *Streptomyces* phage φBT1 and development of site-specific integrating vectors", Journal of Bacteriology, 2003, vol. 185, No. 17, pp. 5320-5323.
Groth et al. "Phage integrases: biology and applications," Journal of Molecular Biology, 2004, vol. 335, pp. 667-678.
Groth, et al. "A phage integrase directs efficient site-specific integration in human cells", PNAS, 2000, vol. 97, No. 11, pp. 5995-6000.
Guatteo, et al. "Temperature sensitivity of dopaminergic neurons of the substantia nigra pars compacta: Involvement of transient receptor potential channels," Journal of Neurophysiol. , 2005, vol. 94, pp. 3069-3080.
Gulick, et al. "Transfection using DEAE-Dextran" Supplement 40, Current Protocols in Molecular Biology, 1997, Supplement 40, 9.2.1-9.2.10.
Gur et al., "A Dissociation Between Brain Activity and Perception: Chromatically Opponent Cortical Neurons Signal Chromatic Flicker that is not Perceived", Vision Research, 1997, vol. 37, No. 4, pp. 377-382.
Hallet et al. "Transposition and site-specific recombination: adapting DNA cut-and-paste mechanisms to a variety of genetic rearrangements," FEMS Microbiology Reviews, 1997, vol. 21, No. 2, pp. 157-178.
Hamer, et al. "Regulation In Vivo of a cloned mammalian gene: cadmium induces the transcription of a mouse metallothionein gene in SV40 vectors," Journal of Molecular Applied Genetics, 1982, vol. 1, No. 4, pp. 273-288.
Hausser, et al. "Tonic Synaptic Inhibition Modulates Neuronal Output Pattern and Spatiotemporal Synaptic Integration", Neuron, 1997, vol. 19, pp. 665-678.
Hegemann et al., "All-trans Retinal Constitutes the Functional Chromophore in *Chlamydomonas* rhodopsin", Biophys. J. , 1991, vol. 60, pp. 1477-1489.
Herlitze, et al., "New Optical Tools for Controlling Neuronal Activity", 2007, Curr Opin Neurobiol, vol. 17, No. 1, pp. 87-94.
Herry, et al. "Switching on and off fear by distinct neuronal circuits," Nature, 2008, vol. 454, pp. 600-606.
Hildebrandt et al, "Bacteriorhodopsin expressed in *Schizosaccharomyces pombe* pumps protons through the plasma membrane," PNAS, 1993, vol. 90, pp. 3578-3582.
Hirase, et al. "Multiphoton stimulation of neurons", J Neurobiol, 2002, vol. 51, No. 3: pp. 237-247.
Hodaie, et al., "Chronic Anterior Thalamus Stimulation for Intractable Epilepsy," Epilepsia, 2002, vol. 43, pp. 603-608.
Hoffman et al., "K+ Channel Regulation of Signal Propagation in Dendrites of Hippocampal Pyramidal Neurons", 1997, Nature, vol. 387: pp. 869-874.
Hosokawa, T. et al. "Imaging spatio-temporal patterns of long-term potentiation in mouse hippocampus." Philos. Trans. R. Soc. Lond. B., 2003, vol. 358, pp. 689-693.
Hynynen, et al. "Clinical applications of focused ultrasound—The brain." Int. J. Hyperthermia, 2007, vol. 23, No. 2: pp. 193-202.
International Search Report for International Application No. PCT/US2009/053474, dated Oct. 8, 2009.
Isenberg et al. "Cloning of a Putative Neuronal Nicotinic Aceylcholine Receptor Subunit," Journal of Neurochemistry, 1989, pp. 988-991.
Jekely, "Evolution of Phototaxis", 2009, Phil. Trans. R. Soc. B, vol. 364, pp. 2795-2808.
Johansen, et al., "Optical Activation of Lateral Amygdala Pyramidal Cells Instructs Associative Fear Learning", 2010, PNAS, vol. 107, No. 28, pp. 12692-12697.
Johnston et al. "Isolation of the yeast regulatory gene GAL4 and analysis of its dosage effects on the galactose/melibiose regulon," PNAS, 1982, vol. 79, pp. 6971-6975.
Kandel, E.R., et al. "Electrophysiology of Hippocampal Neurons: I. Sequential Invasion and Synaptic Organization," J Neurophysiol, 1961, vol. 24, pp. 225-242.
Kandel, E.R., et al. "Electrophysiology of Hippocampal Neurons: II. After- Potentials and Repetitive Firing", J Neurophysiol., 1961, vol. 24, pp. 243-259.
Karreman et al. "On the use of double FLP recognition targets (FRTs) in the LTR of retroviruses for the construction of high producer cell lines", Nucleic Acids Research, 1996, vol. 24, No. 9: pp. 1616-1624.
Kato et al. "Present and future status of noninvasive selective deep heating using RF in hyperthermia." Med & Biol. Eng. & Comput 31 Supp: S2-11, 1993. Abstract. p. S2 only.
Katz, et al. "Scanning laser photostimulation: a new approach for analyzing brain circuits," Journal of Neuroscience Methods, 1994, vol. 54, pp. 205-218.
Khodakaramian, et al. "Expression of Cre Recombinase during Transient Phage Infection Permits Efficient Marker Removal in *Streptomyces*," Nucleic Acids Research, 2006, vol. 34, No. 3:e20, pp. 1-5.
Khosravani et al., "Voltage-Gated Calcium Channels and Idiopathic Generalized Epilepsies", Physiol. Rev., 2006, vol. 86: pp. 941-966.
Kianianmomeni, et al. "Channelrhodopsins of Volvox carteri are Photochromic Proteins that are Specifically Expressed in Somatic

(56) References Cited

OTHER PUBLICATIONS

Cells under Control of Light, Temperature, and the Sex Inducer", 2009, Plant Physiology, vol. 151, No. 1, pp. 347-366.
Kim et al., "Light-Driven Activation of β2-Adrenergic Receptor Signaling by a Chimeric Rhodopsin Containing the β2-Adrenergic Receptor Cytoplasmic Loops," Biochemistry, 2005, vol. 44, No. 7, pp. 2284-2292.
Kingston et al. "Transfection of DNA into Eukaryotic Cells," Supplement 63, Current Protocols in Molecular Biology, 1996, 9.1.1-9.1.11, 11 pages.
Kingston et al. "Transfection and Expression of Cloned DNA," Supplement 31, Current Protocols in Immunology, 1999, 10.13.1-10.13.9.
Kita, H. et al. "Effects of dopamine agonists and antagonists on optical responses evoked in rat frontal cortex slices after stimulation of the subcortical white matter," Exp. Brain Research, 1999, vol. 125, pp. 383-388.
Kitayama, et al. "Regulation of neuronal differentiation by N-methyl-D-aspartate receptors expressed in neural progenitor cells isolated from adult mouse hippocampus," Journal of Neurosci Research, 2004, vol. 76, No. 5: pp. 599-612.
Klausberger, et al. "Brain-state- and cell-type-specific firing of hippocampal interneurons in vivo", Nature, 2003, vol. 421: pp. 844-848.
Kocsis et al., "Regenerating Mammalian Nerve Fibres: Changes in Action Potential Wavefrom and Firing Characteristics Following Blockage of Potassium Conductance", 1982, Proc. R. Soc. Lond., vol. B 217: pp. 77-87.
Knopfel, et al. "Optical Probin of Neuronal Circuit Dynamics: Gentically Encoded Versus Classical Fluorescent Sensors", 2006, Trends Neurosci, vol. 29, No. 3, pp. 160-166.
Kuhlman et al. (2008) "High-Resolution Labeling and Functional Manipulation of Specific Neuron Types in Mouse Brain by Cre-Activated Viral Gene Expression" PLoS One, 2005, vol. 3, No. 4, pp. 1-11.
Kunkler, P. et at. "Optical Current Source Density Analysis in Hippocampal Organotypic Culture Shows that Spreading Depression Occurs with Uniquely Reversing Current," The Journal of Neuroscience, 2005, vol. 25, No. 15, pp. 3952-3961.
Landy, A. "Mechanistic and structural complexity in the site-specific recombination pathways of Int and FLP", Current Opinion in Genetics and Development, 1993, vol. 3, pp. 699-707.
Lee et al. "Sterotactic Injection of Adenoviral Vectors that Target Gene Expression to Specific Pituitary Cell Types: Implications for Gene Therapy", Neurosurgery, 2000, vol. 46, No. 6: pp. 1461-1469.
Lee et al., "Potassium Channel Gone Therapy Can Prevent Neuron Deatch Resulting from Necrotic and Apoptotic Insults", Journal of Neurochemistry, 2003, vol. 85: pp. 1079-1088.
Levitan et al. "Surface Expression of Kv1 Voltage-Gated K+ Channels Is Governed by a C-terminal Motif," Trends Cardiovasc. Med., 2000, vol. 10, No. 7, pp. 317-320.
Li et al. "Fast noninvasive activation and inhibition of neural and network activity by vertebrate rhodopsin and green algae *channelrhodopsin*." PNAS, 2005, vol. 102, No. 49, p. 17816-17821.
Lim et al., "A Novel Targeting Signal for Proximal Clustering of the Kv2.1K+ Channel in Hippocampal Neurons", Neuron, 2000, vol. 25: pp. 385-397.
Lima, et al. "Remote Control of Behavior through Genetically Targeted Photostimulation of Neurons", Cell, 2005, vol. 121: pp. 141-152.
Liman, et al. "Subunit Stoichiometry of a Mammalian K+ Channel Determined by Construction of Multimeric cDNAs," Neuron, 1992, vol. 9, pp. 861-871.
Louis et al. "Cloning and sequencing of the cellular-viral junctions from the human adenovirus type 5 transformed 293 cell line," Virology, 1997, vol. 233, pp. 423-429.
Luecke, et al. "Structural Changes in Bacteriorhodopsin During Ion Transport at 2 Angstrom Resolution," Science, 1999, vol. 286, pp. 255-260.

Lyznik, et al. "FLP-mediated recombination of FRT sites in the maize genome," Nucleic Acids Research, 1996, vol. 24, No. 19: pp. 3784-3789.
Ma et al. "Role of ER Export Signals in Controlling Surface Potassium Channel Numbers," Science, 2001, vol. 291, pp. 316-319.
Mann et at. "Perisomatic Feedback Inhibition Underlies Cholinergically Induced Fast Network Oscillations in the Rat Hippocampus in Vitro," Neuron, 2005, vol. 45, 2005, pp. 105-117.
Mattson, "Apoptosis in Neurodegenerative Disorders", Nature Reviews, 2000, vol. 1: pp. 120-129.
Mayberg et al. "Deep Brain Stimulation for Treatment-Resistant Depression," Focus, 2008, vol. VI, No. 1, pp. 143-154.
McAllister, "Cellular and Molecular Mechanisms of Dendrite Growth", 2000, Cereb Cortex, vol. 10, No. 10, pp. 963-973.
McKnight "Functional relationships between transcriptional control signals of the thymidine kinase gene of herpes simplex virus", Cell, 1982, vol. 31 pp. 355-365.
Melyan, Z., et al. "Addition of human melanopsin renders mammalian cells Photoresponsive", Nature, 2005, vol. 433: pp. 741-745.
Mermelstein, et al. "Critical Dependence of cAMP Response Element-Binding Protein Phosphorylation on L-Type Calcium Channels Supports a Selective Response to EPSPs in Preference to Action Potentials", The Journal of Neuroscience, 2000, vol. 20, No. 1, pp. 266-273.
Meyer, et al. "High density interconnects and flexible hybrid assemblies for active biomedical implants," IEEE Transactions on Advanced Packaging, 2001, vol. 24, No. 3, pp. 366-372.
Monje et al., "Irradiation Induces Neural Precursor-Cell Dysfunction", Natural Medicine, 2002, vol. 8, No. 9, pp. 955-962.
Mortensen et al. "Selection of Transfected Mammalian Cells," Supplement 86, Current Protocols in Molecular Biology, 1997, 9.5.1-09.5.19.
Nacher, et al. "NMDA receptor antagonist treatment increases the production of newneurons in the aged rat hippocampus", Neurobiology of Aging, 2003,vol. 24, No. 2: pp. 273-284.
Nagel et al. "Functional Expression of Bacteriorhodopsin in Oocytes Allows Direct Measurement of Voltage Dependence of Light Induced H+ Pumping," FEBS Letters, 1995, vol. 377, pp. 263-266.
Nagel, et al. "Channelrhodopsin-I: a light-gated proton channel in green algae", Science, 2002, vol. 296: pp. 2395-2398.
Nagel, et al. "Channelrhodopsin-2, a directly light-gated cation-selective membrane channel", PNAS, 2003, vol. 100, No. 24: pp. 13940-13945.
Nakagami, et al. "Optical Recording of Trisynaptic Pathway in Rat Hippocampal Slices with a Voltage-Sensitive Dye" Neuroscience, 1997, vol. 81, No. 1, pp. 1-8.
Naqvi, et al. "Damage to the insula disrupts addiction to cigarette smoking," Science; 2007, vol. 315 pp. 531-534.
Natochin, et al. "Probing rhodopsin-transducin interaction using *Drosophila* Rh1-bovine rhodopsin chimeras," Vision Res., 2006, vol. 46, No. 27: pp. 4575-4581.
Nirenberg, et al. "The Light Response of Retinal Ganglion Cells is Truncated by a Displaced Amacrine Circuit", Neuron, 1997, vol. 18: pp. 637-650.
Nunes-Duby, et al. "Similarities and differences among 105 members of the Int family of site-specific recombinases", Nucleic Acids Research, 1998, vol. 26, No. 2: pp. 391-406.
O'Gorman et al. "Recombinase-mediated gene activation and site-specific integration in mammalian cells", Science, 1991, 251(4999): pp. 1351-1355.
Olivares (2001) "Phage R4 integrase mediates site-specific integration in human cells", Gene, 2001, vol. 278, pp. 167-176.
Ory, et al. "A stable human-derived packaging cell line for production of high titer retrovirus/vesicular stomatitis virus G pseudotypes," PNAS, 1996, vol. 93: pp. 11400-11406.
Palmer et al., "The Adult Rat Hippocampus Contains Primordial Neural Stem Cells", Molecular and Cellular Neuroscience, 1997, vol. 8, pp. 389-404.
Palmer et al., "Fibroblast Growth Factor-2 Activates a Latent Neurogenic Program in Neural Stem Cells from Diverse Regions of the Adult CNS", The Journal of Neuroscience, 1999, vol. 19, pp. 8487-8497.

(56) References Cited

OTHER PUBLICATIONS

Pan et al. "Functional Expression of a Directly Light-Gated Membrane Channel in Mammalian Retinal Neurons: A Potential Strategy for Restoring Light Sensitivity to the Retina After Photoreceptor Degeneration," Investigative Opthalmology & Visual Science, 2005, 46 E-Abstract 4631. Abstract only.
Panda, et al. "Illumination of the Melanopsin Signaling Pathway", Science, 2005, vol. 305: pp. 600-604.
Pape, et al., "Plastic Synaptic Networks of the Amygdala for the Acquisition, Expression, and Extinction of Conditioned Fear", 2010, Physiol Rev, vol. 90, pp. 419-463.
Paulhe et al. "Specific Endoplasmic Reticulum Export Signal Drives Transport of Stem Cell Factor (Kitl) to the Cell Surface," The Journal of Biological Chemistry, 2004, vol. 279, No. 53, p. 55545-55555.
Pear "Transient Transfection Methods for Preparation of High-Titer Retroviral Supernatants" Supplement 68, Current Protocols in Molecular Biology, 1996, 9.1 1 .1-9.1 1 .1 8.
Peterlin, et al. "Optical probing of neuronal circuits with calcium indicators," PNAS, 2000, vol. 97, No. 7: pp. 3619-3624.
Petersen et al. "Spatiotemporal Dynamics of Sensory Responses in Layer 2/3 of Rat Barrel Cortex Measured In Vivo by Voltage-Sensitive Dye Imaging Combined with Whole-Cell Voltage Recordings and Neuron Reconstructions," The Journal of Neuroscience, 2003, vol. 23, No. 3, pp. 1298-1309.
Petrecca, et al. "Localization and Enhanced Current Density of the Kv4.2 Potassium Channel by Interaction with the Actin-Binding Protein Filamin," The Journal of Neuroscience, 2000, vol. 20, No. 23, pp. 8736-8744.
Pettit, et al. "Local Excitatory Circuits in the Intermediate Gray Layer of the Superior Colliculus", J Neurophysiol., 1999, vol. 81, No. 3: pp. 1424-1427.
Potter, "Transfection by Electroporation." Supplement 62, Current Protocols in Molecular Biology, 1996, 9.3.1-9.3.6.
Pouille, et al. "Routing of spike series by dynamic circuits in the hippocampus", Nature, 2004, vol. 429: pp. 717-723.
Qiu et al. "Induction of photosensitivity by heterologous expression of melanopsin", Nature, 2005, vol. 433: pp. 745-749.
Rammes, et al., "Synaptic Plasticity in the Basolateral Amygdala in Transgenic Mice Expressing Dominant-Negative cAMP Response Element-binding Protein (CREB) in Forebrain", Eur J. Neurosci, 2000, vol. 12, No. 7: pp. 2534-2546.
Randic, et al. "Long-term Potentiation and Long-term Depression of Primary Afferent Neurotransmission in the Rat Spinal Cord", 1993, Journal of Neuroscience, vol. 13, No. 12, pp. 5228-5241.
Rathnasingham et al., "Characterization of implantable microfabricated fluid delivery devices," IEEE Transactions on Biomedical Engineering, 2004, vol. 51, No. 1: pp. 138-145.
Ritter, et al., "Monitoring Light-induced Structural Changes of Channelrhodopsin-2 by UV-Visible and Fourier Transform Infared Spectroscopy", 2008, The Journal of Biological Chemistry, vol. 283, No. 50, pp. 35033-35041.
Rivera et al., "BDNF-Induced TrkB Activation Down-Regulates the K+-Cl-cotransporter KCC2 and Impairs Neuronal Cl-Extrusion", The Journal of Cell Biology, 2002, vol. 159: pp. 747-752.
Rosenkranz, et al. "The prefrontal cortex regulates lateral amygdala neuronal plasticity and responses to previously conditioned stimuli", J. Neurosci., 2003, vol. 23, No. 35: pp. 11054-11064.
Rousche, et al., "Flexible polyimide-based intracortical electrode arrays with bioactive capability," IEEE Transactions on Biomedical Engineering, 2001, vol. 48, No. 3, pp. 361-371.
Rubinson et at. "A lentivirus-based system to functionally silence genes in primary mammalian cells, stem cells and transgenic mice by RNA interference," Nature Genetics, 2003, vol. 33, p. 401-406.
Rudiger et at. "Specific arginine and threonine residues control anion binding and transport in the light-driven chloride pump halorhodopsin," The EMBO Journal, 1997, vol. 16, No. 13, pp. 3813-3821.
Salzman, et al. "Cortical microstimulation influences perceptual judgements of motion direction", Nature, 1990, vol. 346, pp. 174-177.
Sajdyk, et al., "Excitatory Amino Acid Receptors in the Basolateral Amygdala Regulate Anxiety Responses in the Social Interaction Test", Brain Research, 1997, vol. 764, pp. 262-264.
Sato et al. "Role of Anion-binding Sites in cytoplasmic and extracellular channels of *Natronomonas pharaonis halorhodopsin*," Biochemistry, 2005. vol. 44, pp. 4775-4784.
Sauer "Site-specific recombination: developments and applications," Current Opinion in Biotechnology, 1994, vol. 5, No. 5: pp. 521-527.
Schiff, et al. "Behavioral improvements with thalamic stimulation after severe traumatic brain injury," Nature, 2007, vol. 448, pp. 600-604.
Schlaepfer et al. "Deep Brain stimulation to Reward Circuitry Alleviates Anhedonia in Refractory Major Depresion," Neuropsychopharmacology, 2008, vol. 33, pp. 368-377.
Sclimenti, et al. "Directed evolution of a recombinase for improved genomic integration at a native human sequence," Nucleic Acids Research, 2001, vol. 29, No. 24: pp. 5044-5051.
Shepherd, et al. "Circuit Analysis of Experience-Dependent Plasticity in the Developing Rat Barrel Cortex", Neuron, 2003, vol. 38: pp. 277-289.
Shibasaki et al. "Effects of body temperature on neural activity in the hippocampus: Regulation of resting membrane potentials by transient receptor potential vanilloid 4," The Journal of Neuroscience, 2007, vol. 27, No. 7: pp. 1566-1575.
Silver, et al. "Amino terminus of the yeast GAL4 gene product is sufficient for nuclear localization" PNAS, 1984, vol. 81, No. 19: pp. 5951-5955.
Singer et al. "Elevated Intrasynaptic Dopamine Release in Tourette's Syndrome Measured by PET," American Journal of Psychiatry, 2002, vol. 159: pp. 1329-1336.
Slimko et al., "Selective Electrical Silencing of Mammalian Neurons In Vitro by the use of Invertebrate Ligand-Gated Chloride Channels", The Journal of Neuroscience, 2002, vol. 22, No. 17: pp. 7373-7379.
Smith et al. "Diversity in the serine recombinases", Molecular Microbiology, 2002, vol. 44, No. 2: pp. 299-307.
Song et al. "Differential Effect of TEA on Long-Term Synaptic Modification in Hippocampal CA1 and Dentate Gyrus in vitro." Neurobiology of Learning and Memory, 2001, vol. 76, No. 3, pp. 375-387.
Song, "Genes responsible for native depolarization-activated K+ currents in neurons," Neuroscience Research, 2002, vol. 42, pp. 7-14.
Stark, et al. "Catalysis by site-specific recombinases," Trends Genet., 1992, vol. 8, No. 12: pp. 432-439.
Stockklausner et al. "A sequence motif responsible for ER export and surface expression of Kir2.0 inward rectifier K+ channels," FEBS Letters, 2001, vol. 493, pp. 129-133.
Stoll, et al. "Phage TP901-I site-specific integrase functions in human cells," Journal of Bacteriology, 2002, vol. 184, No. 13: pp. 3657-3663.
Swanson, "Lights, Opsins, Action! Optogenetics Brings Complex Neuronal Circuits into Sharper Focus", 2009, The Dana Foundation, [URL: http://www.dana.org/news/features/detail.aspx?id=24236], PDF File, pp. 1-3.
Swiss-Prot_Q2QCJ4, Opsin 1, Oct. 31, 2006, URL: http://www.ncbi.nlm.nig.gov/protein/Q2QCJ4.
Takahashi, et al."Diversion of the Sign of Phototaxis in a *Chlamydomonas reinhardtii* Mutant Incorporated with Retinal and Its Analogs," FEBS Letters, 1992, vol. 314, No. 3, pp. 275-279.
Tatarkiewicz, et al. "Reversal of Hyperglycemia in Mice After Subcutaneous Transplantation of Macroencapsulated Islets", Transplantation, 1999, vol. 67, No. 5: pp. 665-671.
Tottene et al., "Familial Hemiplegic Migraine Mutations Increase $Ca^{2+}$ Influx Through Single Human $Ca_v2.1$ Current Density in Neurons", PNAS USA, 2002, vol. 99, No. 20: pp. 13284-13289.

(56) References Cited

OTHER PUBLICATIONS

Tsau et al. "Distributed Aspects of the Response to Siphon Touch in *Aplysia*: Spread of Stimulus Information and Cross-Correlation Analysis," The Journal of Neuroscience, 1994, vol. 14, No. 7, pp. 4167-4184.
[No Authors Listed] "Two bright new faces in gene therapy," Nature Biotechnology, 1996, vol. 14: p. 556.
Tye et. al., "Amygdala circuitry mediating reversible and bidirectional control of anxiety", Nature, 2011, vol. 471(7338): pp. 358-362.
Tye et. al., Supplementary Materials: "An optically-resolved microcircuit for bidirectional anxiety control", Nature, 2011, vol. 471(7338): pp. 358-362.
Tye, et al. "Optogenetic investigation of neural circuits underlying brain disease in animal models," Nature Reviews Neuroscience (Mar. 2012), 13(4):251-266.
"SubName: Full=Channelrhodopsin-1", retrieved from EBI accession No. UNIPROT: B4Y103. Database accession No. B4Y103. Sep. 23, 2008.
Ulmanen, et al. "Transcription and translation of foreign genes in *Bacillus subtilis* by the aid of a secretion vector," Journal of Bacteriology, 1985, vol. 162, No. 1: pp. 176-182.
Van Der Linden, "Functional brain imaging and pharmacotherapy in social phobia: single photon emission computed tomography before and after Treatment with the selective serotonin reuptake inhibitor citalopram," Prog Neuro-psychopharmacol Biol Psychiatry, 2000, vol. 24, No. 3: pp. 419-438.
Vanin, et al. "Development of high-titer retroviral producer cell lines by using Cre-mediated recombination," Journal of Virology, 1997, vol. 71, No. 10: pp. 7820-7826.
Vetter, et al. "Development of a Microscale Implantable Neural Interface (MINI) Probe System," Proceedings of the 2005 IEEE, Engineering in Medicine and Biology 27th Annual Conference, Shanghai, China, Sep. 1-4, 2005.
Wagner, "Noninvasive Human Brain Stimulation", Annual Rev. Biomed. Eng. 2007. 9:I9.1-19.39.
Ward, et al. "Construction and characterisation of a series of multi-copy promoter-probe plasmid vectors for *Streptomyces* using the aminoglycoside phosphotransferase gene from Tn5 as indicator", 1986, Mol. Gen. Genet., vol. 203: pp. 468-478.
Watson, et al. "Targeted transduction patterns in the mouse brain by lentivirus vectors pseudotyped with VSV, Ebola, Mokola, LCMV, or MuLV envelope proteins," Molecular Therapy, 2002, vol. 5, No. 5, pp. 528-537.
Wang et al. "Direct-current Nanogenerator Driven by Ultrasonic Waves," Science, 2007, vol. 316, pp. 102-105.
Wang et. al., "High-speed mapping of synaptic connectivity using photostimulation in Channelrhodopsin-2 transgenic mice", PNAS, 2007, vol. 104, No. 19, pp. 8143-8148.
Weick et al. "Interactions with PDZ Proteins Are Required for L-Type Calcium Channels to Activate cAMP Response Element-Binding Protein-Dependent Gene Expression," The Journal of Neuroscience, 2003, vol. 23, No. 8, pp. 3446-3456.
Wells et al. "Application of Infrared light for in vivo neural stimulation," Journal of Biomedical Optics, 2005, vol. 10(6), pp. 064003-1-064003-12.
Witten et. al., Supporting Online Material for: "Cholinergic Interneurons Control Local Circuit Activity and Cocaine Conditioning", Science, 2010, vol. 330: 17 pages.
Witten et. al., "Cholinergic Interneurons Control Local Circuit Activity and Cocaine Conditioning", Science, 2010, vol. 330, No. 6011: pp. 1677-1681.
Yamazoe, et al. "Efficient generation of dopaminergic neurons from mouse embryonic stem cells enclosed in hollow fibers", Biomaterials, 2006, vol. 27, pp. 4871-4880.
Yan et al., "Cloning and Characterization of a Human $\beta$, $\beta$-Carotene-15, 15'-Dioxygenase that is Highly Expressed in the Retinal Pigment Epithelium", Genomics, 2001, vol. 72: pp. 193-202.

Yizhar et. al., "Neocortical excitation/inhibition balance in information processing and social dysfunction", Nature, 2011, vol. 477, pp. 171-178; and Supplemental Materials; 41 pages.
Yoon, et al., "A micromachined silicon depth probe for multichannel neural recording," IEEE Transactions Biomedical Engineering, 2000, vol. 47, No. 8, pp. 1082-1087.
Yoshimura, et al. "Excitatory cortical neurons form fine-scale functional networks", Nature, 2005, vol. 433: pp. 868-873.
Zacharias et al. "Recent advances in technology for measuring and manipulating cell signals," Current Opinion in Neurobiology, 2000, vol. 10: pp. 416-421.
Zemelman, et al. "Selective Photostimulation of Genetically ChARGed Neurons", Neuron, 2002, vol. 33: pp. 15-22.
Zemelman, et al. "Photochemical gating of heterologous ion channels: Remote control over genetically designated populations of neurons", PNAS, 2003, vol. 100, No. 3: pp. 1352-1357.
Zhang, et al. "Channelrhodopsin-2 and optical control of excitable cells," Nature Methods, 2006, vol. 3, No. 10, pp. 785-792.
Zhang, et al. "Red-Shifted Optogenetic Excitation: a Tool for Fast Neural Control Derived from *Volvox carteri*", Nature Neurosciences, 2008, vol. 11, No. 6, pp. 631-633.
Zhang "Multimodal fast optical interrogation of neural circuitry," Nature, 2007, vol. 446, pp. 633-641.
Zrenner, E., "Will Retinal Implants Restore Vision?" Science, 2002, vol. 295, No. 5557, pp. 1022-1025.
Zufferey, et al. "Self-Inactivating Lentivirus Vector for Safe and Efficient In Vivo Gene Delivery", Journal of Virology, 1998, vol. 72, No. 12, pp. 9873-9880.
Barchet, et al.; "Challenges and opportunities in CNS delivery of therapeutics for neurodegenerative diseases"; Expert Opinion on Drug Delivery; vol. 6, No. 3, pp. 211-225 (Mar. 16, 2009).
Bowers, et al.; "Genetic therapy for the nervous system"; Human Molecular Genetics; vol. 20, No. 1, pp. R28-R41 (2011).
Castagne, et al.; "Rodent Models of Depression: Forced Swim and Tail Suspension Behavioral Despair Tests in Rats and Mice"; Current Protocols in Pharmacology; Supp. 49, Unit 5.8.1-5.8.14 (Jun. 2010).
Friedman, et al.; "Programmed Acute Electrical Stimulation of Ventral Tegmental Area Alleviates Depressive-Like Behavior"; Neuropsychopharmacology; vol. 34, pp. 1057-1066 (2009).
GenBank Accession No. AC096118.6; Rattus norvegicus clone CH230-11 B15, 1-4, 24-25, Working Draft Sequence, 3 unordered pieces. May 10, 2003.
GenBank Accession No. U79717.1; Rattus norvegicus dopamine 02 receptor 1-4, 24-25 gene, promoter region and exon 1. Jan. 31, 1997.
Haim, et al.; "Gene Therapy to the Nervous System"; Stem Cell and Gene-Based Therapy; Section 2, pp. 133-154 (2006).
Pandya, et al.; "Where in the Brain Is Depression?"; Curr. Psychiatry Rep.; vol. 14, pp. 634-642 (2012).
Stonehouse, et al.; "Caffeine Regulates Neuronal Expression of the Dopamine 2 Receptor Gene"; Molecular Pharmacology; vol. 64, No. 6, pp. 1463-1473 (2003).
Ibbin I, et al.; "A Field Conjugation Method for Direct Synthesis of Hyperthermia Phased-Array Heating Patterns"; IEEE Transactions on Ultrasonics, Ferroelectrics, and Frequency Control; vol. 36, No. 1, pp. 3-9 (Jan. 1989).
Goshen, et al.; "Dynamics of Retrieval Strategies for Remote Memories"; Cell; vol. 147, pp. 678-689 (Oct. 28, 2011).
Johansen, et al.; "Controlling the elements: an optogenetic approach to understanding the neural circuits of fear"; Biol. Psychiatry; vol. 71, No. 12, pp. 1053-1060 (Jun. 15, 2012).
McKenzie, et al.; "New approach illuminates how memory systems switch"; Trends in Cognitive Sciences; vol. 16, No. 2 (Feb. 2012).
Sakaguchi, et al.; "Inhibiting the Activity of CA1 Hippocampal Neurons Prevents the Recall of Contextual Fear Memory in Inducible ArchT Transgenic Mice"; PLoSOne; 11 pages (Jun. 15, 2015).
Suzuki, et al.; "Two Routes for Remembering the Past"; Cell; vol. 147, pp. 493-495 (Oct. 28, 2011).
Welberg; "CA1 triggers the trace"; Nature Reviews Neuroscience; vol. 12, 1 page (Nov. 9, 2011).
Berlanga, et a.; "Cholinergic Interneurons of the Nucleus Accumbens and Dorsal Striatum are Activated by the Self-Administration of Cocaine"; Neuroscience; vol. 120, pp. 1149-1156 (2003).

(56) References Cited

OTHER PUBLICATIONS

Day, et al.; "The Nucleus Accumbens and Pavlovian Reward Learning"; Neuroscientist; vol. 13, No. 2, pp. 148-159 (Apr. 2007).
Knopfel, et al.; "A comprehensive concept of optogenetics"; Progress in Brain Research; vol. 196, pp. 1-28 (2012).
Packer, et al.; "Targeting Neurons and Photons for Optogenetics"; Nature Neuroscience; vol. 16, No. 7, pp. 805-815 (Jul. 2013).
Han, et al., "Millisecond-Timescale Optical Control of Neural Dynamics in the Nonhuman Primate Brain"; Neuron; vol. 62, pp. 191-198 (Apr. 30, 2009).
Han, et a.; "Virogenetic and optogenetic mechanisms to define potential therapeutic targets in psychiatric disorders"; Neuropharmacology; vol. 62, pp. 89-100 (2012).
Zhang, et al.; "Optogenetic interrogation of neural circuits: Technology for probing mammalian brain structures"; Nature Protocols; vol. 5, No. 3, pp. 439-456 (Mar. 1, 2010).
Ali; "Gene and stem cell therapy for retinal disorders"; vision-research.en—The Gateway to European Vision Research; accessed from http://www.vision-research.eu/index.php?id=696, 10 pages (accessed Jul. 24, 2015).
Asano, et al.; "Optically Controlled Contraction of Photosensitive Skeletal Muscle Cells"; Biotechnology & Bioengineering; vol. 109, No. 1, pp. 199-204 (Jan. 2012).
Bruegmann, et al.; "Optogenetic control of heart muscle in vitro and in vivo"; Nature Methods; vol. 7, No. 11, pp. 897-900(Nov. 2010).
Bruegmann, et al.; "Optogenetics in cardiovascular research: a new tool for light-induced depolarization of cardiomyocytes and vascular smooth muscle cells in vitro and in vivo"; European Heart Journal; vol. 32, No. Suppl . 1, p. 997 (Aug. 2011).
Genbank Accession No. AAG01180.1; Idnurm, et al.; pp. 1 (Mar. 21, 2001).
Genbank Accession No. ABT17417.1; Sharma, et al.; pp. 1 (Aug. 15, 2007).
Genbank Accession No. BAA09452.1; Mukohata et al.; pp. 1 (Feb. 10, 1999).
Kessler, et al.; "Gene delivery to skeletal muscle results in sustained expression and systemic delivery of a therapeutic protein"; Proc. Natl. Acad. Sci. USA; vol. 93, pp. 14082-14087 (Nov. 1996).
Mueller, et al.; "Clinical Gene Therapy Using Recombinant Adeno-Associated Virus Vectors"; Gene Therapy; vol. 15, pp. 858-863 (2008).
Wang, et al.; "Laser-evoked synaptic transmission in cultured hippocampal neurons expressing channelrhodopsin-2 delivered by adeno-associated virus"; Journal of Neuroscience Methods; vol. 183, pp. 165-175 (2009).
Brewin; "The Nature and Significance of Memory Disturbance in Posttraumatic Stress Disorder"; Ann. Rev. Clin. Psychol.; vol. 7, pp. 203-227 (2011).
Raper, et al.; "Fatal systemic inflammatory response syndrome in a ornithine transcarbamylase deficient patient following adenoviral gene transfer." Mol. Genet. Metab.; vol. 80, No. 1-2, pp. 148-158 (Sep.-Oct. 2003).
Samuelson; "Post-traumatic stress disorder and declarative memory functioning: a review"; Dialogues in Clinical Neuroscience; vol. 13, No. 3, pp. 346-351 (2011).
Chamanzar, et al.; "Deep Tissue Targeted Near-infrared Optogenetic Stimulation using Fully Implantable Upconverting Light Bulbs"; 2015 37th Annual International Conference of the IEEE Engineering in Medicine and Biology Society (EMBC), IEEE; doi: 10.1109/EMBC.2015.7318488, pp. 821-824 (Aug. 25, 2015).
Hososhima, et al.; "Near-infrared (NIR) up-conversion optogenetics"; Optical Techniques in Neurosurgery, Neurophotonics, and Optogenetics II; vol. 9305, doi: 10.1117/12.2078875, 4 pages. (2015).
Wang, et al.; "Simultaneous phase and size control of upconversion nanocrystals through lanthanide doping"; Nature; vol. 463, No. 7284, pp. 1061-1065 (Feb. 25, 2010).
Clark, et al.; "A future for transgenic livestock"; Nature Reviews Genetics; vol. 4, No. 10, pp. 825-833 (Oct. 2003).

Do Carmo, et al.; "Modeling Alzheimer's disease in transgenic rats"; Molecular Neurodegeneration; vol. 8, No. 37, 11 pages (2013).
Heymann, et al.; "Expression of Bacteriorhodopsin in Sf9 and COS-1 Cells"; Journal of Bioenergetics and Biomembranes; vol. 29, No. 1, pp. 55-59 (1997).
Ramalho, et al.; "Mouse genetic corneal disease resulting from transgenic insertional mutagenesis"; Br. J. Ophthalmol.; vol. 88, No. 3, pp. 428-432 (Mar. 2004).
Ristevski; "Making Better Transgenic Models: Conditional, Temporal, and Spatial Approaches"; Molecular Biotechnology; vol. 29, No. 2, pp. 153-163 (Feb. 2005).
Sigmund; "Viewpoint: Are Studies in Genetically Altered Mice Out of Control?"; Arterioscler Thromb Vasc. Biol.; vol. 20, No, 6, pp. 1425-1429 (Jun. 2000).
Sineshchekov et al.; "Intramolecular Proton Transfer in Channelrhodopsins"; Biophysical Journal; vol. 104, No. 4, pp. 807-807 (Feb. 2013).
Airan, et al.; "Integration of light-controlled neuronal firing and fast circuit imaging"; Current Opinion in Neurobiology; vol. 17, pp. 587-592 (2007).
Cannon, et al.; "Endophenotypes in the Genetic Analyses of Mental Disorders"; Annu. Rev. Clin. Psychol.; vol. 2, pp. 267-290 (2006).
Chinta, et al.; "Dopaminergic neurons"; The International Journal of Biochemistry & Cell Biology; vol. 37, pp. 942-946 (2005).
Deonarain; "Ligand-targeted receptor-mediated vectors for gene delivery"; Exp. Opin. Ther. Patents; vol. 8, No. 1, pp. 53-69 (1998).
Edelstein, et al.; "Gene therapy clinical trials worldwide 1989-2004—an overview"; The Journal of Gene Medicine; vol. 6, pp. 597-602 (2004).
Grady, et al.; "Age-Related Reductions in Human Recognition Memory Due to Impaired Encoding"; Science; vol. 269, No. 5221, pp. 218-221 (Jul. 14, 1995).
Johnson-Saliba, et al.; "Gene Therapy: Optimising DNA Delivery to the Nucleus"; Current Drug Targets; vol. 2, pp. 371-399 (2001).
Palu, et al.; "In pursuit of new developments for gene therapy of human diseases"; Journal of Biotechnology; vol. 68, pp. 1-13 (1999).
Petersen, et al.; "Functionally Independent Columns of Rat Somatosensory Barrel Cortex Revealed with Voltage-Sensitive Dye Imaging"; J. of Neuroscience; vol. 21, No. 21, pp. 8435-8446 (Nov. 1, 2011).
Pfeifer, et al.; "Gene Therapy: Promises and Problems"; Annu. Rev. Genomics Hum. Genet.; vol. 2, pp. 177-211 (2001).
Powell, et al.; "Schizophrenia-Relevant Behavioral Testing in Rodent Models: A Uniquely Human Disorder?"; Biol. Psychiatry; vol. 59, pp. 1198-1207 (2006).
Shoji, et al.; "Current Status of Delivery Systems to Improve Target Efficacy of Oligonucleotides"; Current Pharmaceutical Design; vol. 10, pp. 785-796 (2004).
Verma, et al.; "Gene therapy—promises, problems and prospects"; Nature; vol. 389, pp. 239-242 (Sep. 1997).
Chow, et al.; "High-performance genetically targetable optical neural silencing by light-driven proton pumps"; Nature; vol. 463, pp. 98-102 (Jan. 7, 2010).
Gong, et al.; "Enhanced Archaerhodopsin Fluorescent Protein Voltage Indicators"; PLOS One; vol. 8, Issue 6, 10 pages (Jun. 2013).
Han, et al.; "A high-light sensitivity optical neural silencer: development and application to optogenetic control of non-human primate cortex"; Frontiers in Systems Neuroscience; vol. 5, Article 18, pp. 1-8 (Apr. 2011).
Jones, et al.; "Animal Models of Schizophrenia"; British Journal of Pharmacology; vol. 164, pp. 1162-1194 (2011).
Definition of Implant; Merriam-Webster Dictionary; retrieved Nov. 7, 2016 (http://www.merriam-webster.com/dictionary/implant).
Ferenczi, et al.; "Optogenetic approaches addressing extracellular modulation of neural excitability"; Scientific Reports; vol. 6, 20 pages (Apr. 5, 2016).
Li, et al.; "A Method for Activation of Endogenous Acid-sensing Ion Channel 1 a (ASIC1a) in the Nervous System with High Spatial and Temporal Precision"; The Journal of Biological Chemistry; vol. 289, No. 22, pp. 15441-15448 (May 30, 2014).

(56) References Cited

OTHER PUBLICATIONS

Shimizu, et al.; "NMDA Receptor-Dependent Synaptic Reinforcement as a Crucial Process for Memory Consolidation"; Science; vol. 290, pp. 1170-1174 (Nov. 10, 2000).
Zeng, et al.; "Activation of acid-sensing ion channels by localized proton transient reveals their role in proton signaling"; Scientific Reports; vol. 5, 14 pages (Sep. 15, 2015).
Zeng, et al.; "Proton production, regulation and pathophysiological roles in the mammalian brain"; Neuroscience Bulletin; vol. 28, No. 1, pp. 1-13 (Feb. 1, 2012).
Definition of integral. Merriam-Webster Dictionary, retrieved on Mar. 20, 2017; Retrieved from the internet: <http://www.merriam-webster.com/dictionary/integral>.
Davidson, et al.; "Viral Vectors for Gene Delivery to the Nervous System"; Nature Reviews Neuroscience; vol. 4, pp. 353-364 (May 2003).
Fanselow, et al.; "Why We Think Plasticity Underlying Pavlovian Fear Conditioning Occurs in the Basolateral Amygdala"; Neuron; vol. 23, pp. 229-232 (Jun. 1999).
Rogers, et al.; "Effects of ventral and dorsal CA1 subregional lesions on trace fear conditioning"; Neurobiology of Learning and Memory; vol. 86, pp. 72-81 (2006).
Abbott, et al.; "Photostimulation of Retrotrapezoid Nucleus Phox2b-Expressing Neurons In Vivo Produces Long-Lasting Activation of Breathing in Rats"; The Journal of Neuroscience; vol. 29, No. 18, pp. 5806-5819 (May 6, 2009).
Alilain, et al.; "Light-Induced Rescue of Breathing after Spinal Cord Injury"; The Journal of Neuroscience; vol. 28, No. 46, pp. 11862-11870 (Nov. 12, 2008).
Cardin, et al.; "Targeted optogenetic stimulation and recording of neurons in vivo using cell-type-specific expression of Channelrhodopsin-2"; Nature Protocols; vol. 5, No. 2, pp. 247-254 (2010).
Caro, et al.; "Engineering of an Artificial Light-Modulated Potassium Channel"; PLoS One; vol. 7, Issue 8, e43766 (Aug. 2012).
Coleman, et al.; "Assessing Anxiety in Nonhuman Primates"; Ilar Journal; vol. 55, No. 2, pp. 333-346 (2014).
Hagglund, et al.; "Activation of groups of excitatory neurons in the mammalian spinal cord or hindbrain evokes locomotion"; Nature Neuroscience; vol. 13, No. 2, 8 pages (Feb. 2010).
Kleinlogel, et al.; "A gene-fusion strategy for stoichiometric and co-localized expression of light-gated membrane proteins"; Nature Methods; vol. 8, No. 12, pp. 1083-1091 (Dec. 2011).
Kravitz, et al.; "Regulation of parkinsonian motor behaviours by optogenetic control of basal ganglia circuitry"; Nature; vol. 466, No. 622, 8 pages (Jul. 29, 2010).
Luo, et al.; "Synthetic DNA delivery systems"; Nature Biotechnology; vol. 18, pp. 33-37 (Jan. 2000).
Maestripieri, et al.; "A modest proposal: displacement activities as an indicator of emotions in primates"; Anim. Behav.; vol. 44, pp. 967-979 (1992).
Nelson, et al.; "Non-Human Primates: Model Animals for Developmental Psychopathology"; Neuropsychopharmacology; vol. 34, No. 1, pp. 90-105 (Jan. 2009).
Tomita, et al.; "Visual Properties of Transgenic Rats Harboring the Channelrhodopsin-2 Gene Regulated by the Thy-1.2 Promoter"; PLoS One; vol. 4, No. 11, 13 pages (Nov. 2009).
Uniprot Accession No. P02945, integrated into the database on Jul. 21, 1986.
Johnson, et al.; "Differential Biodistribution of Adenoviral Vector In Vivo as Monitored by Bioluminescence Imaging and Quantitative Polymerase Chain Reaction"; Human Gene Therapy; vol. 17, pp. 1262-1269 (Dec. 2006).
Schester, et al.; "Biodistribution of adeno-associated virus serotype 9 (AAV9) vector after intrathecal and intravenous delivery in mouse"; Frontiers in Neuroanatomy; vol. 8, Article 42, pp. 1-41 (Jun. 10, 2014).
Gritton, et al.; "Optogenetically-evoked cortical cholinergic transients in mice expressing channelrhodopsin-2 (ChR2) in cholinergic neurons"; Society for Neuroscience Abstract Viewer and Itinery Planner & 40th Annual Meeting of the Society-for-Neuroscience; vol. 40, 2 pages (2010).
Sofuoglu, et al.; "Cholinergic Functioning in Stimulant Addiction: Implications for Medications Development"; CNS Drugs; vol. 23, No. 11, pp. 939-952 (Nov. 1, 2009).
Witten, et al.; "Cholinergic interneurons of the nucleus accumbens control local circuit activity and reward behavior"; Society for Neuroscience Abstract Viewer and Itinerary Planner & 40th Annual Meeting of the Society-for-Neuroscience; vol. 40, 2 pages (2010).
Azizgolshani, et al.; "Reconstituted plant viral capsids can release genes to mammalian cells"; Virology; vol. 441, No. 1, pp. 12-17 (2013).
Racaniello; "How many viruses on Earth?"; Virology Blog; 6 pages; http://www.virology.ws/2013/09/06/how-many-viruses-on-earth/ (Sep. 6, 2013).
Gerits, et al.; "Optogenetically Induced Behavioral and Functional Network Changes in Primates"; Current Biology; vol. 22, pp. 1722-1726 (Sep. 25, 2012).
Han, et al.; "Optogenetics in the nonhuman primate"; Prog. Brain Res.; vol. 196, pp. 215-233 (2012).
Daniel, et al.; "Stress Modulation of Opposing Circuits in the Bed Nucleus of the Stria Terminalis"; Neuropsychopharmacology Reviews; vol. 41, pp. 103-125 (2016).
Hammack, et al.; "The response of neurons in the bed nucleus of the stria terminalis to serotonin Implications for anxiety"; Progress in Neuro-Psychopharmacology & Biological Psychiatry; vol. 33, pp. 1309-1320 (2009).
Knopfel, et al.; "Remote control of cells"; Nature Nanotechnology; vol. 5, pp. 560-561 (Aug. 2010).
Steimer; "The biology of fear- and anxiety-related behaviors"; Dialogues in Clinical Neuroscience; vol. 4, No. 3, pp. 231-249 (Sep. 2002).
Stuber; "Dissecting the neural circuitry of addiction and psychiatric disease with optogenetics"; Neuropsychopharmacology; vol. 35, No. 1, pp. 341-342 (2010).
Tsuchida; "Nervous Control of Micturition"; The Japanese Journal of Urology; vol. 80, No. 9, pp. 1257-1277 (1989).
Boyden, et al.; "A history of optogenetics: the development of tools for controlling brain circuits with light"; F1000 Biology Reports; vol. 3, No. 11, 12 pages (May 3, 2011).
Knox, et al.; "Heterologous Expression of *Limulus* Rhodopsin"; The Journal of Biological Chemistry; vol. 278, No. 42, pp. 40493-40502 (Oct. 17, 2003).
Lin, et al.; "Characterization of Engineered Channelrhodopsin Variants with Improved Properties and Kinetics"; Biophysical Journal; vol. 96, No. 5, pp. 1803-1814 (Mar. 2009).
Bibel, et al.; "Differentiation of mouse embryonic stem cells into a defined neuronal lineage"; Nature Neuroscience; vol. 7, No. 9, pp. 1033-1009 (Sep. 2004).
Lin, et al.; "Study of the Circuitry of Nucleus Accumbens and its Effect on Addiction by Optogenetic Methods: 964"; Neurosurgery; vol. 67, No. 2, p. 557 (Aug. 2010).
Friedman, et al.; "VTA Dopamine Neuron Bursting is Altered in an Animal Model of Depression and Corrected by Desipramine"; J. Mol. Neurosci.; vol. 34, pp. 201-209 (2008).
Hackmann, et al.; "Static and time-resolved step-scan Fourier transform infrared investigations of the photoreaction of halorhodopsin from Natronobacterium pharaonis: consequences for models of the anion translocation mechanism"; Biophysical Journal; vol. 81, pp. 394-406 (Jul. 2001).
Weiss, et al.; "Galanin: A Significant Role in Depression?"; Annals New York Academy of Sciences; vol. 863, No. 1, pp. 364-382 (1998).
Winter, et al.; "Lesions of dopaminergic neurons in the substantia nigra pars compacta and in the ventral tegmental area enhance depressive-like behavior in rats"; Behavioural Brain Research; vol. 184, pp. 133-141 (2007).
Smith, et al.; "Proton binding sites involved in the activation of acid-sensing ion channel ASIC2a"; Neuroscience Letters; vol. 426, pp. 12-17 (2007).

(56) References Cited

OTHER PUBLICATIONS

Kugler, et al.; "Neuron-Specific Expression of Therapeutic Proteins: Evaluation of Different Cellular Promoters in Recombinant Adenoviral Vectors"; Molecular and Cellular Neuroscience; vol. 17, pp. 78-96 (2001).

Masaki, et al.; "(β-Adrenergic Receptor Regulation of the Cardiac L-Type Ca2+ Channel Coexpressed in a Fibroblast Cell Line"; Receptor; vol. 5, pp. 219-231 (1996).

* cited by examiner

CONTROL AND CHARACTERIZATION OF MEMORY FUNCTION

CROSS-REFERENCE TO RELATED APPLICATIONS

This application claims the priority benefit of U.S. Provisional Patent Application Nos. 61/410,732 filed on Nov. 5, 2010, and 61/540,926, filed on Sep. 29, 2011, the contents of each of which are incorporated herein by reference in their entirety.

BACKGROUND

The consolidation of remote memories relies on both synaptic consolidation processes on the timescale of minutes to hours, and circuit consolidation over weeks to years (Frankland and Bontempi, 2005; Squire and Bayley, 2007). The process of long-term contextual fear memory consolidation requires early involvement of the hippocampus, followed by the neocortex; in the course of this process, an influence of hippocampus on neocortex may enable the hippocampus to facilitate the long-term cortical storage of memory, rather than stably store the memory itself. Studies have shown that hippocampal lesions impair recent memory one day after training, but the same lesions had no effect on remote memory, several weeks after training (Anagnostaras et al., 1999; Bontempi et al., 1999; Debiec et al., 2002; Frankland et al., 2004; Kim and Fanselow, 1992; Kitamura et al., 2009; Maren et al., 1997; Maviel et al., 2004; Shimizu et al., 2000; Wang et al., 2003; Winocur et al., 2009). Additional studies suggest that both hippocampal and cortical memories are in continuous interplay.

Previous work on the circuitry of memory has involved physical, pharmacological and genetic lesion studies, which have greatly enhanced our understanding of neural systems but also have suffered from certain well-known challenges; for example, physical lesions are highly effective but lack both cellular and temporal precision, and other methods typically involve tradeoffs between cellular and temporal precision. Elegant genetic interventions can be cell-type specific (McHugh et al., 2007; Nakashiba et al., 2008), but are slow on the timescale of days. Pharmacological lesions enable higher temporal resolution on the timescale of minutes (Kitamura et al., 2009; Wiltgen et al., 2010), but are still slower than neurons and not typically cell-specific. There is a need for developing methods and tools that enable both cell-type precision and temporal control on the millisecond timescale for the study of memory in animals.

Various psychiatric conditions may arise due to a disorder in the circuitry of memory. For example, amnesia (e.g., non-graded, graded retrograde, focal retrograde amnesia, etc.) involves an inability to retrieve certain memories, while post traumatic stress disorder (PTSD) involves undesired retrieval of fearful memories. PTSD is a common debilitating psychiatric condition in which a single exposure to a traumatic event can lead to years of compromised function due to repeated re-experiencing of the trauma. Understanding the neural pathways that underlie undesired memory recall may help aid in the discovery and screening of pharmacological therapies to treat patients with such memory disorders.

All references cited herein, including patent applications and publications, are incorporated by reference in their entirety.

SUMMARY

Aspects of the present disclosure relates to control or characterization of memory function in living animals, as described herein. While the present disclosure is not necessarily limited in these contexts, embodiments of the invention may be appreciated through a discussion of examples using these and other contexts.

Certain embodiments of the present disclosure are directed toward specially-targeted circuits that are associated with memory function. More particular embodiments relate to spatio-temporal control over neural circuitry to identify specific circuit targets associated and corresponding with memory function(s) (e.g., memory formation and/or retrieval).

Particular embodiments of the present disclosure are directed toward temporally precise inhibition of neural circuits in the hippocampus (such as the neurons of the dorsal CA1 field of the hippocampus), the precision being sufficient to disrupt memory function. It has been discovered that temporal precision of neural inhibition is effective to disrupt remote memory retrieval, whereas prolonged inhibition has no significant effect on remote memory retrieval. Accordingly, aspects of the present disclosure relate to temporal aspects of such inhibition. Alternatively or additionally, methods for reversibly affecting memory function may comprise temporarily inhibiting neurons of the amygdala (e.g. basolateral amygdala) and/or neurons of the cingulate cortex (e.g., anterior cingulated cortex). In certain embodiments, this inhibition is performed using an optogenetic system that involves the expression of light-activated proteins (e.g., opsins) in the cells of the neural circuit. In other embodiments, the inhibition can be performed using direct electrical stimulus. Still other embodiments allow for the use of temporally-precise pharmaceuticals.

Various embodiments of the present disclosure relate to an optogenetic system or method that correlates temporal control over a neural circuit with measurable metrics. For instance, a particular memory function might be associated with a neurological disorder. The optogenetic system targets a neural circuit within an individual for selective control thereof. The optogenetic system involves monitoring the individual for metrics (e.g., symptoms) associated with the neurological disorder. In this manner the optogenetic system can provide detailed information about the neural circuit, its function and/or the neurological disorder. One or more methods for reversibly affecting memory function may be used to evaluate the effectiveness of pharmacological agents in treating PTSD and/or various memory disorders.

Provided herein are methods for affecting memory using optogenetic techniques by expressing light-activated proteins in a specific population of neurons involved in memory function, and affecting memory function by activating the protein by light. In some variations, the light-activated proteins may be configured to inhibit depolarization of a neuron in the presence of light having a specific wavelength. In some variations, the light-activated proteins may be configured to promote depolarization of a neuron in the presence of a light having a specific wavelength.

Provided herein is a non-human animal comprising a light-activated protein expressed on the cell membrane of excitatory neurons in the dorsal CA1 field of the hippocampus of the animal, wherein the protein is responsive to light and is capable of inhibiting depolarization of the neurons when the neurons are illuminated with the light, wherein the illumination of the protein reversibly affects memory function. Also provided herein is a non-human animal comprising a light-activated protein expressed on the cell membrane of excitatory neurons in the anterior cingulated cortex of the animal, wherein the protein is responsive to light and is capable of inhibiting depolarization of the neurons when the neurons are illuminated with the light, wherein the illumination of the protein reversibly affects memory function. Also provided herein is a non-human animal comprising a light-activated protein expressed on the cell membrane of excitatory neurons in the basolateral amygdala of the animal, wherein the protein is responsive to light and is capable of inhibiting depolarization of the neurons when the neurons are illuminated with the light, wherein the illumination of the protein reversibly affects memory function. In some embodiments, the memory function that is affected when the neurons are illuminated may be memory retrieval and/or memory formation. In some embodiments, the memory is a fearful memory and/or a remote memory.

Also provided herein is a brain tissue slice comprising a brain region selected from the group consisting of the dorsal CA1 field of the hippocampus, the basolateral amygdala, and the anterior cingulated cortex, wherein a light-activated protein is expressed on the cell membrane of excitatory neurons of the brain region, wherein the protein is responsive to light and is capable of inhibiting depolarization of the neurons when the neurons are illuminated with the light, wherein the illumination of the protein reversibly affects memory function.

Also provide herein are methods of reversibly affecting memory retrieval or formation in an individual.

In some embodiments, the method for reversibly affecting memory retrieval or formation in an individual comprises: administering a polynucleotide encoding a light-activated protein to the dorsal CA1 field of the hippocampus in the individual, wherein light-activated protein is expressed on the cell membrane of the excitatory neurons in the dorsal CA1 field of the hippocampus and the protein is responsive to light and is capable of inhibiting depolarization of the neurons when the neurons are illuminated with the light, whereby activating the protein by the light reversibly affects memory retrieval or formation of an event in the individual. In some embodiments, the method for reversibly affecting memory retrieval or formation comprises: inhibiting depolarization of excitatory neurons in the dorsal CA1 field of the hippocampus during memory retrieval or formation of an event in an individual, wherein a light-activated protein is expressed on the cell membrane of the excitatory neurons in the dorsal CA1 field of the hippocampus of the individual, wherein the protein is responsive to light and is capable of inhibiting depolarization of the neurons when the neurons are illuminated with the light.

In some embodiments, the method for reversibly affecting memory retrieval or formation in an individual comprises: administering a polynucleotide encoding a light-activated protein to the anterior cingulated cortex in the individual, wherein light-activated protein is expressed on the cell membrane of the excitatory neurons in the anterior cingulated cortex and the protein is responsive to light and is capable of inhibiting depolarization of the neurons when the neurons are illuminated with the light, whereby activating the protein by the light reversibly affects memory retrieval or formation of an event in the individual. In some embodiments, the method for reversibly affecting memory retrieval or formation comprises: inhibiting depolarization of excitatory neurons in the anterior cingulated cortex during memory retrieval or formation of an event in an individual, wherein a light-activated protein is expressed on the cell membrane of the excitatory neurons in the anterior cingulated cortex of the individual, wherein the protein is responsive to light and is capable of inhibiting depolarization of the neurons when the neurons are illuminated with the light.

In some embodiments, the method for reversibly affecting memory retrieval or formation in an individual comprises: administering a polynucleotide encoding a light-activated protein to the basolateral amygdala in the individual, wherein light-activated protein is expressed on the cell membrane of the excitatory neurons in the basolateral amygdala and the protein is responsive to light and is capable of inhibiting depolarization of the neurons when the neurons are illuminated with the light, whereby activating the protein by the light reversibly affects memory retrieval or formation of an event in the individual. In some embodiments, the method for reversibly affecting memory retrieval or formation comprises: inhibiting depolarization of excitatory neurons in the basolateral amygdala during memory retrieval or formation of an event in an individual, wherein a light-activated protein is expressed on the cell membrane of the excitatory neurons in the basolateral amygdala of the individual, wherein the protein is responsive to light and is capable of inhibiting depolarization of the neurons when the neurons are illuminated with the light.

Also provided herein are methods for treating post-traumatic stress disorder in an individual. In some embodiments, the method for treating post-traumatic stress disorder in an individual comprises: administering a polynucleotide encoding a light-activated protein to the dorsal CA1 field of the hippocampus in the individual, wherein light-activated protein is expressed on the cell membrane of the excitatory neurons in the dorsal CA1 field of the hippocampus and the protein is responsive to light and is capable of inhibiting depolarization of the neurons when the neurons are illuminated with the light, whereby activating the protein by the light reversibly affects memory retrieval or formation of an event in the individual. In some embodiments, the method for treating post-traumatic stress disorder in an individual comprises: administering a polynucleotide encoding a light-activated protein to the anterior cingulated cortex in the individual, wherein light-activated protein is expressed on the cell membrane of the excitatory neurons in the anterior cingulated cortex and the protein is responsive to light and is capable of inhibiting depolarization of the neurons when the neurons are illuminated with the light, whereby activating the protein by the light reversibly affects memory retrieval or formation of an event in the individual.

Also provided herein are methods of screening a pharmacological agent that affects memory retrieval or formation comprising: a) contacting excitatory neurons in the dorsal CA1 field of the hippocampus during memory retrieval or formation of an event in a non-human animal with a pharmacological agent, wherein the non-human animal comprises a light-activated protein expressed on the cell membrane of excitatory neurons in the dorsal CA1 field of the hippocampus of the animal, wherein the protein is responsive to light and is capable of inhibiting depolarization of the neurons when the neurons are illuminated with the light; b) inhibiting depolarization of the excitatory neurons in the dorsal CA1 field of the hippocampus during memory retrieval or formation of an event; and c) determining if the pharmacological agent affects memory retrieval or formation in the presence or absence of the light. Also provided herein are methods of screening a pharmacological agent that affects memory retrieval or formation comprising: a) contacting excitatory neurons in the anterior cingulated cortex during memory retrieval or formation of an event in a non-human animal with a pharmacological agent, wherein the non-human animal comprises a light-activated protein expressed on the cell membrane of excitatory neurons in the anterior cingulated cortex of the animal, wherein the protein is responsive to light and is capable of inhibiting depolarization of the neurons when the neurons are illuminated with the light; b) inhibiting depolarization of the excitatory neurons in the anterior cingulated cortex during memory retrieval or formation of an event; and c) determining if the pharmacological agent affects memory retrieval or formation in the presence or absence of the light. Also provided herein are methods of screening a pharmacological agent that affects memory retrieval or formation comprising: a) contacting excitatory neurons in the basolateral amygdala during memory retrieval or formation of an event in a non-human animal with a pharmacological agent, wherein the non-human animal comprises a light-activated protein expressed on the cell membrane of excitatory neurons in the basolateral amygdala of the animal, wherein the protein is responsive to light and is capable of inhibiting depolarization of the neurons when the neurons are illuminated with the light; b) inhibiting depolarization of the excitatory neurons in the basolateral amygdala during memory retrieval or formation of an event; and c) determining if the pharmacological agent affects memory retrieval or formation in the presence or absence of the light.

The light-activated protein may be responsive to light and configured such that the protein is capable of inhibiting depolarization of the neurons when the neurons are illuminated with the light. In some embodiments, the light-activated protein may be selected from the group consisting of NpHR, BR, AR, and GtR3 described herein. In some embodiments, the light-activated protein is a NpHR protein comprising an amino acid sequence at least 95%, at least 96%, at least 97%, at least 98%, at least 99% or 100% identical to the sequence shown in SEQ ID NO:3. In some embodiments, the NpHR protein further comprises an endoplasmic reticulum (ER) export signal and/or a membrane trafficking signal. For example, the NpHR protein comprises an amino acid sequence at least 95% identical to the sequence shown in SEQ ID NO:3 and an endoplasmic reticulum (ER) export signal. In some embodiments, the amino acid sequence at least 95% identical to the sequence shown in SEQ ID NO:3 is linked to the ER export signal through a linker. In some embodiments, the ER export signal comprises the amino acid sequence FXYENE (SEQ ID NO:8), where X can be any amino acid. In another embodiment, the ER export signal comprises the amino acid sequence VXXSL, where X can be any amino acid. In some embodiments, the ER export signal comprises the amino acid sequence FCYENEV (SEQ ID NO:9). In some embodiments, the NpHR protein comprises an amino acid sequence at least 95% identical to the sequence shown in SEQ ID NO:3, an ER export signal, and a membrane trafficking signal. In other embodiments, the NpHR protein comprises, from the N-terminus to the C-terminus, the amino acid sequence at least 95% identical to the sequence shown in SEQ ID NO:3, the ER export signal, and the membrane trafficking signal. In other embodiments, the NpHR protein comprises, from the N-terminus to the C-terminus, the amino acid sequence at least 95% identical to the sequence shown in SEQ ID NO:3, the membrane trafficking signal, and the ER export signal. In some embodiments, the membrane trafficking signal is derived from the amino acid sequence of the human inward rectifier potassium channel Kir2.1. In some embodiments, the membrane trafficking signal comprises the amino acid sequence K S R I T S E G E Y I P L D Q I D I N V (SEQ ID NO:10). In some embodiments, the membrane trafficking signal is linked to the amino acid sequence at least 95% identical to the sequence shown in SEQ ID NO:3 by a linker. In some embodiments, the membrane trafficking signal is linked to the ER export signal through a linker. The linker may comprise any of 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the light-activated protein further comprises an N-terminal signal peptide. In some embodiments, the light-activated protein comprises the amino acid sequence of SEQ ID NO:5. In some embodiments, the light-activated protein comprises the amino acid sequence of SEQ ID NO:6.

It is to be understood that one, some, or all of the properties of the various embodiments described herein may be combined to form other embodiments of the present invention. These and other aspects of the invention will become apparent to one of skill in the art.

BRIEF DESCRIPTION OF THE DRAWINGS

FIG. 4A shows that double lentiviral injection resulted in eNpHR3.1 expression throughout the CA1 only. FIG. 4B shows that eNpHR3.1 is expressed in the neuronal membrane around the soma, as well as in the apical and basal dendrites of CA1 neurons. FIG. 4C depicts data demonstrating that CaMKIIα::eNpHR3.1 was expressed in 94% (458/486 cells, from 3 mice) of CA1 pyramidal neurons, with 100% specificity (all eNpHR3.1-EYFP cells were CaMKIIα positive). FIG. 4D depicts data from in-vivo 'optrode' light administration and recording performed by inserting an optic fiber coupled to a tungsten electrode to the CA1 in anesthetized mice expressing eNpHR3.1 (left). 561 nm illumination of CA1 neurons in these mice resulted in a reversible, marked reduction in spiking frequency (4.93±1.6 Hz, 1.31±0.15 Hz, and 6.45±2.4 Hz; before, during and after light administration, respectively, in 15 traces from 2 mice, $P<0.02$), without affecting average spike amplitude (33.55±4.94 µV, 29.20±4.4 µV, and 33.32±5.45 µV; before, during and after light). A representative optrode recording trace, as well as average frequency and amplitude are shown (mean±SEM).

FIG. 5A shows that bilateral in-vivo light may be administered to CA1 by inserting a double optic fiber through bilateral cannula guide in freely-moving mice. FIG. 5B (top) depicts an experimental sequence where continuous 561 nm illumination was administered during fear-conditioning training, and mice were tested for their memory 24 hr later without light. One day later, mice were re-trained without light, and re-tested without light on the fourth day and with light on the fifth. (bottom) CA1 optogenetic inhibition during fear-conditioning training (Light ON) prevented acquisition in eNpHR3.1 mice (n=5) compared to controls (n=4) (39±5.4 vs. 7.6±4.3% freezing; means±SEM, $P<0.005$). When re-trained without illumination (Light OFF), the same mice demonstrated intact contextual memory (64.6±6.6 vs. 49.7±11.7% freezing; P>0.5). This contextual fear memory became unavailable for recall upon light administration during testing (light ON) in eNpHR3.1 mice (42.6±10.1 vs. 5.94±4.1% freezing, P<0.01). FIG. 5C shows that CA1 optogenetic inhibition had no effect on either acquisition (left) or recall (right) of the hippocampal-independent auditory-cued fear memory in eNpHR3.1 mice (n=5) compared to controls (n=4). FIG. 5D depicts data showing optogenetic inhibition had no effect on exploration of the context before conditioning in eNpHR3.1 mice (n=5) compared to controls (n=4). CA1 optogenetic inhibition also had no effect on exploration of a novel environment. FIGS. 5E and 5F show that control (n=6) and eNpHR3.1 (n=4) mice explored the field with similar path lengths (564±9 and 618±114 cm, respectively) and similar speeds (3.3±0.1 vs. 3.43±0.6 cm/sec, respectively). FIG. 5G shows that there was no effect on anxiety, as the percent of time that control and eNpHR3.1 mice spent in the center of the open field was similar (23.8±12.76% vs. 20.46±5.97%, P>0.5). Representative exploration traces are presented. FIG. 5H depicts eNpHR3.0 expression in basolateral amygdala (BLA). FIG. 5I shows that light administration to the BLA resulted in impaired contextual (65.5±7.2 vs. 9.6±5.5% freezing; P<0.001) and cued (69.5±9.6 vs. 24.5±13% freezing; P<0.05) memory acquisition in eNpHR3.0 (n=4) mice, compared to controls (n=9).

FIG. 6A depicts data indicating that CA1 optogenetic inhibition reversibly prevented recall of remote memory that was acquired 28 days earlier, and was never previously evoked (P<0.0001; Control n=14, 69.8±5.3% freezing eNpHR3.1 n=6, 14±6.4% freezing). This recall disruption was reversible, as when the same mice were re-introduced to the conditioning context on the next day with no illumination they demonstrated intact fear responses (52.45±6.0 vs. 45.18±11.5% freezing; P>0.5). FIG. 6B depicts data showing that auditory-cued fear, tested 28 days after conditioning was not affected (Control n=14, 22.3±6.8%, eNpHR3.1 n=6, 11.8±3.5% freezing in the new context; and 72.4±8.4 vs. 58.77±7.9% freezing to the tone; P>0.5). FIG. 6C shows that CA1 optogenetic inhibition impaired recall of ultra remote memory that was acquired 63 days earlier, and was never previously evoked (P<0.005; Control n=9, 31.8±3.8% freezing eNpHR3.1 n=6, 11.3±3.6% freezing). FIG. 6D depicts data showing that pharmacological hippocampal inhibition by TTX and CNQX administration one day after conditioning prevented recent fear recall (Saline n=5, 56.86±1.9% freezing; TTX+CNQX n=4, 26.05±10.23% freezing; P<0.05). FIG. 6E shows that TTX and CNQX administration one month after conditioning did not affect remote fear recall (Saline n=8, 93.93±2.54% freezing; TTX+CNQX n=9, 83.8±4.4% freezing; P>0.05).

FIG. 7A shows that CA1 optogenetic inhibition prevents remote fear recall of a memory that was acquired 28 days earlier, only when the light was administered precisely during testing (Precise group, Control n=4, 72.65±11.5% freezing, eNpHR3.1 n=8, 26.9±10.4% freezing; P<0.01), but not when the light was ON continuously for 30 min before, as well as during, the test (Prolonged group, middle, Control n=3, 70.13±12.2% freezing, eNpHR3.1 n=4, 67.7±5.6% freezing; P>0.05). When the prolonged group mice were re-tested the next day with light during the test only, their recall was disrupted (Prolonged group, left, 55.5±8.5 vs. 27.6±8.6% freezing; P<0.05). FIG. 7B shows that prolonged light prevents recall of recent memory, 24 hr after conditioning (Control n=7, 32.2±10.6% freezing, eNpHR3.1 n=3, 4±2.6% freezing; P<0.05). FIG. 7C shows that eNpHR3.1 continuously and completely prevented evoked spiking for 30 min, as shown in the recording trace. Detailed traces of sections 1 (inhibition onset) 2 (during continuous inhibition) and 3 (end of inhibition and recovery) are presented on the bottom left. Averaged percent successful evoked spiking before light, during light administration (after 5 min and 30 min of light ON) and recovery after light OFF are presented (bottom right; n=4 mice, 10 cells).

FIG. 9A depicts an experiment where mice were fear-conditioned under light delivery, and brains were collected 90 min after training. FIG. 9B shows brain slices stained for c-Fos and DAPI. Expression of YFP control and eNpHR3.1 are shown. The CA1 region from which these images were taken is marked by a white square in FIG. 9C. FIG. 9C depicts representative images of CA1, ACC and BLA. Anatomy is shown by DAPI nuclear staining, and the margins of the amygdala are marked with a dashed yellow line. White scalebar: 150 μm. FIG. 9D shows that CA1 optogenetic inhibition during FC reduced the expression of the neuronal activation marker c-Fos in CA1 (n=2 to 4 mice, 6 to 15 slices per group; P<0.01), but not in the ACC or BLA. In the BLA, activity levels were similarly elevated in both control and eNpHR3.1 mice (p<0.0001). FIG. 9E depicts an experiment where another group of mice was trained, and then re-exposed to the conditioning context 28 days after conditioning. Brains were collected for staining 90 min after testing. FIG. 9F depicts representative CA1, ACC and BLA images following remote memory are shown. White scalebar: 150 μm. FIG. 9G shows that remote recall 28 days following conditioning resulted in a small but significant increase in CA1 c-Fos expression in control mice (P<0.005), and highly increased activity levels in ACC (P<0.0001) and BLA (P<0.0001). Light inhibition during exposure to the context completely blocked CA1 activity (P<0.05), and significantly reduced ACC and BLA activity (P<0.0001 and P<0.0001, respectively), compared to control. FIG. 9H shows global patterns in brain activity between conditioning (day 0) and remote recall (day 28). Activity levels in CA1 significantly decreased in control (P<0.005) mice from day 0 to day 28. Activity levels in ACC significantly increased in both control (P<0.0001) and eNpHR3.1 (P<0.001) mice day 0 to day 28. Activity levels in BLA significantly increased in control (P<0.001) but not in eNHR3.1 mice.

FIG. 10A depicts eNpHR3.0 expression in the anterior cingulate cortex (ACC). FIG. 10B depicts an experiment where precise light administration resulted in inhibition of remote (Control n=5, 81.6±4.9% freezing; eNpHR3.0 n=5, 53.8±11% freezing; P<0.05), but not recent (75.9±5.4 vs. 76±2.9% freezing) memory recall. FIG. 10C depicts another experiment where prolonged light in ACC also resulted in inhibition of remote (Control n=3, 78.0±6.2% freezing; eNpHR3.0 n=8, 45.0±5.2% freezing; P<0.05), but not recent (78.5±12.7 vs. 74.3±4.3% freezing) memory recall.

DETAILED DESCRIPTION

Figure 1:
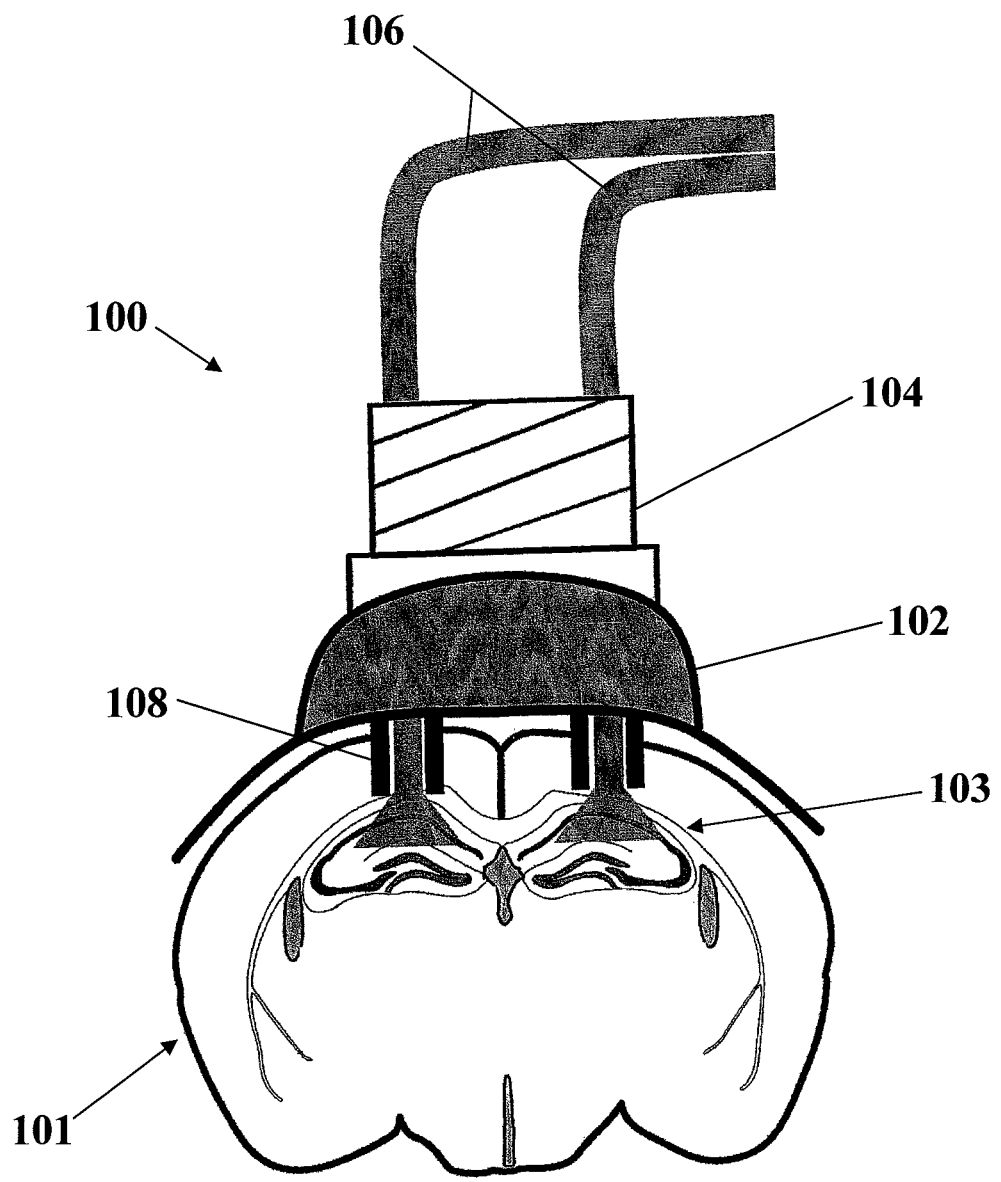
FIG. 1 depicts one variation of a device or a system that may be used to apply light of selected wavelengths to affect memory function.

The present disclosure is believed to be useful for modifying memory function on a temporal basis. Specific applications of the present invention facilitate disrupting memory retrieval and/or emotional responses linked to memory retrieval. As many aspects of the example embodiments disclosed herein relate to and significantly build on previous developments in this field, the following discussion summarizes such previous developments to provide a solid understanding of the foundation and underlying teachings from which implementation details and modifications might be drawn. It is in this context that the following discussion is provided and with the teachings in these references incorporated herein by reference. While the present invention is not necessarily limited to such applications, various aspects of the invention may be appreciated through a discussion of various examples using this context.

It has been discovered that (temporal) disruption of the dorsal CA1 hippocampus circuit is effective to prevent contextual fear memory acquisition. Consistent therewith, a prevailing neural network theory suggests that the process of memory consolidation starts with short-term modifications in the connections between the hippocampus and the cortex, which enable the hippocampus to activate the relevant cortical sites that contribute to the complete memory, rather than to store the memory itself. While these cortical traces are repeatedly co-activated, gradual long-lasting changes in the connections between them occur until eventually these connections are strong enough to support the memory without any hippocampal involvement.

Surprisingly, it has been discovered that the disruption of the dorsal CA1 hippocampus circuit is effective to block fear-memory recall, even after cortical reorganization is believed to have occurred.

Consistent with various embodiments of the present disclosure, methods, systems or devices are discussed that relate to controlling neural circuits. Control over the neural circuit can include inhibition or excitation, which can each include coordinated firing, and/or modified susceptibility to external circuit inputs. For instance, inhibition can be accomplished using a light-activated protein, such as an ion channel and/or ionic pump (e.g., NpHR and NpHR variants). Such ion channels move the membrane potential of the neuron away from its threshold voltage to dissuade or inhibit action potentials. In another instance, excitation can be accomplished using a light-activated protein, such as an ion channel (e.g., ChR2 and ChR2 variants). Such ion channels can cause the membrane potential to move toward and/or past the threshold voltage, thereby exciting or encouraging action potentials. Consistent with various embodiments, a light-activated protein can be used to (temporarily) shift the resting potential of a neuron to increase or decrease its susceptibility to external circuit inputs. These various options can also be used in combination.

The devices and methods provided herein may reversibly affect memory function. For example, the methods described below may be used to control and/or characterize the neural circuitry that underlies long-term and short-term memory, as well as various types of memories, including fearful or stressful memories. The methods may also affect various stages of memory function (e.g., memory acquisition, consolidation, and recall). In some variations for affecting memory function (e.g., such as memory formation and/or retrieval), memory function is affected by applying light to neurons of the dorsal CA1 region of the hippocampus, in the basolateral amygdala (BLA), and/or in the anterior cingulated cortex (ACC) that express light-activated proteins. In the presence of light, these light-activated proteins may inhibit depolarization of the neurons, thereby disturbing the formation and/or retrieval of memories. While the exemplary methods are described in the context of the acquisition and recall of contextual remote and recent fear-based memories, it should be understood that the devices and methods disclosed herein may be used to affect other stages of memory function, as well as other types of memories (e.g., cued memories).

Various embodiments described herein and shown in the figures may be implemented together and/or in other manners. One or more of the items depicted in the drawings/figures can also be implemented in a more separated or integrated manner, or removed and/or rendered as inoperable in certain cases, as is useful in accordance with particular applications. For example, embodiments involving the treatments for PTSD as discussed herein may be implemented using temporally-controlled drug release. In view of the description herein, those skilled in the art will recognize that many changes may be made thereto without departing from the spirit and scope of the present invention.

Expressing Light-Activated Proteins in Target Cells

The activity of a neuron (e.g., neurons involved in memory function) may be affected using a variety of mechanisms. Deterministic methods of affecting neuronal activity may be used to control and/or characterize the neural circuits that underlie various brain functions. For example, neuronal responses may be affected by applying pharmacological agents (e.g., tetrodotoxin (TTX), 6-cyano-7-nitroquinoxaline-2,3-dione (CNQX), picrotoxin, strychnine, etc.) and/or by electrical stimulation (e.g., electrodes). In some variations, neuronal activity may be affected by activating certain types of proteins on the membrane of the neuron, which may hyperpolarize or depolarize the cell membrane. For example, light-activated proteins that become permeable to certain ions (e.g., cations, anions) in the presence of light with a certain wavelength may be expressed in a neuron. Examples of light-activated proteins may include light-activated ion channels and/or pumps, which are further described below.

In some variations, microbial opsin genes may be adapted for uses in neuroscience. These opsins allow transduction of light pulse trains into millisecond-timescale membrane potential changes in specific cell types within the intact mammalian brain (e.g., channelrhodopsin (ChR2), Volvox channelrhodopsin (VChR1) and halorhodopsin (NpHR)). ChR2 is a rhodopsin derived from the unicellular green alga Chlamydomonas reinhardtii. The term "rhodopsin" as used herein is a protein that comprises at least two building blocks, an opsin protein, and a covalently bound cofactor, usually retinal (retinaldehyde). The rhodopsin ChR2 is derived from the opsin Channelopsin-2 (Chop2), originally named Chlamyopsin-4 (Cop4) in the Chlamydomonas genome. The temporal properties of one depolarizing channelrhodopsin, ChR2, include fast kinetics of activation and deactivation, affording generation of precisely timed action potential trains. For applications seeking long timescale activation, it has been discovered that the normally fast off-kinetics of the channelrhodopsins can be slowed. For example, certain implementations of channelrhodopsins apply 1 mW/mm$^2$ light for virtually the entire time in which depolarization is desired, which can be less than desirable.

Light-activated proteins that generate hyperpolarization or inhibit depolarization of the membrane in response to light with certain wavelength(s) may be expressed in the excitatory neurons (e.g., glutamatergic neurons) of the dorsal CA1 region of the hippocampus (CA1), basolateral amygdala (BLA), and anterior cingulated cortex (ACC) regions. Table 1 below shows various examples of light-activated proteins that may be expressed in the excitatory neurons to inhibit depolarization or hyperpolarize the neurons in the presence of light of a certain wavelength. Further description of these and other light-activated proteins may be found in PCT App. No. PCT/US11/028893, titled "LIGHT SENSITIVE ION PASSING MOLECULES", filed on Mar. 17, 2011, which is incorporated by reference in its entirety. As used herein, "NpHR", "BR", "AR", and "GtR3" include wild type proteins and functional variants (including naturally occurring variants).

TABLE 1

| Light-activated proteins | Biological Origin | Wavelength Sensitivity | Defined Action |
| --- | --- | --- | --- |
| NpHR | Natronomonas pharaonis | 680 nm utility (with 3.0 series) 589 nm max | Inhibition (hyperpolarization) |
| BR | Halobacterium helobium | 570 nm max | Inhibition (hyperpolarization) |
| AR | Acetabulaira acetabulum | 518 nm max | Inhibition (hyperpolarization) |
| GtR3 | Guillardia theta | 472 nm max | Inhibition (hyperpolarization) |

Embodiments of the present invention include relatively minor amino acid variants of the naturally occurring sequences. In one instance, the variants are greater than about 75% homologous to the protein sequence of the naturally occurring sequences. In other variants, the homology is greater than about 80%. Yet other variants have homology greater than about 85%, greater than 90%, or even as high as about 93% to about 95% or about 98%. Homology in this context means sequence similarity or identity, with identity being preferred. This homology can be determined using standard techniques known in the field of sequence analysis. The compositions of embodiments of the present invention include the protein and nucleic acid sequences provided herein, including variants which are more than about 50% homologous to the provided sequence, more than about 55% homologous to the provided sequence, more than about 60% homologous to the provided sequence, more than about 65% homologous to the provided sequence, more than about 70% homologous to the provided sequence, more than about 75% homologous to the provided sequence, more than about 80% homologous to the provided sequence, more than about 85% homologous to the provided sequence, more than about 90% homologous to the provided sequence, or more than about 95% homologous to the provided sequence.

Provided herein are non-human animals comprising a light-activated protein expressed on the cell membrane of excitatory neurons in the dorsal CA1 field of the hippocampus, anterior cingulated cortex, and/or basolateral amygdala of the animal, wherein the protein is responsive to light and is capable of inhibiting depolarization of the neurons when the neurons are illuminated with the light, wherein the illumination of the protein reversibly affects memory function. In some embodiments, the light-activated protein is selected from the group consisting of NpHR, BR, AR and GtR3 described herein. For example, any of the NpHR proteins described herein may be expressed on the cell membrane of the target neurons.

Also provided herein are brain tissue slices comprising a brain region selected from the group consisting of the dorsal CA1 field of the hippocampus, the basolateral amygdala, and the anterior cingulated cortex, wherein a light-activated protein is expressed on the cell membrane of excitatory neurons of the brain region, wherein the protein is responsive to light and is capable of inhibiting depolarization of the neurons when the neurons are illuminated with the light, wherein the illumination of the protein reversibly affects memory function. In some embodiments, the brain tissue slices are cultured tissue slices taken from the non-human animals described herein. In some embodiments, the light-activated protein is selected from the group consisting of NpHR, BR, AR and GtR3 described herein. For example, any of the NpHR proteins described herein may be expressed on the cell membrane of the target neurons.

In some embodiments, neurons of the CA1, BLA, and/or ACC regions may express ChR2. Unless otherwise stated, the invention includes a number of similar variants. Examples include, but are not limited to, Chop2, ChR2-310, Chop2-310, and Volvox channelrhodopsin (VChR1). For further details on VChR1, reference can be made to "Redshifted optogenetic excitation: a tool for fast neural control derived from Volvox carteri," Nat. Neurosci. June 2008, 11(6):631-3. Epub 2008 Apr. 23, which is fully incorporated herein by reference. In other implementations, similar modifications can be made to other opsin or light-activated molecules. For instance, modifications/mutations can be made to ChR2 or VChR1 variants. Moreover, the modified variants can be used in combination with light-activated ion pumps.

As used herein, stimulation of a target cell is generally used to describe modification of properties of the cell. For instance, the stimulus of a target cell may result in a change in the properties of the cell membrane that can lead to the depolarization or polarization of the target cell. In a particular instance, the target cell is a neuron and the stimulus may affect the transmission of impulses by facilitating or inhibiting the generation of impulses (action potentials) by the neuron.

For further details on light-activated proteins (e.g., opsins), reference can be made to PCT Publ. No. WO 2010/056970, entitled "OPTICALLY-BASED STIMULATION OF TARGET CELLS AND MODIFICATIONS THERETO," to Deisseroth et al., which is fully incorporated herein by reference.

Embodiments of the present disclosure are directed toward implementation of bistable changes in the excitability of targeted populations. This includes, but is not necessarily limited to, the double-mutant ChR2-C128S/D156A. This double-mutant ChR2-C128S/D156A has been found to be well-tolerated in cultured hippocampal neurons and preserved the essential SFO properties of rapid step-like activation with single brief pulses of blue light, and deactivation with green or yellow light. In particular, the activation spectrum of ChR2-C128S/D156A peaks at 445 nm. A second deactivation peak was found at 390-400 nm, with faster but less complete deactivation by comparison with the 590 nm deactivation peak. Peak photocurrents in cells expressing ChR2-C128S/D156A were found to be robust and comparable to those of ChR2-D156A (231.08±31.19 s.e.m; n=9 cells and 320.96±78.26 s.e.m; n=7 cells, respectively).

Individual transfected and patch-clamped neurons were next activated with 100 ms pulses of 470 nm light. To ensure over very long recordings that current decay would not be attributable to cell rundown, each cell was deactivated with prolonged 590 nm light pulses at distinct intervals to determine the magnitude of remaining SFO current at each time point. Surprisingly, neurons expressing ChR2-C128S/D156A gave rise to sustained photocurrents that were more stable than those from cells expressing either single mutant alone. Fitting a mono-exponential decay curve to the ratio of Ideactivation/Iactivation over time revealed a spontaneous decay time constant of 29.3 minutes for ChR2-C128S/D156A, indicating that the C128 and D156 mutations act synergistically to delay the decay of the open state of ChR2. Consistent with the required improvement for the anticipated application to complex mammalian behaviors, significant portions of the double-mutant SFO current were still present up to 20 minutes after the single photoactivation pulse.

Based on these surprisingly slow decay kinetics, the double-mutant gene is referred to as SSFO (for stabilized step-function opsin) gene. SSFO is also used as shorthand for the active protein. Both residues likely are involved in ChR2 channel closure (gating), and both mutations likely stabilize the open state configuration of the channel Without being limited by theory, aspects of the present disclosure relate to the discovery that SSFO may be completely blocked in photocycle progression, and may therefore represent the maximal stability possible with photocycle engineering. For instance, in contrast to ChR2 C128X and ChR2-D156A, the SSFO photocycle does not appear to access additional inactive deprotonated side products which likely split off the photocycle at later photocycle stages not reached in this mutant, in turn making the SSFO even more reliable for repeated use in vivo than the parental single mutations.

Embodiments of the present disclosure are directed toward the sensitivity of the SSFO to light. For instance, channelrhodopsins with slow decay constants effectively act as photon integrators. This can be particularly useful for more-sensitive, less-invasive approaches to optogenetic circuit modulation, still with readily titratable action on the target neuronal population via modulation of light pulse length. It has been discovered that, even at extraordinarily low light intensities (as low as 8 µW mm$^{-2}$), hundreds of picoamps of whole-cell photocurrents could be obtained from neurons expressing SSFO, which increased with monoexponential kinetics in response to 470 nm light during the entire time of illumination. Other aspects relate to the use of activation time constants that are linearly correlated with the activation light power on a log-log scale, which is indicative of a power-law relationship and suggesting that the SSFO is a pure integrator, with total photon exposure over time as the only determinant of photocurrent. For instance, it is believed that the number of photons per membrane area required for photocurrents to reach a given sub-maximal activation (time to τ) is constant regardless of activation light power.

Example embodiments of the present disclosure relate to the use of a hybrid ChRI/VChRI chimera, which contains no ChR2 sequence at all and is derived from two opsins genes that do not express well individually, and is herein referred to as C1V1. Embodiments of the present disclosure also relate to improvements of the membrane targeting of VChR1 through the addition of a membrane trafficking signal derived from the K$_{ir}$2.1 channel. Confocal images from cultured neurons expressing VChR1-EYFP revealed a large proportion of intracellular protein compared with ChR2; therefore, to improve the membrane targeting of VChR1, we added a membrane trafficking signal derived from the Kir2.1 channel. Membrane targeting of this VChR1-ts-EYFP was slightly enhanced compared with VChR1-EYFP; however, mean photocurrents recorded from cultured hippocampal neurons expressing VChR1-ts-EYFP were only slightly larger than those of VChR1-EYFP. Accordingly, embodiments of the present disclosure relate VChR1 that is modified by exchanging helices with corresponding helices from other ChR5. For example, robust improvement has been discovered in two chimeras where helices 1 and 2 were replaced with the homologous segments from ChR1. It was discovered that whether splice sites were in the intracellular loop between helices 2 and 3 (at ChR1 residue Ala145) or within helix 3 (at ChR1 residue Trp163), the resulting chimeras were both robustly expressed and showed similarly enhanced photocurrent and spectral properties. This result was unexpected as ChR1 is only weakly expressed and poorly integrated into membranes of most mammalian host cells. The resulting hybrid ChR1/VChR1 chimera is herein referred to as C1V1.

Aspects of the present disclosure relate to the expression of C1V1 in cultured neurons (e.g., hippocampal neurons). Experimental tests have shown a number of surprising and useful results, which are discussed in more detail hereafter. C1V1-EYFP exhibits surprisingly improved average fluorescence compared with VChR1-EYFP. Whole cell photocurrents in neurons expressing C1V1 were much larger than those of VChR1-EYFP and VChR1-ts-EYFP, and ionic selectivity was similar to that of ChR2 and VChR1. The addition of the Kir2.1 trafficking signal between C1V1 and YFP further enhanced photocurrents by an additional 41%. (C1V1-ts-EYFP mean photocurrents were extremely large, nearly tenfold greater than wild type (WT) VChR1). Mean fluorescence levels closely matched the measured photocurrents (mean fluorescence 9.3±1, 19.6±3.4, 19.8±2.8 and 36.3±3.8 for VChR1-EYFP, VChR1-ts-EYFP, C1V1-EYFP and C1V1-ts-EYFP, respectively), suggesting that the increase in photocurrent sizes resulted mainly from the improved expression of these channels in mammalian neurons. Total somatic fluorescence (measured as integrated pixel density) was linearly correlated with photocurrent size in individual recorded/imaged cells across the different constructs (VChR1, VChR1-ts-EYFP, C1V1, C1V1-ts-EYFP). This suggests (without being limited by theory) that the increased photocurrent of C1V1 results from functional expression changes in neurons.

Various embodiments of the present disclosure relate to opsins or light-activated proteins with fast decay constants. This property can be particularly useful for providing precise control over spiking, e.g., in order to interfere minimally with intrinsic conductances, trigger single spikes per light pulse and/or minimize plateau potentials during light pulse trains. Experimental results suggest that the light-evoked photocurrents recorded in C1V1-ts-EYFP decayed with a time constant similar to that of VChR1. Aspects of the present disclosure are therefore directed toward modifications in the chromophore region to improve photocycle kinetics, reduced inactivation and/or possible further red-shifted absorption.

One embodiment is directed toward a corresponding ChETA mutation E162T, which experiments suggest provides an accelerated photocycle (e.g., almost 3-fold), (reference can be made to Gunaydin, et al., Ultrafast optogenetic control, Nat Neurosci, 2010, which is fully incorporated herein by reference). Surprisingly, this mutation was shown to shift the action spectrum hypsochromic to 530 nm, whereas analogous mutations in ChR2 or other microbial rhodopsins have caused a red-shift.

Another embodiment is directed toward a mutation of glutamate-122 to threonine (C1V1-E122T). Experimental tests showed that C1V1-E122T is inactivated only by 26% compared to 46% inactivation of ChR2; in addition, the spectrum was further red-shifted to 546 nm.

Another embodiment of the present disclosure is directed toward a double mutant of C1V1 including both E122T and E162T mutations. Experimental tests have shown that the inactivation of the current was even lower than in the E122T mutant and the photocycle was faster compared to E162T. This suggests that multiple useful properties of the individual mutations were conserved together in the double mutant.

Polynucleotides Encoding Light-Activated Proteins

Light-activated proteins or opsins described herein may be delivered into neurons by methods known in the art, such as by a polynucleotide comprising a sequence encoding the proteins. In some embodiments, the polynucleotide comprises an expression cassette. In some embodiments, the polynucleotide is a vector, such as a viral vector selected from the group consisting of an AAV vector, a retroviral vector, an adenoviral vector, an HSV vector, and a lentiviral vector.

For example, neurons may be contacted with a vector comprising a nucleic acid sequence encoding a light-activated protein operably linked to a cell specific promoter, wherein said neurons express the light-activated protein on the cell membrane. In some variations, the cell specific promoter is a calcium/calmodulin-dependent protein kinase IIa (CaMKIIa) promoter. In some variations, a nucleic acid sequence encoding light activatable eNpHR3.1 or eNpHR3.0 is operably linked to a CaMKIIa promoter in the vector. In some variations, the light-activated protein is expressed in excitatory glutamatergic neuron in the CA1 region, BLA and/or ACC. Any vectors that may be used for gene delivery may be used. In some variations, a viral vector (such as AAV, adenovirus, lentivirus, a retrovirus) may be used.

In some embodiments, the vector is a recombinant AAV vector. AAV vectors are DNA viruses of relatively small size that can integrate, in a stable and sitespecific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

AAV vectors may be prepared using standard methods in the art. Adeno-associated viruses of any serotype are suitable (see, e.g., Blacklow, pp. 165-174 of "*Parvoviruses and Human Disease*" J. R. Pattison, ed. (1988); Rose, *Comprehensive Virology* 3:1, 1974; P. Tattersall "The Evolution of Parvovirus Taxonomy" In *Parvoviruses* (J R Kerr, S F Cotmore. M E Bloom, R M Linden, C R Parrish, Eds.) p 5-14, Hudder Arnold, London, UK (2006); and D E Bowles, J E Rabinowitz, R J Samulski "*The Genus Dependovirus*" (J R Kerr, S F Cotmore. M E Bloom, R M Linden, C R Parrish, Eds.) p 15-23, Hudder Arnold, London, UK (2006), the disclosures of which are hereby incorporated by reference herein in their entireties). Methods for purifying for vectors may be found in, for example, U.S. Pat. Nos. 6,566,118, 6,989,264, and 6,995,006 and WO/1999/011764 titled "Methods for Generating High Titer Helper-free Preparation of Recombinant AAV Vectors", the disclosures of which are herein incorporated by reference in their entirety. Preparation of hybrid vectors is described in, for example, PCT Application No. PCT/US2005/027091, the disclosure of which is herein incorporated by reference in its entirety. The use of vectors derived from the AAVs for transferring genes in vitro and in vivo has been described (See e.g., International Patent Application Publication Nos: 91/18088 and WO 93/09239; U.S. Pat. Nos. 4,797,368, 6,596,535, and 5,139,941; and European Patent No: 0488528, all of which are herein incorporated by reference in their entirety). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In some embodiments, the vector(s) for use in the methods of the invention are encapsidated into a virus particle (e.g. AAV virus particle including, but not limited to, AAV1, AAV2, AAV3, AAV4, AAV5, AAV6, AAV7, AAV8, AAV9, AAV10, AAV11, AAV12, AAV13, AAV14, AAV15, and AAV16). Accordingly, the invention includes a recombinant virus particle (recombinant because it contains a recombinant polynucleotide) comprising any of the vectors described herein. Methods of producing such particles are known in the art and are described in U.S. Pat. No. 6,596,535.

For the animal cells described herein, it is understood that one or more vectors may be administered to neural cells, heart cells, or stem cells. If more than one vector is used, it is understood that they may be administered at the same or at different times to the animal cells.

For example, in some variations, C1V1 opsin genes in neurons were carried out by generating lentiviral vectors encoding C1V1-ts-EYFP and various point mutation combinations discussed herein. The opsins were then expressed in cultured hippocampal neurons and recorded whole-cell photocurrents under identical stimulation conditions (2 ms pulses, 542 nm light, 5.5 mW/mm$^2$). Photocurrents in cells expressing C1V1, C1V1-E162T and C1V1-E122T/E162T were all robust and trended larger than the photocurrents of ChR2-H134R. The experiments also included a comparison of integrated somatic YFP fluorescence and photocurrents from cells expressing C1V1-E122T/E162T and from cells expressing ChR2-H134R. Surprisingly, C1V1-E122T/E162T cells showed stronger photocurrents than ChR2-

H134R cells at equivalent fluorescence levels. This suggests that C1V1 could possess a higher unitary conductance compared with ChR2-H134R. The test results suggest that the kinetics of C1V1-E122T were slower than those of C1V1-E122T/E162T and that cells expressing C1V1-E122T responded more strongly to red light (630 nm) than cells expressing the double mutant. This can be particularly useful for generating optogenetic spiking in response to red light.

Consistent with various embodiments of the present disclosure, inhibitory and/or excitatory neurons residing within the same microcircuit are be targeted with the introduction of various light-activated proteins (e.g., opsins). Experimental tests were performed by separately expressed C1V1-E122T/E162T and ChR2-H134R under the CaMKIIa promoter in cultured hippocampal neurons. Cells expressing C1V1-E122T/E162T spiked in response to 2 ms green light pulses (560 nm) but not to violet light pulses (405 nm). In contrast, cells expressing ChR2-H134R spiked in response to 2 ms 405 nm light pulses, but not to 2 ms 561 nm light pulses.

Various embodiments of the present disclosure relate to independent activation of two neuronal populations within living brain slices. Experimental tests were performed by CaMKIIa-C1V1-E122T/E162Tts-eYFP and EF1a-DIO-ChR2-H134R-EYFP in mPFC of 20 PV::Cre mice. In non-expressing PYR cells, 405 nm light pulses triggered robust and fast inhibitory postsynaptic currents (IPSCs) due to direct activation of PV cells, while 561 nm light pulses triggered only the expected long-latency polysynaptic IPSCs arising from C1V1-expressing pyramidal cell drive of local inhibitory neurons.

Light Activation of Proteins Expressed in Neurons

Any device that is capable of applying light having a wavelength to activate the light-activated proteins expressed in a neuron may be used to depolarize and/or hyperpolarize the neuron. For example, a light-delivery device (100) for activating ion channels and/or ionic pumps to affect the membrane voltage of one or more neurons depicted in FIG. 1 may be used. As shown there, the light-delivery device (100) is configured to provide optical stimulus to a target region of the brain. The light-delivery device (100) may comprise a base (102), a cannula guide (104) that is attached to the base, and one or more optical conduits (106) attached to the base via the cannula guide. The base (102) may comprise one or more light delivery ports (108) that are positioned to deliver light from the optical conduits (106) to targeted tissue regions (101), such as the CA1 region (103). The optical conduits (106) may be optical fibers, where the proximal end of the fiber is attached to an optical light source (not shown), and the distal end is in communication with the light delivery ports (108). The optical light source may be capable of providing continuous light and/or pulsed light, and may be programmable to provide light in pre-determined pulse sequences. The light delivery device (100) may have any number of optical conduits (106) as may be desirable, e.g., 1, 2, 3, 4, 5, 10, 15, 20, etc. The optical conduits (106) may each carry light of the same or different wavelengths. The delivered light may have a wavelength between 450 nm and 600 nm, such as yellow or green light. The light delivery device (100) may have any number of light delivery ports (108) as may be desirable, e.g., 1, 2, 3, 4, 5, 10, 15, 20, etc. In some variations, there may be the same number of light delivery ports as optical conduits while in other variations, there may be different number of optical conduits and light delivery ports. For example, there may be a single optical conduit that conveys light to two or more light delivery ports. Alternatively or additionally, a single optical conduit may connect to a single light delivery port. The cannula guide (104) may be configured to help secure and align the optical conduits (106) with the light delivery ports (108). In some embodiments, the light delivery device (100) is configured to deliver bilateral light to the CA1 region (103) to affect the formation and retrieval of memories. Light delivery devices may also comprise one or more measurement electrodes that may be configured for measuring neural activity. For example, measurement electrodes may record changes in the membrane potential (e.g., action potentials) and/or current flow across a membrane of one or more neurons as the neurons respond to a stimulus. In some variations, the measurement electrodes may measure the electrical response of one or more neurons to optical stimulation. Measurement electrodes may be extracellular or intracellular electrodes.

Methods of Affecting Memory Function

As described herein, the target tissue regions (101) may include neural tissue with cells that have light-activated proteins designed to modify the membrane voltage of the cells in response to light. In some variations, light-activated proteins may be used to disrupt the formation and/or retrieval of memories by inhibiting the depolarization of the neurons in the CA1, BLA, and ACC regions of the brain. Embodiments of the present disclosure are directed towards disrupting memory acquisition, recall and/or associations between memory and emotional responses, such as fear. In a particular embodiment, function of a neural circuit involved in memory is disrupted by activation of light-activated ion channels (e.g., using NpHR, BR, AR, etc.) and/or pumps (e.g., a proton pump GtR3). In certain implementations, this disruption can be implemented during memory formation. In other implementations, this disruption can be implemented before or during memory retrieval. This can be particularly useful for psychiatric or neurological disorders involving memory recall, such as PTSD. Consistent with certain embodiments, the disruption can be triggered in response to a memory trigger event or other external stimulus that is presented and/or controlled for the disruption. For instance, the disruption can be provided in response to a trigger for a memory to an individual conditioned to respond to the trigger. In another instance, an individual can actively trigger the disruption. For instance, an individual may trigger the disruption when experiencing a memory associated with PTSD. Other embodiments of the present disclosure are directed toward encouraging memory acquisition, recall and/or associations between memory and emotional responses. The methods described herein may be used to ascertain the role of neuron(s) and/or neuronal circuits in memory function, and/or to treat disorders associated with memory impairment.

In some embodiments, the methods provided herein for reversibly affecting memory retrieval or formation in an individual comprise administering a polynucleotide encoding a light-activated protein to the dorsal CA1 field of the hippocampus, anterior cingulated cortex, or basolateral amygdala in the individual, wherein light-activated protein is expressed on the cell membrane of the excitatory neurons in the dorsal CA1 field of the hippocampus, anterior cingulated cortex, or basolateral amygdala and the protein is responsive to light and is capable of inhibiting depolarization of the neurons when the neurons are illuminated with the light, whereby activating the protein by the light reversibly affects memory retrieval or formation of an event in the individual. In some embodiments, the methods provided herein for reversibly affecting memory retrieval or formation in an individual comprise inhibiting depolarization of excitatory neurons in the dorsal CA1 field of the hippocampus, anterior cingulated cortex, or basolateral amygdala during memory retrieval or formation of an event in an individual, wherein a light-activated protein is expressed on the cell membrane of the excitatory neurons in the dorsal CA1 field of the hippocampus, anterior cingulated cortex, or basolateral amygdala of the individual, wherein the protein is responsive to light and is capable of inhibiting depolarization of the neurons when the neurons are illuminated with the light. In some embodiments, the event is a fearful event.

Provided herein are methods for treating post-traumatic stress disorder in an individual comprising: administering a polynucleotide encoding a light-activated protein to the dorsal CA1 field of the hippocampus, anterior cingulated cortex, or basolateral amygdala in the individual, wherein light-activated protein is expressed on the cell membrane of the excitatory neurons in the dorsal CA1 field of the hippocampus, anterior cingulated cortex, or basolateral amygdala and the protein is responsive to light and is capable of inhibiting depolarization of the neurons when the neurons are illuminated with the light, whereby activating the protein by the light reversibly affects memory retrieval or formation of an event in the individual.

Provided herein are methods for screening a pharmacological agent that affects memory retrieval or formation comprising: a) contacting excitatory neurons in the dorsal CA1 field of the hippocampus, anterior cingulated cortex, or basolateral amygdala during memory retrieval or formation of an event in a non-human animal with a pharmacological agent, wherein the non-human animal comprises a light-activated protein expressed on the cell membrane of excitatory neurons in the dorsal CA1 field of the hippocampus, anterior cingulated cortex, or basolateral amygdala of the animal, wherein the protein is responsive to light and is capable of inhibiting depolarization of the neurons when the neurons are illuminated with the light; b) inhibiting depolarization of the excitatory neurons in the dorsal CA1 field of the hippocampus, anterior cingulated cortex, or basolateral amygdala during memory retrieval or formation of an event; and c) determining if the pharmacological agent affects memory retrieval or formation in the presence or absence of the light.

As used herein, an "individual" is a mammal including a human. Mammals include, but are not limited to, farm animals, sport animals, pets, primates, mice and rats. Individuals also include companion animals including, but not limited to, dogs and cats. In one aspect, an individual is a human. In another aspect, an individual is a non-human animal. As used herein, "non-human animals" include non-human mammals.

Figure 2:
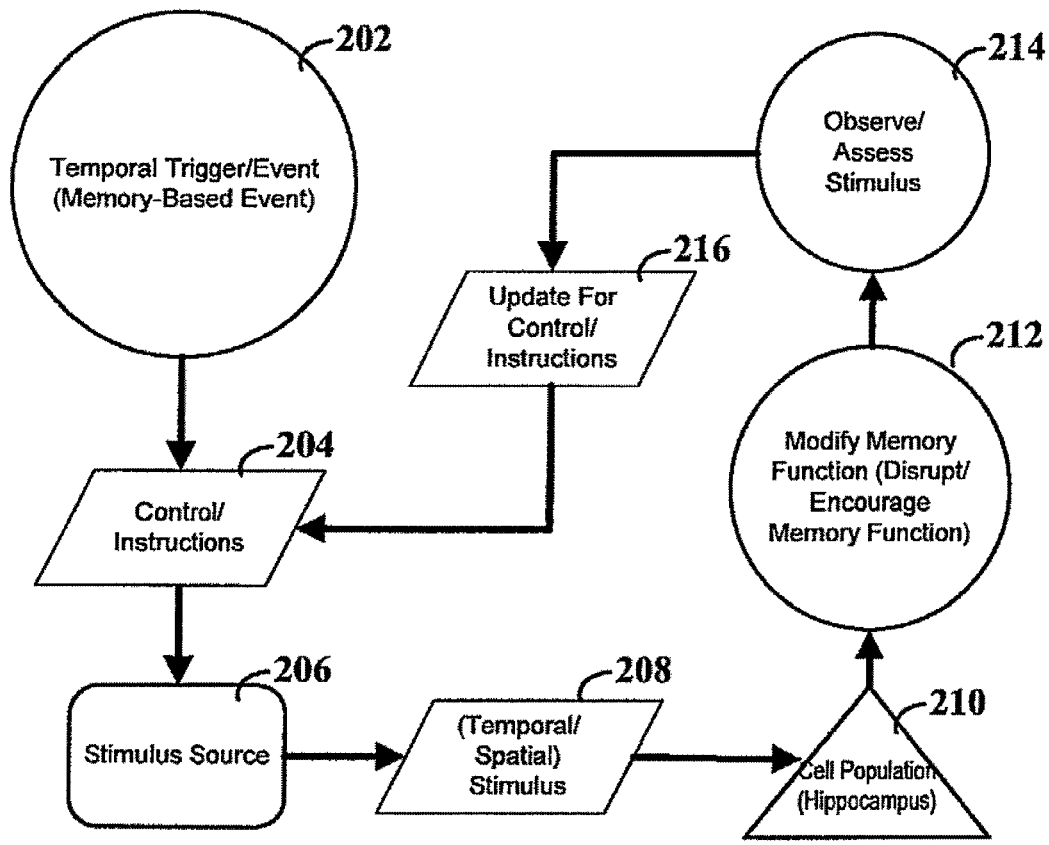
FIG. 2 depicts a flow diagram for modifying memory function.

One example of a method for controlling or modifying memory function consistent with the embodiments of the present disclosure is depicted in FIG. 2. A temporal-trigger event (202) provides a reference point for implementing control over memory function. As discussed herein, the temporal nature of the control can be particularly useful. Although not limited thereto, the memory-trigger event (202) can be linked to a training event. For instance, an individual (e.g., non-human animals, mammals, humans) can be introduced to a stimulus designed to train the individual to respond to a particular stimulus. The memory-trigger event (202) could be the introduction of the particular stimulus to the individual. In another instance, the memory-trigger event could be in response to a response or action of the individual (e.g., an indication that the individual is experiencing a PTSD event). Control instructions (204) determine how stimulus source (206) applies a stimulus (208) to a cell population (210). These control instructions can be determined and applied as a function of a desired target. The desired target can be defined by, for example, one or more of temporal attributes, spatial location and/or cell-type. The stimulus (208) results in the modification of memory function (212). The effect of the stimulus can then be monitored, observed and/or assessed (214). The monitoring can be used to adjust (216) the control instructions (204), thereby fine-tuning the stimulus for the intended result. Various embodiments discussed herein provide further examples that can be used in connection with (or in addition to) such a process for controlling and characterizing the neural circuits that underlie memory function.

Affecting Memory Retrieval by Inhibiting Neurons of CA1 and ACC

One variation of a method for disrupting memory retrieval may comprise inhibiting the excitatory neurons of the CA1 region (e.g., by blocking or reducing membrane depolarization, and/or by promoting membrane hyperpolarization). Light-activated ion channels, such as eNpHR3.1 or NpHR3.0, may be expressed on neurons located in the CA1 region of an individual by administering a polynucleotide encoding the channel protein to the region. The eNpHR3.1 or NpHR3.0 ion channel is activated in the presence of yellow light (e.g., having a wavelength of about 591 nm). The individual may be provided with a light-delivery device, such as the light-delivery device (100) described above. The light-delivery device may be positioned on the individual such that yellow light is capable of being delivered to the CA1 neurons. After or during the retrieval of a memory (e.g., any undesired memory such as a fearful or stressful memory), the light-delivery device may be activated to deliver yellow light to the CA1 neurons, thereby inhibiting their depolarization, and disrupting the recall of the memory. Once the memory recall has been sufficiently disrupted, the light-delivery device may be de-activated. Upon de-activation of the light-delivery device, the individual may regain the ability retrieve memories without disruption. This method may be used to disrupt recall of recent memories (e.g., memories of events that occurred less than one day in the past) and recall of remote memories (e.g., memories of events that occurred more than one day in the past, 1 week in the past, 2 weeks in the past, 4 weeks in the past, 8 weeks or more in the past, etc.). In some variations, excitatory neurons of the ACC may express similar light-activated proteins, and may be similarly inhibited to disrupt the retrieval of remote memories.

Methods for disrupting memory retrieval comprising inhibiting the neurons of the CA1 region may be used in a non-human animal, such as a mouse. For example, mice expressing eNpHR3.1 or NpHR3.0 in the neurons of the CA1 region were trained in a customized FC chamber, where they were introduced into context A and then presented twice with a tone followed by a foot-shock. In a testing session, green light delivered to the eNpHR3.1 or NpHR3.0 CA1 neurons interfered with the ability of the mice to recall the memory (i.e., a fearful or stressful memory), as measured by a reduction in freezing (e.g., contextual freezing). In a separate testing session where the eNpHR3.1 or NpHR3.0 CA1 neurons are not exposed to light, the mice are able to recall the fearful memory formed during the training session, as measured by normal rates of freezing. In some variations, the testing session may occur one day or less after the training session, while in other variations, the testing session may occur four weeks or more after the training session. Applying green light to the eNpHR3.1 CA1 neurons of the mice reversibly inhibits the depolarization of the neurons, thereby disrupting the recall of recent and/or remote contextual fearful memories. Removing the green light from the eNpHR3.1 or NpHR3.0 CA1 neurons restores the ability of the mice to recall recent and/or remote contextual fearful memories.

Methods for reversibly disrupting the recall or retrieval of remote memories may also be used after the memory has been repeatedly recalled and consolidated. For example, mice having CA1 neurons expressing eNpHR3.1 or NpHR3.0 may be trained as described above. In a testing session five weeks after the training session, the mice were able to recall the memory formed during training, however, when the eNpHR3.1 or NpHR3.0 CA1 neurons were exposed to green light, they were no longer able to recall the memory. Subsequent exposure of the eNpHR3.1 or NpHR3.0 CA1 neurons to green light disrupted retrieval of the fearful memory. In some methods, memory recall may be disrupted by exposing the eNpHR3.1 or NpHR3.0 CA1 neurons to light upon initiation of the memory recall and/or during the memory recall. For example, applying green light to the eNpHR3.1 or NpHR3.0 CA1 neurons at the same time as recall initiation (e.g., at the beginning of the testing session) disrupts recall of the memory. When green light was applied to the eNpHR3.1 or NpHR3.0 CA1 neurons during memory recall (e.g., applying the light some time after the testing session has begun, such as in the middle of the testing session), the mice initially recalled and responded to the fearful memory (by freezing), but then quickly ceased exhibiting the fear response after the light was applied. These methods may be used in an individual with PTSD having CA1 neurons expressing eNpHR3.1, where a light-delivery device may be activated at the same time and/or during the retrieval of a fearful memory in order to reversibly disrupt and/or discontinue recall of that fearful memory. Subsequent de-activation of the light-delivery device may restore the ability of the individual to recall this and other memories.

Methods for disrupting memory retrieval comprising inhibiting the neurons of the ACC region may be used in a non-human, such as a mouse. For example, mice expressing eNpHR3.1 in the neurons of the ACC may be trained as described above. In a testing session four weeks after the training session, green light delivered to the eNpHR3.1 ACC neurons interfered with the ability of the mice to recall the memory formed during training. Removing the green light from the eNpHR3.1 CA1 neurons restores the ability of the mice to remote fearful memories.

Affecting Memory Formation by Inhibiting CA1 Hippocampus

While inhibiting the depolarization of excitatory neurons in the CA1 region (and in some cases hyperpolarizing these neurons) may interfere with memory retrieval, such inhibition may also disrupt memory formation. One variation of a method for disrupting memory formation may comprise inhibiting the neurons of the CA1 region during the formation of a memory such as a contextual memory. Light-activated ion channels, such as eNpHR3.1, may be expressed on neurons located in the CA1 region of an individual as previously described. The individual may be provided with a light-delivery device, such as the light-delivery device (100) described herein. During the formation of a memory (e.g., a fearful or stressful memory), the light-delivery device may be activated to deliver green light to the CA1 neurons, thereby inhibiting their depolarization and disrupting the formation of the memory. Once the memory formation has been sufficiently disrupted, the light-delivery device may be de-activated. Upon de-activation of the light-delivery device, the individual may regain the ability form memories without disruption.

Methods for disrupting memory formation comprising inhibiting the neurons of the CA1 region may be used in a non-human animal, such as a mouse. For example, mice expressing eNpHR3.1 in the neurons of the CA1 region were trained in a customized FC chamber, while delivering green light to the eNpHR3.1 CA1 neurons. During the training, the mice were introduced into a first context and then exposed to a tone followed by a foot-shock. In a subsequent testing session without the application of light, the mice exhibited no memory of the training, as measured by a reduction in contextual freezing. The same mice underwent a separate training session where the eNpHR3.1 CA1 neurons were not exposed to light. The mice were then able to recall the memory in a subsequent testing session. In some variations, the testing session may occur one day or less after the training session, while in other variations, the testing session may occur four weeks after the training session. Applying green light to the eNpHR3.1 CA1 neurons of the mice reversibly inhibited the depolarization of the neurons, thereby disrupting the formation of recent and/or remote memories. Removing the green light from the eNpHR3.1 CA1 neurons restored the ability of the mice to form fearful memories.

Affecting Memory Formation by Inhibiting Basolateral Amygdala

Some variations of methods for disrupting memory formation may comprise delivering light to neurons expressing eNpHR3.1 in the BLA during memory formation. Light-activated ion channels, such as eNpHR3.1, may be expressed on neurons located in the BLA of an individual. The individual may be provided with a light-delivery device, such as the light-delivery device (100) described above. The light-delivery device may be positioned on the individual such that green light is capable of being delivered to the BLA neurons. After or during the formation of a memory (e.g., a fearful or stressful memory), the light-delivery device may be activated to deliver green light to the BLA neurons, thereby inhibiting their depolarization, and disrupting the formation of the memory. Once the memory formation has been sufficiently disrupted, the light-delivery device may be de-activated. Upon de-activation of the light-delivery device, the individual may regain the ability acquire memories without disruption.

Methods for disrupting memory acquisition comprising inhibiting the neurons of the BLA region may be used in a non-human animal, such as a mouse. For example, green light may be delivered to mice expressing eNpHR3.1 in the neurons of the BLA during a fear conditioning training session as described above. The mice may then be tested to determine whether they acquired the fearful memory of the training session. Green light delivered to the BLA during the training session may disrupt the ability of the mice to acquire a fearful or stressful memory.

Screening for Drugs that Repair Memory Formation or Retrieval

Figure 3A:
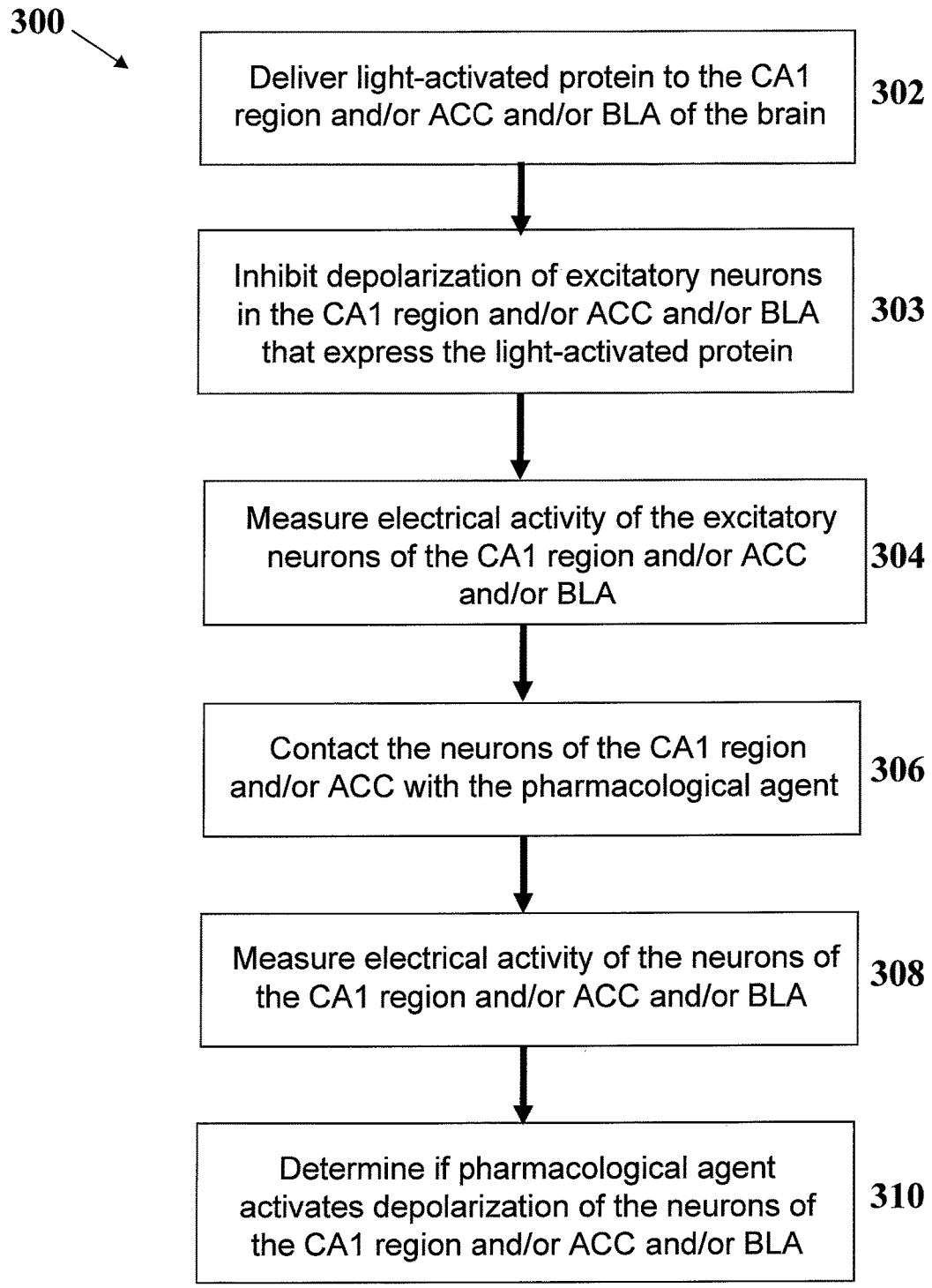
FIGS. 3A and 3B depict variations of methods for evaluating the effects of a test pharmacological agent on neural circuits that underlie memory function.

Controlling the neural circuit that underlies memory function may provide a tool for evaluating the effect of pharmacological agents on memory retrieval. For example, inhibiting the neurons expressing eNpHR3.1 of the CA1 region and/or ACC and/or BLA may be used to evaluate the effectiveness of various pharmacological agents for the restoration of memory recall. One example of a method for identifying a pharmacological agent that activates depolarization or excitation of non-human excitatory neurons in the CA1 region and/or ACC and/or BLA is depicted in FIG. 3A.

The method (300) may comprise delivering a light-activated protein to the CA1 region and/or ACC and/or BLA of the brain (302) and inhibiting depolarization of excitatory neurons of the CA1 and/or ACC region (303). As described above, inhibiting depolarization may comprise applying light having a selected wavelength (e.g., yellow or green) to eNpHR3.1 ion channels expressed on the neurons of the CA1 and/or ACC region to prevent the generation of action potentials. Other types of light-activated channels may also be expressed to inhibit depolarization of these excitatory cells, such as variants of NpHR, BR, AR, and proton pumps such as GtR3. The effect of the inhibition from activating the eNpHR3.1 ion channels may be electrically measured by using loose-cell or whole-cell patch clamp methods (304). In some variations, the electrical activity of the excitatory cells of the CA1 and/or ACC region may be measured using single electrodes and/or multielectrode arrays. The inhibited neurons of the CA1 and/or ACC region may then be contacted with a test pharmacological agent (306). The electrical activity of the neurons may be similarly measured (308). The electrical measurements of the excitatory neurons of the CA1 region and/or ACC and/or BLA before and after contacting with the test pharmacological agent may be compared to determine if the test agent activates and/or restores the depolarization of the neurons (310). The method (300) may be used repeatedly as desired to screen any number or variety of pharmacological agents.

Figure 3B:
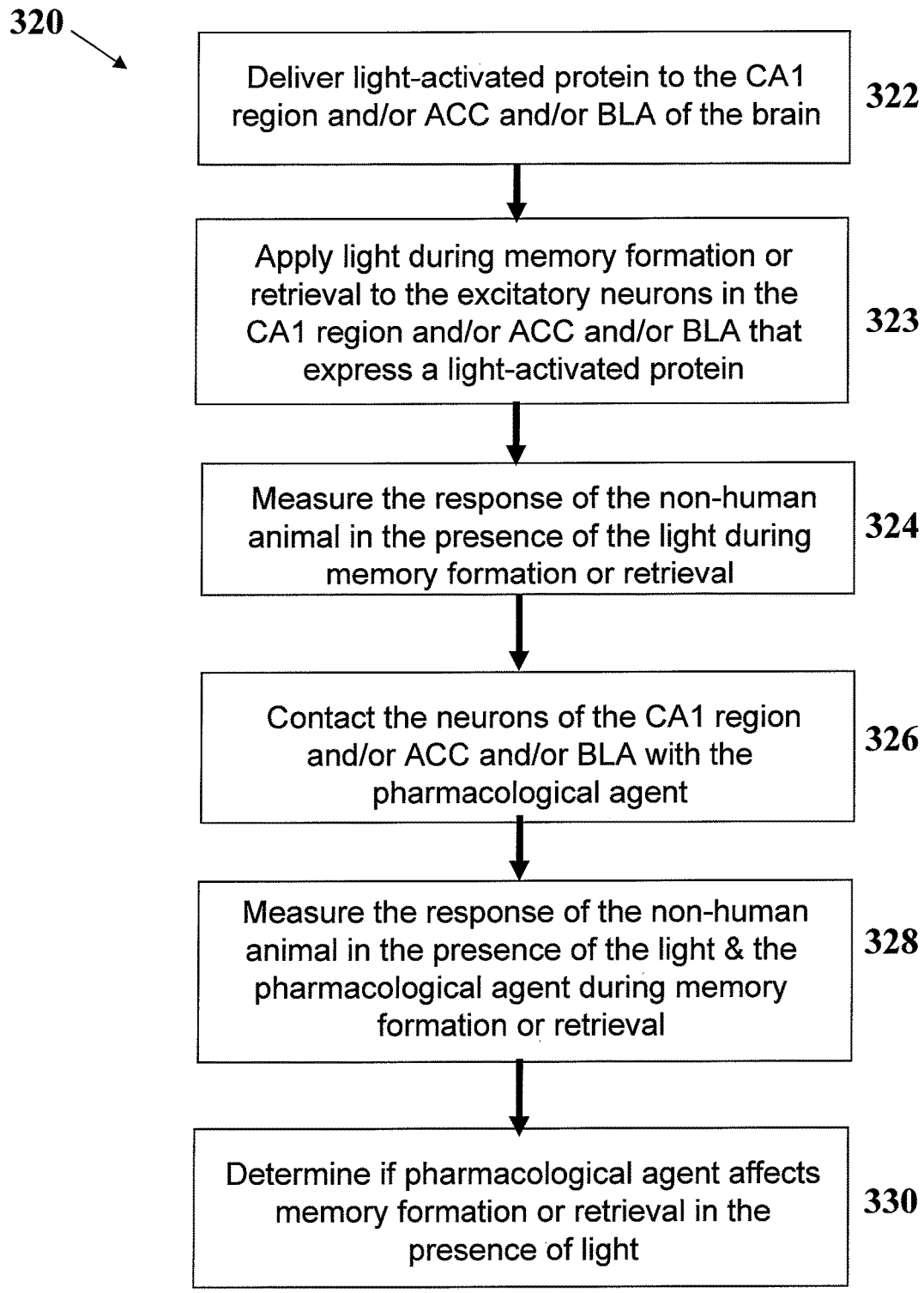

One example of a method for identifying a pharmacological agent that may be effective for restoring memory formation or retrieval in a non-human animal is depicted in FIG. 3B. The method (320) may comprise delivering a light-activated protein to the CA1 region and/or ACC and/or BLA of the brain (322) and applying light have a selected wavelength (e.g., yellow or green) to eNpHR3.1 ion channels expressed on the neurons of the CA1 and/or ACC and/or BLA region to prevent the generation of action potentials (323). Other types of light-activated channels may also be expressed to inhibit depolarization of these excitatory cells, such as variants of NpHR, BR, AR, and proton pumps such as GtR3. The response of the non-human animal in the presence of the light during memory formation or retrieval may be measured (324). In some variations, the memory may be formed during a training session where the individual is introduced into context A and exposed to a tone accompanied by a foot-shock, and the response to memory retrieval may be freezing when introduced into the context A and/or when the tone is played. The inhibited neurons of the CA1 and/or ACC region may then be contacted with a test pharmacological agent (326). The response of the non-human animal may be similarly measured (328). The response of the non-human animal before and after contacting with the test pharmacological agent may be evaluated to determine if the test agent affects memory formation or retrieval in the presence of light (330). In some variations, the method (320) may be used during memory formation (e.g., a training session) to evaluate the effect of the pharmacological agent on memory formation. The method (320) may also be used during memory retrieval (e.g., a testing session some time after a training session) to evaluate the effect of the pharmacological agent on memory retrieval. The method (320) may be used repeatedly as desired to screen any number or variety of pharmacological agents.

Variations on Temporal Precision that can Apply to all Above Methods

In some variations of the methods described above, inhibition of the neurons expressing the light-activated protein (e.g., eNpHR3.1 or eNpHR3.0) may be applied at a precise point in time. For example, neurons expressing eNpHR3.1 in the CA1 region may illuminated by light during the testing session only. Temporally precise inhibition of neurons expressing eNpHR3.1 may disrupt memory recall. Precisely applying light to neurons expressing eNpHR3.1 in the CA1 region of mice during the testing session may inhibit remote and/or recent fear memory retrieval in an animal. In other variations of the methods described above, inhibition of the neurons expressing eNpHR3.1 may be applied over a prolonged period of time. For example, neurons expressing eNpHR3.1 in the CA1 region may be illuminated by light before the testing session (e.g., 30 minutes or more before the testing session). Prolonged inhibition of the neurons expressing eNpHR3.1 in the CA1 region of the hippocampus may affect the retrieval of memories differently from precise inhibition of the CA1 neurons. For example, prolonged light application (i.e., prolonged inhibition) to CA1 neurons may affect recent contextual fear recall, but may not affect remote contextual memory recall.

Methods of Treating PTSD

One or more of the methods described above may be used to treat individuals with PTSD. Aspects of the present disclosure may be used to treat PTSD patients, in which a recurring disturbing memory may be stopped as it appears by reversibly shutting down a remote fearful memory in real-time before and after reconsolidation, or in real-time after it has already been retrieved. In some variations, a method for treating PTSD may comprise administering a viral vector encoding a light-activated protein to an individual. The light-activated protein may be configured to inhibit depolarization of the neuron in the presence of light with a specific wavelength. Examples of such light-activated proteins may include NpHR, BR, AR, and GrR3. As described previously, the viral vector may be delivered to any neuron population or type (e.g., the excitatory neurons of the CA1, ACC, and BLA brain regions). During the recall of an undesired memory (e.g., a fearful or stressful memory), the neuron(s) expressing the light-activated protein may be inhibited from depolarizing, thereby disrupting the retrieval of the undesired memory. In some variations, inhibiting depolarization of the neuron(s) may comprise applying light of the specific wavelength to the neurons expressing the light-activated proteins. Subsequently (e.g., after recall of the undesired memory has been disrupted), the light may be removed. This may restore memory function such that memories may be recalled without disruption. These steps may be repeated as may be desirable in the course of PTSD treatment.

Consistent with another embodiment of the present disclosure, memories related to drugs of abuse can be inhibited to reduce drug-seeking behavior. Other embodiments are directed toward the ability to instantaneously affect cognition by modulation of different brain areas in order to study the role of specific neuronal populations in memory processes. Inhibition of neurons by certain light-activated proteins and activation by other light-activated proteins may enable a finer temporal, genetic and spatial dissection of the neuronal circuits that underlie various brain function and behaviors.

Provided herein are methods of disrupting memory recall, the method comprising: inhibiting the function of the dorsal CA1 hippocampus circuit with a temporal precision of the inhibition that is sufficient to disrupt the effects of remote memory retrieval. In some embodiments, the step of inhibiting is responsive to a memory trigger event. In some embodiments, the step of inhibiting includes activating light-responsive opsins expressed in cells of the dorsal CA1 hippocampus circuit. In some embodiments, the step of inhibiting includes applying an electrical pulse through one or more electrodes positioned near the dorsal CA1 hippocampus circuit. In some embodiments, the step of inhibiting includes releasing a drug at a location proximate to the dorsal CA1 hippocampus circuit. In some embodiments, the effects of remote memory retrieval include emotional responses to a remote memory.

Also provided herein are methods of disrupting memory creation, the method comprising: inhibiting the function of the dorsal CA1 hippocampus circuit with a temporal precision of the inhibition that is sufficient to disrupt remote memory creation. In some embodiments, the step of inhibiting is responsive to a memory trigger event. In some embodiments, the step of inhibiting includes activating light-responsive opsins expressed in cells of the dorsal CA1 hippocampus circuit. In some embodiments, the step of inhibiting includes applying an electrical pulse through one or more electrodes positioned near the dorsal CA1 hippocampus circuit. In some embodiments, the step of inhibiting includes releasing a drug at a location proximate to the dorsal CA1 hippocampus circuit. In some embodiments, the effects of remote memory retrieval include emotional responses to a remote memory.

Also provided herein are methods of encouraging memory function, the method comprising: exciting the function of the dorsal CA1 hippocampus circuit to promote remote memory creation or remote memory recall.

Also provided herein are methods for treatment of a neurological disorder associated with remote memory recall, the method comprising: in response to retrieval of the remote memory, inhibiting the function of the dorsal CA1 hippocampus circuit with a temporal precision of the inhibition that is sufficient to disrupt the effects of the retrieval of the remote memory.

EXAMPLES

Various experiments and examples in accordance with the disclosure herein are provided below.

In exploring the contribution of defined cell types to remote memory using optogenetic methods (which are orders of magnitude faster in onset and offset than earlier methods), it was found that even many weeks after contextual conditioning (far into the "remote" phase), recall of contextual fear memory was abolished by optogenetic inhibition of excitatory neurons in the CA1 region of the hippocampus—at times when earlier studies had found no detectable influence of hippocampus. No effects of this intervention were observed on locomotion, anxiety, or cued memory formation, and remarkably, remote contextual memory could be instantaneously suppressed by CA1 inhibition even in the midst of a freely-moving behavioral session. The experiments described below confirmed that earlier observations however, as extending optogenetic inhibition of hippocampus to match typical pharmacological timescales converted the remote hippocampus-dependence to remote hippocampus-independence; optogenetic methods also confirmed the remote-timescale importance of anterior cingulate cortex (ACC), and showed that the hippocampus is involved in the recruitment of the ACC for remote recall. These findings have broad implications for the interpretation of drug and lesion data, illuminate puzzling aspects of the clinical hippocampus literature, and uncover a remarkable dynamism in memory retrieval, in which underlying neural circuitry adaptively shifts the default structures involved in memory—normally depending upon the hippocampus even at remote timepoints, but flexibly moving to alternate mechanisms on the timescale of minutes.

Various types of light-activated proteins may be used to control and characterize the neural circuits that underlie memory function. For example, variants of NpHR may be used to inhibit depolarization and/or hyperpolarize a neuron. The third generation eNpHR has a trafficking signal between the gene and the fluorophore and has shown improved membrane targeting and increased light-induced hyperpolarizations. This third generation eNpHR was used to perturb the neurons in the CA1 region of the hippocampus to determine their role in both recent and remote memory acquisition and recall. A lentiviral vector encoding eNpHR3.1 fused in-frame to enhanced yellow fluorescent protein (eNpHR3.1-EYFP) under control of the calcium/calmodulin-dependent protein kinase IIα (CaMKIIα) promoter, selective for excitatory glutamatergic neurons in hippocampus was used. eNpHR3.1 is a truncated version of eNpHR3.0 with a deletion of the intrinsic N-terminal signal peptide that is similar to eNpHR3.0 in both the photocurrent and the hyperpolarization induced in neurons.

EXPERIMENTAL PROCEDURES

Subjects.

C57BL6 mice aged 6 to 8 weeks were obtained from Charles River. Mice were housed four to five per cage in a colony maintained on a reversed 12 hr light/dark cycle and given food and water ad libitum. Experimental protocols were approved by Stanford University IACUC and meet guidelines of the National Institutes of Health guide for the Care and Use of Laboratory Animals.

Virus Production.

The CaMKIIα-eNpHR3.1-EYFP lentivirus for in vivo injection was produced as previously described (Gradinaru et al., 2010; Zhang et al., 2007). The adeno-associated virus (AAV) CaMKIIα-eNpHR3.0-EYFP plasmid was constructed by cloning eNpHR3.0-EYFP into an AAV backbone carrying the CaMKIIα promoter using BamHI and EcoRI restriction sites. The recombinant AAV vectors were serotyped with AAV5 coat proteins and packaged by the Vector Core at the University of North Carolina; titers were 2×1012 particles/mL. The maps for AAV CaMKIIα::eNpHR3.0 and Lenti CaMKIIα::eNpHR3.1 are available online at www.optogenetics.org.

Stereotactic Virus Injection, Cannula/Patchcord Implantation, and Light Delivery.

Mice were anesthetized with isoflurane, the head was placed in a stereotactic apparatus (Kopf Instruments, Tujunga, Calif.; Leica stereomicroscope). Ophthalmic ointment was applied to prevent eye drying. A midline scalp incision was made and then a small craniotomy was performed and the virus was delivered using a 101 syringe and a thin 34 gauge metal needle (World Precision Instruments, Sarasota, Fla.). The injection volume and flow rate (1 μl at 0.1 μl/min) were controlled by an injection pump (WPI). After injection the needle was left in place for 5 additional minutes and then slowly withdrawn. For CA1 optogenetic inhibition, 2 μl of concentrated lentivirus carrying CaMKIIα::eNpHR3.1-EYFP was microinjected into two sites in the CA1 (1 μl/site) of both left and right adult hippocampus. Site one: anteroposterior (AP), −1.5 mm from bregma, mediolateral (ML), +1 mm, dorsoventral (DV) −1.5; site two: AP, −2.5 mm, ML, ±2 mm, DV −1.5 mm. A bilateral guide cannula (2.5 mm center to center; PlasticsOne, Roanoke, Va.) was then placed 0.5 mm above CA1

(AP, −1.94 mm, ML, +1.25 mm, DV −1 mm), and secured to the skull using dental cement (C&B metabond, Parkell, Edgwood, N.Y.). The skin was glued back with Vetbond tissue adhesive. The animal was kept on a heating pad until it recovered from anesthetic. Buprenorphine (0.03 mg/kg) was given subcutaneously at the beginning of the surgical procedure to minimize discomfort. To inhibit neuronal activity, green light (561 nm, describe laser etc) was bilaterally delivered through two 300 m thick optic fibers (Thorlabs, Newton, N.J.) that were inserted through the guide cannulas, with a 0.5 mm projection. Control mice were either uninfected with eNpHR3.1 but still implanted with the cannula delivering light into CA1, or were infected with eNpHR3.1 and implanted, but connected to a dummy fiber that terminated the light delivery at the surface of the brain. Control mice therefore experienced identical visual cues and contextual information as the experimental mice associated with laser light delivery. For basolateral amygdala (BLA) optogenetic inhibition, 1.5 μl of AAV5 CaMKIIα::eNpHR3.0-EYFP was microinjected into both left and right BLA (AP, −1.5 mm, ML, ±3.47 mm, DV −5 mm). A patchcord (a metal ferrule, 2.5 mm in diameter with a 200 m thick, 5 mm long, cleaved bare optic fiber; Doric lenses Inc., Quebec, Canada) was then placed in each BLA (AP, −1.5 mm, ML, ±3.47 mm, DV −4.8 mm), and secured to the skull using dental cement. Green light was bilaterally delivered through two 200 m thick optic fibers (Doric lenses) that were attached to the patchcord using a connecting plastic sleeve. For anterior cingulate cortex (ACC) optogenetic inhibition, 1.01 of AAV5 CaMKIIα::eNpHR3.0-EYFP was microinjected into both left and right ACC (AP, +1 mm, ML, ±0.35 mm, DV −2.2 mm). A patchcord (Doric lenses Inc.) was then unilaterally placed above one ACC, as close as possible to the midline (AP, +1 mm, ML, ±0.2 mm, DV −1.25 mm), and secured to the skull using dental cement. Green light was delivered through a 200 μm thick optic fiber (Doric lenses) attached to the patchcord. For olfactory bulb (OB) optogenetic inhibition, 1.0 μl of AAV5 CaMKIIα::eNpHR3.0-EYFP was microinjected into both left and right OB (AP, +4.5 mm, ML, ±0.75 mm, DV −3.25 and −2 mm). A patchcord (Doric lenses Inc.) was then unilaterally placed above one OB, as close as possible to the midline (AP, +4.5 mm, ML, ±0.15 mm, DV −1.4 mm), and secured to the skull using dental cement. Green light was delivered through a 200 μm thick optic fiber (Doric lenses) attached to the patchcord.

Immunohistochemistry.

To measure the spread and determine the specificity of eNpHR-EYFP expression in CaMKIIα positive neurons, mice were anesthetized with ketamine/xylazine and perfused transcardially with cold PBS followed by 4% paraformaldehyde (PFA) dissolved in phosphate-buffered saline (PBS, pH 7.4). The brains were removed and post-fixed in 4% PFA in PBS for 3 hr at 4° C., and then equilibrated in 30% sucrose in PBS. 40 μm-thick coronal sections were cut on a freezing microtome (Leica) and stored in cryoprotectant (25% glycerol, 30% ethylene glycol, in PBS) at 4° C. until processed for immunohistochemistry. Free-floating sections were washed in PBS and then incubated for 30 min in 0.2% Triton X-100 (Tx100) and 2% normal donkey serum (NDS). Slices were incubated overnight with primary antibody in 2% NDS (Mouse anti-CaMKIIα 1:500, Abcam, Cambridge, Mass.; Rabbit anti GABA 1:500, Millipore, Billerica, Mass.; Rabbit anti c-Fos 1:500, EMD Darmstadt, Germany). Sections were then washed with PBS and incubated for 2 hr at room temperature with secondary antibodies (Donkey anti mouse conjugated to Cy3, donkey anti rabbit conjugated to either Cy3 or Cy5, all 1:1000, Jackson Laboratories, West grove, PA). Slices were then washed, incubated with DAPI (1:50,000) for 20 min, washed again, and mounted on slides with PVA-Dabco (Sigma). Confocal fluorescence images were acquired on a scanning laser microscope using a 5× or a 10× air objectives, or a 40× oil immersion objective. To determine the rate of viral transduction we calculated the percentage of CaMKIIα-immunoreactive neurons per 40× field that were also eNpHR-EYFP-positive.

In Vivo Optrode Recording.

Simultaneous optical stimulation and electrical recording in the CA1 was carried out as described previously (Gradinaru et al., 2007) using an optrode consisting of an extracellular tungsten electrode (1 MΩ, ~125 μm) tightly bundled with an optical fiber (200 μm core diameter, 0.2 N.A.), with the tip of the electrode protruding slightly beyond the fiber end (~0.4 mm) to ensure illumination of the recorded neurons. Recordings were conducted with the optrode initially placed at the boundary of CA1 (AP, −1.94 mm; ML, 1.4 mm; DV, −1.1) and gradually lowered in 0.1 mm increments. The optical fiber was coupled to a 473 nm solid-state laser diode with ~20 mW of output from the 200 μm fiber. Single unit recordings were done in mice anesthetized with a ketamine/xylazine mixture (ketamine, 80 mg/kg; xylazine, 15-20 mg/kg) diluted in PBS. Signals were recorded and band-pass filtered at 300 Hz low/5 kHz high using an 1800 Microelectrode AC Amplifier.

Measurement of Learning and Memory in the Fear Conditioning Paradigm.

Figure 5:
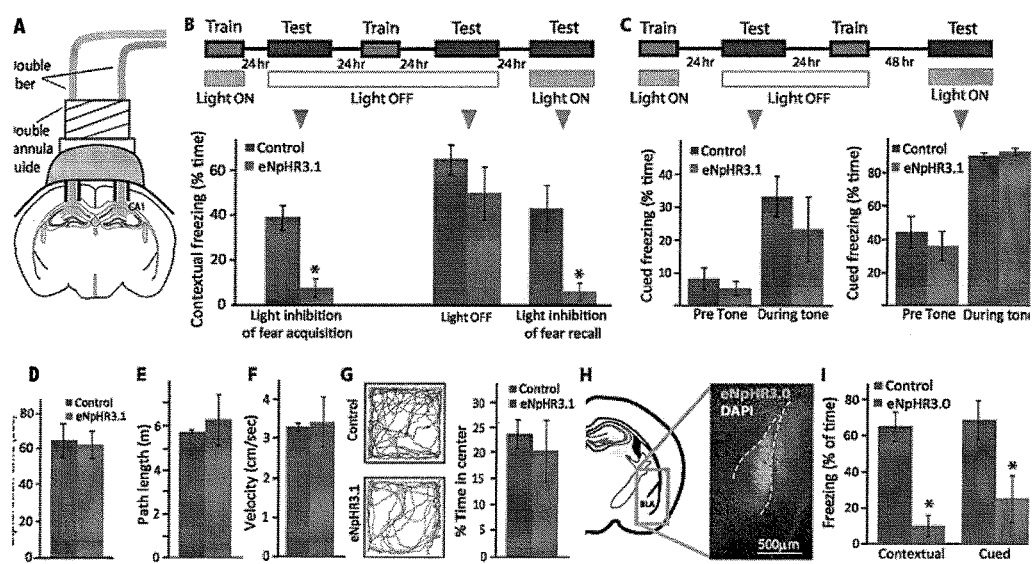
FIGS. 5A-5I depicts experimental data showing that real time CA1 optogenetic inhibition blocks contextual fear acquisition and retrieval.

The fear conditioning apparatus consisted of a square conditioning cage (18×18×30 cm), with a grid floor wired to a shock generator and a scrambler, surrounded by an acoustic chamber (Coulbourn instruments, PA, USA.). The apparatus was modified to enable light delivery during training and/or testing. To induce fear-conditioning mice were placed in the cage for 120 seconds, and then a pure tone (2.9 kHz) was sound for 20 sec, followed by a 2 sec, foot-shock (0.5 mA for short-term memory, 1 mA for long-term memory). This procedure was then repeated, and 30 sec after the delivery of the second shock mice were returned to their home cage. Fear conditioning was assessed by a continuous measurement of freezing (complete immobility), the dominant behavioral fear response (Fanselow, 2000). Freezing was measured continuously throughout the testing trial by an experienced experimenter blind to the treatment group. To test contextual fear conditioning mice were placed in the original conditioning cage, and freezing was measured for 5 min. To test auditory-cued fear conditioning mice were placed in a different context—a pyramid shaped cage with a smooth floor. As a control for the influence of the novel environment, freezing was measured for 2.5 min in this new cage, and then a 2.9 kHz tone was sound for 2.5 min, during which conditioned freezing was measured. This basic paradigm was applied under variable conditions in the different experiments: In the first experiment (FIG. 5) mice were trained and tested as follows: Day 1—training with continuous 561 nm light administration (light ON). Day 2—contextual and cued tests (2 hr apart) without light administration (light OFF). Day 3—training, light OFF. Day 4—test, light OFF. Day 5—contextual and cued tests, light ON. In the first remote memory experiment (FIG. 6A): Day 1—training, light OFF. Day 29—contextual and cued tests, light ON. Day 30—test light OFF. In a second remote memory experiment (FIG. 6C): Day 1—training, light OFF. Day 64—contextual test, light ON. In a third experiment (FIG. 8): Day 1—training, light OFF. Day 36—test, light OFF. Day 37—test light ON. Day 38—test with 3 min light OFF followed by 3 min light ON.

In the BLA experiment (FIG. 5H-I) mice were trained on day 1 with light ON, and tested for contextual and cued fear on day 2 with light OFF. In the ACC (FIGS. 10A-B) and OB experiments mice were trained on day 1 with the light OFF, tested on day 2 with the light ON, and then tested on day 29 with light ON. For prolonged light exposure (FIGS. 7A,B, 10C), the optic fibers were passed through the conditioning cage into a regular housing cage with bedding, and light was delivered in this cage for 30 min. The mouse was then placed in the conditioning cage for a five min test, as light delivery continued without interruption. The results of the contextual- and cued-conditioning tests were analyzed by a Student's t-test or 2-way ANOVA, followed by post-hoc tests, as applicable.

Drug Delivery.

For the pharmacological experiments (FIG. 6D-E), mice were implanted with a double cannula above CA1. The cannula, surgical procedure and location were the same as in the light delivery experiments. As described by Kitamura et al. (Kitamura et al., 2009) TTX (Sigma, 20 µM) and CNQX (Tocris Bioscience, Ellisville, Mo.; 3 mM) or saline were infused in a volume of 1 µl through a 28 gauge stainless steel internal cannula (PlasticsOne) that was 0.5 mm longer than the guide cannula. The internal cannula was connected to a micro-syringe pump (Harvard Apparatus, Holliston, Mass.) by a PE20 tube. Solutions were administered at a constant rate of 200 nl/min, and the injection cannula was removed 2 min following the termination of the injection to avoid spillage from the guide cannula.

Open Field Test.

The open field test was conducted in an open plastic arena (50 cm long×50 cm wide×40 cm deep). Mice were individually placed in the center of the chamber and allowed to freely explore for 3 min. Activity in both the central and periphery of the field was measured using an automated video-tracking system (Biobserve, Bonn, Germany). Percentage of time in center is defined as the percent of total time that was spent in the central 35×35 cm area of the open field.

Electrophysiological Measurement of Continuous Inhibition of Evoked Spiking by eNpHR3.1

Four mice from the prolonged light exposure experiment were injected as described above, went through behavioral testing, and then sacrificed and sliced for physiology. Coronal slices containing dorsal CA1 were prepared by perfusing ice cold sucrose solution transcardially which contained (in mM): 26 NaHCO3, 2.5 KCl, 1.25 NaH2PO4, 10 MgSO4H14O7, 0.5 CaCl2H4O2, 11 glucose, and 234 sucrose, and subsequently cutting 300 micron slices in the same ice cold sucrose solution. Electrophysiological recordings were made under the constant perfusion of aCSF, which contained (in mM): 126 NaCl, 26 NaHCO3, 2.5 KCl, 1.25 NaH2PO4, 1 MgCl2, 2 CaCl, and 10 glucose. All recordings were performed at 32° C. Patch electrodes (tip resistance=2-6 MΩ) were filled with (in mM): 130 K-gluconate, 10 KCl, 10 Hepes, 10 EGTA, and 2 MgCl (pH adjusted to 7.3 with KOH). Series resistance was usually 10-20MΩ, and experiments were discontinued if it exceeded 30 MΩ. The membrane potential was corrected for a measured liquid junction potential of 7 mV. Induction of action potentials was done by injecting current ranging from 200 pA at 10 hz. Light for the activation of eNpHR3.1 was delivered using a X-Cite 120 W halogen light source through a 531±20 nm filter and a 40×/0.8 NA water objective at 7 mW/mm$^2$.

Electrophysiological Comparison Between eNpHR3.1 and eNpHR 3.0 in Cultured Neurons.

Hippocampal Cultures: Primary cultured hippocampal neurons were prepared from P0 Sprague-Dawley rat pups. The CA1 and CA3 regions were isolated, digested with 0.4 mg/mL papain (Worthington, Lakewood, N.J.), and plated onto glass coverslips precoated with 1:30 Matrigel (Beckton Dickinson Labware, Bedford, Mass.) at a density of 65,000/cm$^2$. Cultures were maintained in a 5% CO$_2$ humid incubator with Neurobasal-A medium (Invitrogen Carlsbad, Calif.) containing 1.25% FBS (Hyclone, Logan, Utah), 4% B-27 supplement (GIBCO, Grand Island, N.Y.), 2 mM Glutamax (GIBCO), and FUDR (2 mg/ml, Sigma).

Calcium Phosphate Transfection.

6-10 div hippocampal neurons were grown at 65,000 cells/well in a 24-well plate. DNA/CaCl2 mix for each well: 1.5-3 µg DNA (QIAGEN endotoxin-free preparation)+1.875 µl 2M CaCl2 (final Ca2+ concentration 250 mM) in 15 µl total H20. To DNA/CaCl2 was added 15 µl of 2×HEPES-buffered saline (pH 7.05), and the final volume was mixed well by pipetting. After 20 min at RT, the 30 µl DNA/CaCl2/HBS mixture was dropped into each well (from which the growth medium had been temporarily removed and replaced with 400 µl warm MEM) and transfection allowed to proceed at 37 C for 45-60 min. Each well was then washed with 3×1 mL warm MEM and the growth medium replaced. Opsin expression was generally observed within 20-24 hr.

Electrophysiology.

Whole-cell patch clamp recordings were performed as previously described (intracellular solution: 129 mM K-gluconate, 10 mM HEPES, 10 mM KCl, 4 mM MgATP, 0.3 mM Na3GTP, titrated to pH 7.2; extracellular Tyrode: 125 mM NaCl, 2 mM KCl, 3 mM CaCl2, 1 mM MgCl2, 30 mM glucose, and 25 mM HEPES, titrated to pH 7.3). For voltage clamp recordings cells were held at −70 mV. Light was delivered from a 300 W DG-4 lamp (Sutter Instruments, Novato, Calif.) through a 593/40 nm filter (Semrock, Rochester, N.Y.) and a Leica 40×/0.8NA water objective; light power at the sample was 3 mW/mm$^2$. Whole-cell patch clamp data are from cultured hippocampal neurons either transfected or transduced with lentiviral eNpHR3.0 and eNpHR3.1 and allowed to express for one week. Expression was driven by the human CaMKIIα promoter and visualized by fusion to EYFP.

Neuronal Activation Imaging by cFos Staining.

YFP control and eNpHR3.1 mice were trained with light administration during conditioning (without tone presentation, so that only fear of the context would be induced), and sacrificed 90 min later to test for c-Fos levels (described in detail in the immunohistochemistry section above). Two other groups of non-trained control and eNpHR3.1 mice were sacrificed from their home cages. For remote memory, YFP controls and eNpHR3.1 mice were fear-conditioned without light, exposed to the conditioning context with light 28 days later, and sacrificed 90 min afterwards to test for cFos levels. The control groups at this time point were control and eNpHR3.1 mice that were trained, and then sacrificed from their home cages 28 days later without being re-exposed to the conditioning context.

Results

Specific Optogenetic Inhibition of Excitatory Neurons in Dorsal CA1 Reduces Neuronal Activity.

Figure 4:
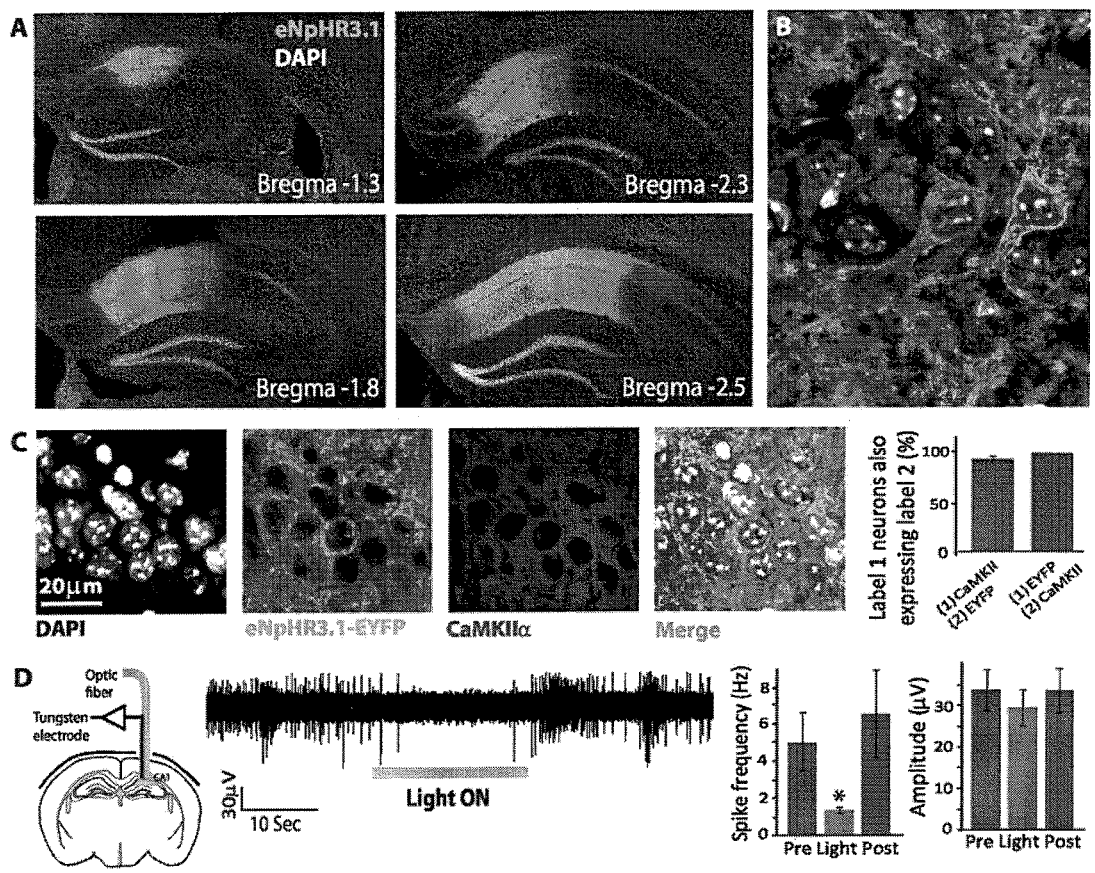
FIGS. 4A-D depicts experimental data showing specific optogenetic inhibition of excitatory neurons in dorsal CA1 reduces neuronal activity.

Stereotactic delivery of the CaMKIIα::eNpHR3.1 vector was found to result in CA1-specific expression (FIG. 4A). eNpHR3.1 is a truncated version of eNpHR3.0 with a deletion of the intrinsic N-terminal signal peptide, that has comparable effects on membrane potential. eNpHR3.1 is targeted to the neuronal membrane, and is expressed around the soma, as well as in the apical and basal dendrites of CA1 neurons (FIG. 4B). Within the transfected area, 94% (458/486 cells, from 3 mice) of the CaMKIIα cells expressed eNpHR3.1, and the promoter provided complete specificity; all eNpHR3.1-EYFP cells were also CaMKIIα positive (FIG. 4C). The eNpHR3.1 protein was expressed in CA1, but under these expression conditions not in other hippocampal sub-fields, in the parietal cortex above the injection sites, in thalamus or in habenula. The cannula track (at bregma −1.94) could be seen above the expression sites. The volume of infection covered a substantial fraction of dorsal CA1 ($0.875 \pm 0.05$ mm$^3$; N=12 mice).

To verify the physiological effect of eNpHR3.1 on CA1 neuronal activity, 'optrode' recordings (simultaneous optical stimulation and electrical recording using an extracellular electrode coupled to a fiber optic cable) of CA1 neurons in anesthetized mice were performed (FIG. 4D left), and the experiments confirmed that continuous 561 nm illumination of excitatory CA1 neurons potently inhibited spiking in vivo (FIG. 4D) in a temporally precise and reversible manner, without affecting spike amplitudes. 561 nm illumination of CA1 neurons in these mice resulted in a reversible, marked reduction in spiking frequency ($4.93 \pm 1.6$ Hz, $1.31 \pm 0.15$ Hz, and $6.45 \pm 2.4$ Hz; before, during and after light administration, respectively, in 15 traces from 2 mice, P<0.02), without affecting average spike amplitude ($33.55 \pm 4.94$ µV, $29.20 \pm 4.4$ µV, and $33.32 \pm 5.45$ µV; before, during and after light). A representative optrode recording trace, as well as average frequency and amplitude are shown (mean±SEM).

CA1 Optogenetic Inhibition Blocks Contextual Fear Acquisition and Retrieval.

The involvement of the hippocampus in contextual fear conditioning is based on physical, pharmacological and genetic lesions to this structure, in which the interval between lesion and testing ranges from tens of minutes to several weeks (Anagnostaras et al., 1999; Kim and Fanselow, 1992; Kitamura et al., 2009; Shimizu et al., 2000; Wiltgen et al., 2010), which could allow for adaptation and compensation within the relevant neural circuitry. To first test if real-time optogenetic inhibition of CA1 could modulate memory formation, bilateral continuous green (561 nm) light via two optical fibers inserted through a double cannula system was delivered targeting dorsal CA1 (FIG. 5A) in freely-moving mice in a customized FC chamber. Light was delivered to all mice, and was accompanied by CA1 inhibition in eNpHR3.1 but not control mice (which were either not infected but implanted with a cannula and received light into CA1, or mice infected and implanted connected to a dummy fiber that did not extend into the brain). During fear-conditioning training, mice were introduced into context A, and then presented twice with a tone followed by a foot-shock, under continuous bilateral 561 nm light delivery, and mice were tested for their memory 24 hr later without light. Fear memory was then assessed the next day in the absence of optical inhibition. Dorsal CA1 optogenetic inhibition during training completely prevented contextual fear acquisition eNpHR3.1 mice (n=5) compared to controls (n=4) ($39 \pm 5.4$ vs. $7.6 \pm 4.3\%$ freezing; means±SEM, P<0.005 (FIG. 5B, left). To test whether the effect of optogenetic inhibition was reversible, all mice were then re-trained in the same context without light administration, and tested again on the next day; indeed, eNpHR3.1 mice exhibited intact contextual memory ($64.6 \pm 6.6$ vs. $49.7 \pm 11.7\%$ freezing; P>0.5) when no light was administered during training (FIG. 5B, middle).

Next, whether dorsal CA1 optogenetic inhibition could also interfere with memory recall was tested. To that end the same mice were tested, this time with light delivery during recall, and it was found that the memory that was present the day before became unavailable for recall under illumination (FIG. 5B, right; $42.6 \pm 10.1$ vs. $5.94 \pm 4.1\%$ freezing, P<0.01). These experiments support prior understanding that the hippocampus is required for acquisition and recall of recent contextual fear memory, by directly demonstrating the real-time importance of CA1 excitatory cells in these processes. To verify that these effects were specific to contextual fear memories and not fear acquisition and fear expression mechanisms in general, the same mice were tested in a different context for their memory of the tone; eNpHR3.1 mice (n=5) demonstrated intact auditory-cued fear memory acquisition following CA1 light inhibition during training (FIG. 5C, left), as well as intact cued fear recall with illumination during the test (FIG. 5C, right) as compared to controls (n=4). These findings demonstrate the functional specificity of the optogenetic manipulation in affecting only the hippocampus-dependent task.

To further validate the optogenetic system, a number of additional control experiments were carried out. Because spatial exploration is critical for contextual fear acquisition (McHugh and Tonegawa, 2007), exploration time within the conditioning chamber during training under light stimulation was measured, and it was found no difference between eNpHR3.1-expressing animals (n=5) and control animals (n=5; FIG. 5D). CA1 optogenetic inhibition also had no effect on exploration of a novel environment. To verify that CA1 optogenetic inhibition did not have an anxiolytic effect, mice were tested for open field exploration during light administration; no differences in path length (FIG. 5E; $564 \pm 9$ and $618 \pm 114$ cm, eNpHR3.1 and control respectively), velocity (FIG. 5F; $3.3 \pm 0.1$ vs. $3.43 \pm 0.6$ cm/sec, eNpHR3.1 and control respectively), or the percent of time spent in the center of the field (which serves as a sign of anxiety-related behavior) were found between eNpHR3.1-expressing (n=6) and control mice (n=4; FIG. 5G; $23.8 \pm 2.76\%$ vs. $20.46 \pm 5.97\%$, P>0.5).

Finally, mice were bilaterally injected in the basolateral amygdala (BLA; FIG. 5H) instead of hippocampus and it was found that it was possible to optogenetically inhibit both contextual (FIG. 5I; $65.5 \pm 7.2$ vs. $9.6 \pm 5.5\%$ freezing; P<0.001) and auditory-cued FC acquisition (FIG. 5I; $69.5 \pm 9.6$ vs. $24.5 \pm 13\%$ freezing; P<0.05) in eNpHR3.0 (n=4) mice, compared to controls (n=9), as expected from prior findings that acquisition of fear itself and the expression of recent and remote fear depend on the amygdala (Han et al., 2009; Johansen et al., 2010; Killcross et al., 1997; LeDoux, 2000; Lee et al., 2006; Maren and Quirk, 2004). Together this constellation of findings confirm the validity of the real-time, fast, cell type-specific, reversible optogenetic system, and support a wide array of major prior findings in the memory literature by directly demonstrating the real-time role of the hippocampus in acquisition and recall.

CA1 Optogenetic Inhibition Reversibly Interferes with Remote Fear Memory Recall.

The role of the hippocampus in remote memory recall was explored. A group of mice with contextual FC as before was trained and the subjects were tested 4 weeks later (FIG. 6A), far into the remote phase when no hippocampus involvement is expected. Surprisingly, it was found that CA1 inhibition during recall completely blocked remote fear memory (P<0.0001; Control n=14, $69.8 \pm 5.3\%$ freezing eNpHR3.1 n=6, $14 \pm 6.4\%$ freezing). This interference with recall was reversible; when the same mice were re-tested on the next day without illumination, the fear memory was fully expressed as in controls (FIG. 6A; 52.45±6.0 vs. 45.18±11.5% freezing; P>0.5). Moreover, eNpHR3.1 mice demonstrated intact remote auditory-cued fear memory recall with illumination during the cued test (FIG. 6B; Control n=14, 22.3±6.8%, eNpHR3.1 n=6, 11.8±3.5% freezing in the new context; and 72.4±8.4 vs. 58.77±7.9% freezing to the tone; P>0.5), further demonstrating that fear expression mechanisms remained intact. To test if the hippocampus would still be involved in contextual fear recall even at much longer time intervals, another population of mice were trained and this cohort was tested 9 weeks after contextual FC. It was found that CA1 inhibition during recall blocked remote fear memory even after this very long interval and was never previously evoked (FIG. 6C; P<0.005; Control n=9, 31.8±3.8% freezing eNpHR3.1 n=6, 11.3±3.6% freezing).

These results point to ongoing involvement of the hippocampus in remote contextual fear memories, suggesting that the intact hippocampus is still the default activator of the memory trace. They stand in contrast with prevailing theories based on elegant and pioneering physical, pharmacological or genetic lesions to the hippocampus, in which the interval between lesion and recall-test ranges from tens of minutes to several weeks (Anagnostaras et al., 1999; Kim and Fanselow, 1992; Kitamura et al., 2009; Shimizu et al., 2000; Wiltgen et al., 2010). Indeed, the experiments demonstrated that pharmacological inhibition of hippocampus using TTX and CNQX, as previously reported (Kitamura et al., 2009), disturbed only recent (FIG. 6D; saline n=5, 56.86±1.9% freezing; TTX+CNQX n=4, 26.05±10.23% freezing; P<0.05) but not remote (FIG. 6E; saline n=8, 93.93±2.54% freezing; TTX+CNQX n=9, 83.8±4.4% freezing; P>0.05) fear recall when using the FC protocol, confirming earlier results. Thus, the speed and specificity of optogenetics could instead permit testing the causal role of cells and circuits as they are employed in behaving animals, by not allowing expression of compensatory mechanisms. This hypothesis was next explicitly tested.

Precise, but not Prolonged CA1 Optogenetic Inhibition Blocks Remote Contextual Fear Recall.

Figure 7:
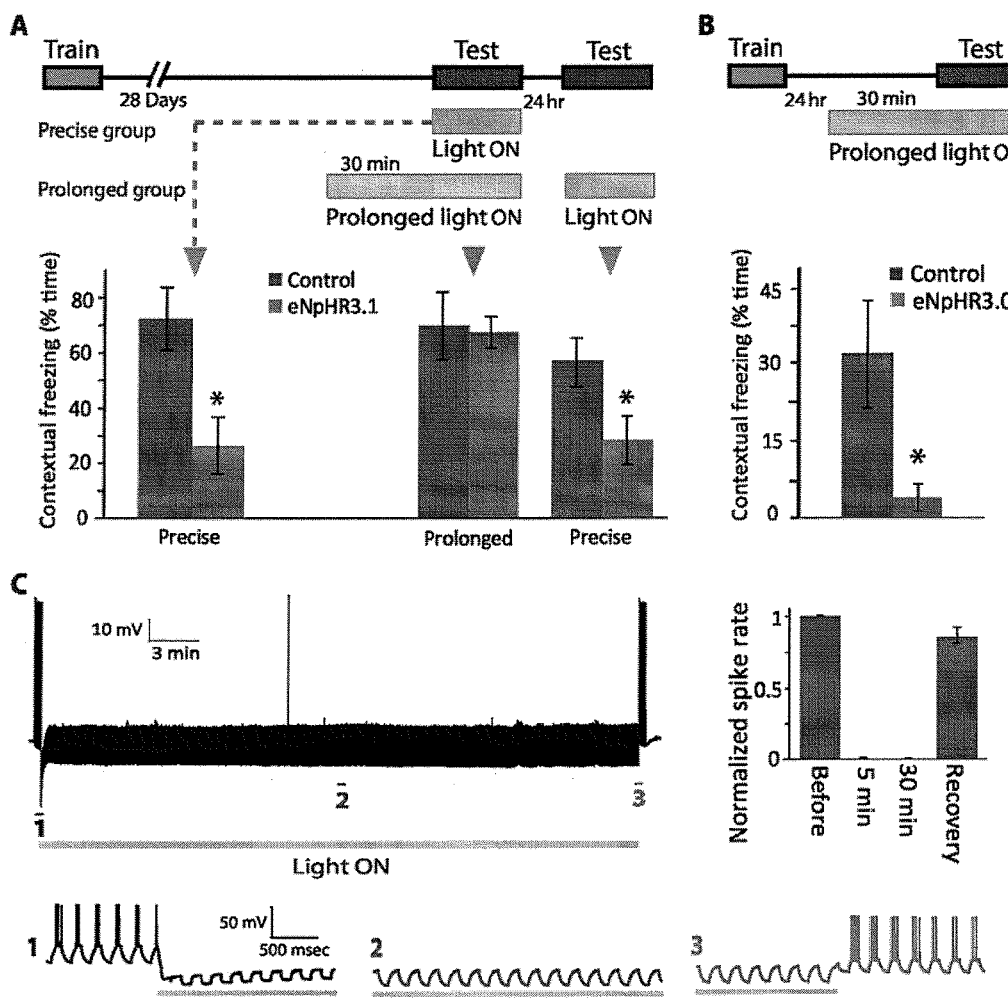
FIGS. 7A-7C depicts experimental data showing that precise, but not prolonged CA1 optogenetic inhibition blocks remote contextual fear recall.

To test the hypothesis that temporal precision is a critical factor accounting for the discrepancy between the optogenetic and pharmacological findings, the remote optogenetic experiment was repeated with either illumination limited to the duration of the test as before (FIG. 7A "precise"), or with prolonged illumination for 30 min before testing and during the test to mimic a slower intervention and allow time for putative compensatory mechanisms to be engaged (FIG. 7A "prolonged"). Precise optogenetic inhibition significantly inhibited remote memory, whereas prolonged inhibition had no detectable effect on remote memory retrieval (FIG. 7A). Furthermore, when mice from the prolonged group were re-tested on the next day with precise light administration (during the test only), the same mice displayed inhibited fear recall (FIG. 7A right). In other words, CA1 optogenetic inhibition prevents remote fear recall of a memory that was acquired 28 days earlier, only when the light was administered precisely during testing (Precise group, Control n=4, 72.65±11.5% freezing, eNpHR3.1 n=8, 26.9±10.4% freezing; P<0.01), but not when the light was ON continuously for 30 min before, as well as during, the test (Prolonged group, middle, Control n=3, 70.13±12.2% freezing, eNpHR3.1 n=4, 67.7±5.6% freezing; P>0.05). When the prolonged group mice were re-tested the next day with light during the test only, their recall was disrupted (Prolonged group, left, 55.5±18.5 vs. 27.6±8.6% freezing; P<0.05).

Figure 6:
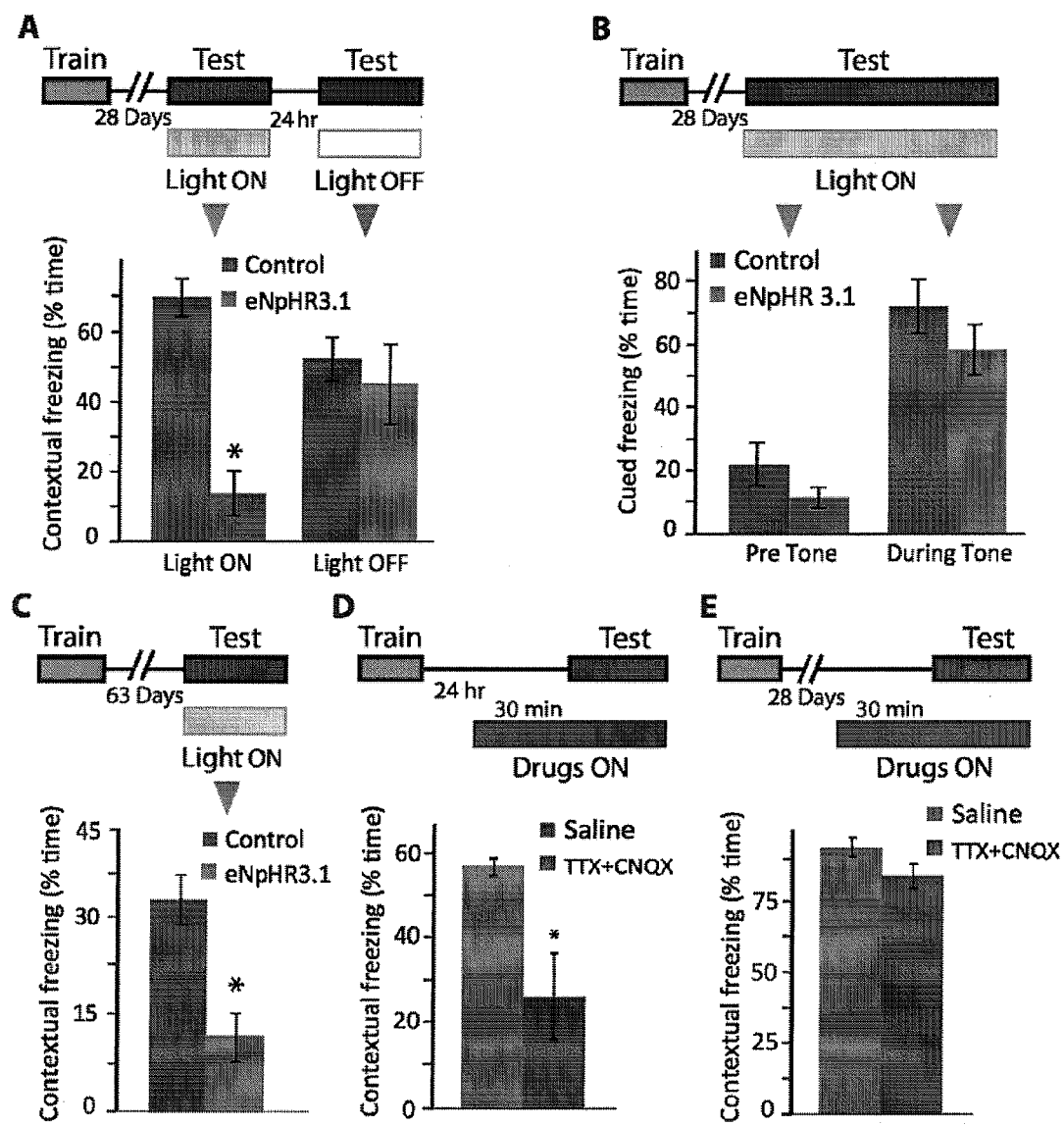
FIGS. 6A-6E depicts experimental data showing that CA1 optogenetic inhibition reversibly interferes with remote fear memory recall.

To validate these results, both behavioral and physiological controls were performed. First, it was confirmed that prolonged eNpHR3.1-mediated CA1 inhibition, which had no effect on remote memory, still could block recent memory. To that end, a new group of mice were trained and tested on the next day with prolonged illumination for 30 min before testing and then during the test. It was found that prolonged optogenetic inhibition significantly inhibited recent fear memory recall (FIG. 7B; Control n=7, 32.2±10.6% freezing, eNpHR3.1 n=3, 4±2.6% freezing; P<0.05), similar to the pharmacological effect (FIG. 6D). Second, whole-cell patch clamp recordings (in slices prepared from the prolonged group in FIG. 4A) was performed, which revealed that the ability of eNpHR3.1 to suppress spiking was stable throughout 30 min recording periods, as expected (Gradinaru et al., 2010), and was completely reversible (FIG. 7C). Detailed traces of sections 1 (inhibition onset) 2 (during continuous inhibition) and 3 (end of inhibition and recovery) are presented on the bottom left. Averaged percent successful evoked spiking before light, during light administration (after 5 min and 30 min of light ON) and recovery after light OFF are presented (bottom right; n=4 mice, 10 cells).

CA1 Optogenetic Inhibition Interferes with Ongoing Fear Recall.

Figure 8:
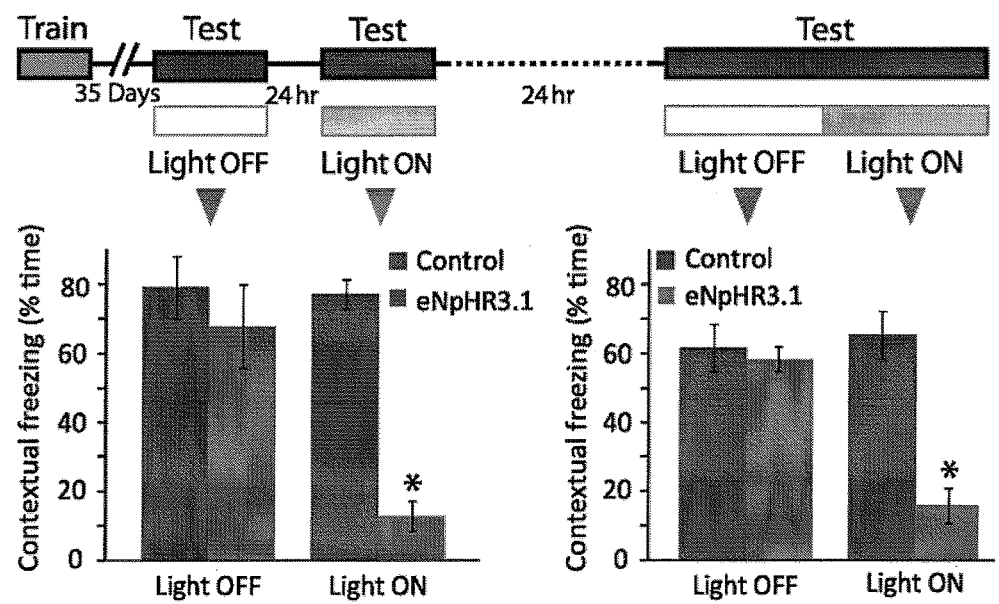
FIG. 8 depicts experimental data showing that CA1 optogenetic inhibition interferes with ongoing fear recall. Left: Remote fear memory that was acquired 5 weeks before and was efficiently recalled (Control n=8, 79.0±8.9% freezing; eNpHR3.1 n=6, 67.8±12.1% freezing; P>0.5) was no longer available for recall under CA1 optogenetic inhibition (77.2±4.3% vs. 12.8±4.4% freezing; P<0.0001). Right: This recall disruption did not result in memory erasure, as when the same mice were re-introduced to the conditioning context with no illumination they again demonstrated intact fear response (61.5±6.7 vs. 58.3±3.5% freezing; P>0.5). When illumination was introduced again in the middle of the testing trial, after the memory was already recalled, the fear response abruptly ceased (65.2±6.9 vs. 15.9±5.2% freezing; P<0.001).

Another population of mice were trained and the cohorts were tested 5 weeks after contextual FC with the remote light-on and light-off recall probe order reversed, first verifying persistence of the memory trace (without light during testing, observing similar performance in both eNpHR3.1 and control groups as expected; FIG. 8 left; control n=8, 79.0±8.9% freezing; eNpHR3.1 n=6, 67.8±12.1% freezing; P>0.5). On the next day, the same mice were tested under illumination, and the eNpHR3.1 group failed to recall the contextual memory (FIG. 8 left; 77.2±4.3% vs. 12.8±4.4% freezing; P<0.0001). This effect was in turn fully reversible, as on the next day, when tested without light delivery, eNpHR3.1 mice demonstrated intact contextual memory (FIG. 8 right; 61.5±6.7 vs. 58.3±3.5% freezing; P>0.5). Most importantly, as soon as the light was delivered again to CA1 within this session, after the mice had already recalled the aversive context and expressed fear, the fear response immediately ceased (FIG. 8 right, 65.2±6.9 vs. 15.9±5.2% freezing; P<0.001) in eNpHR3.1 but not control animals.

Together these data may unify certain disparate findings, at once supporting prior work by revealing that the remote memory trace is not stored only in the hippocampus (since when given enough time to compensate for hippocampal inactivation, the memory trace can still be retrieved by other structures, in line with previous reports), but at the same time revealing the surprising finding that the intact hippocampus may be a default activator of the remote memory trace and actively participates in its maintenance throughout the recall session.

Brain-Wide Mapping of Circuit Activity Controlled by Hippocampus During Remote Recall.

Figure 9:
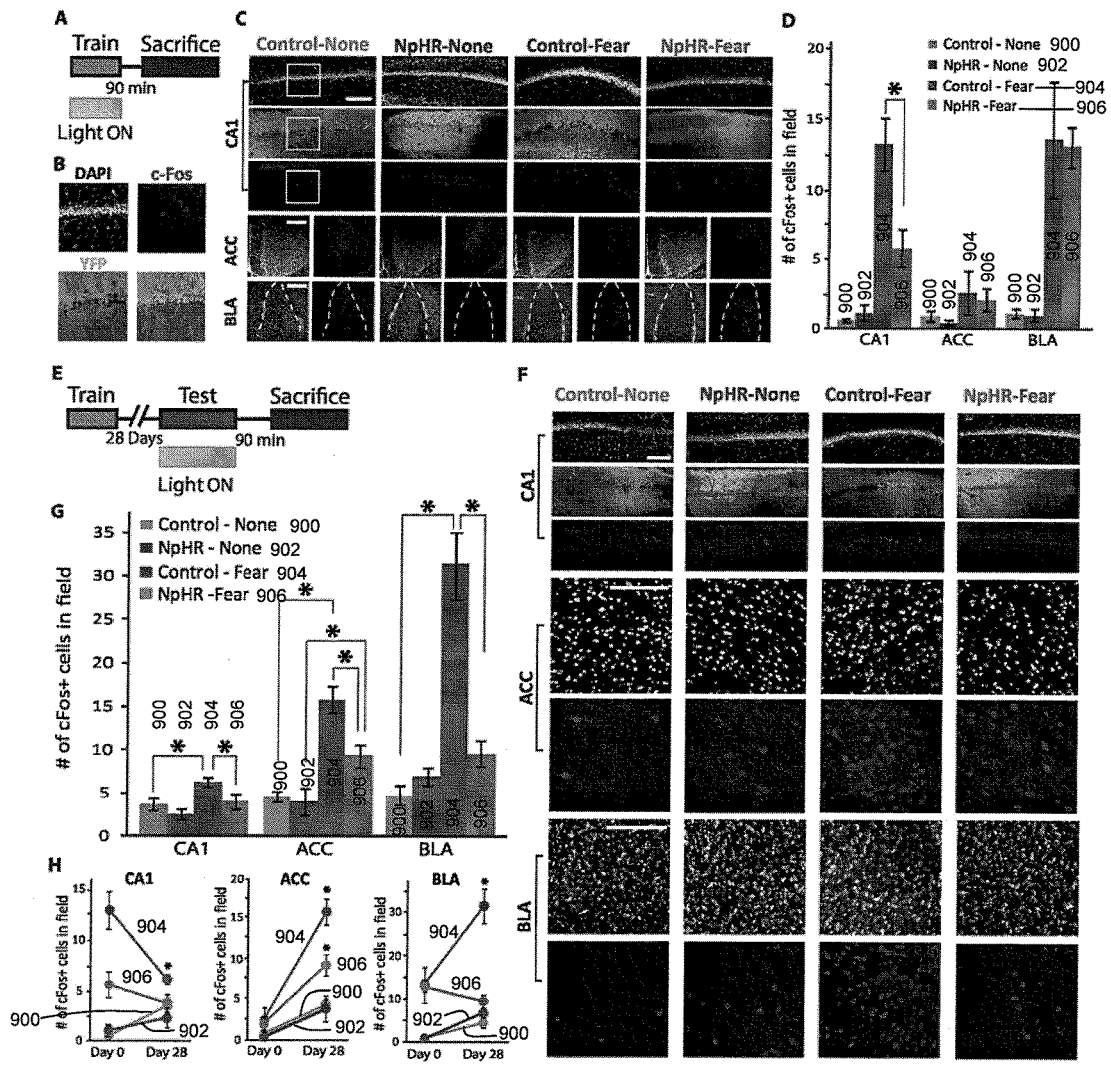
FIG. 9A-9H depicts experimental data showing brain-wide mapping of circuit activity controlled by the hippocampus during remote recall.

Previous studies of the expression of immediate-early gene products (e.g. zif268 and c-Fos), and other global measures of neural activity, have indicated that the transition from recent to remote memory can be accompanied by a decrease in hippocampal activity and an increase in neocortical activity (in ACC and prefrontal cortex; Bontempi et al., 1999; Frankland et al., 2004; Hall et al., 2001; Maviel et al., 2004). To extend this activity mapping approach to the setting of CA1 optogenetic control, eNpHR3.1-mediated inhibition was delivered during training or remote recall, and assessed induction of the immediate early gene product c-Fos across the entire brain. Mice were fear-conditioned under light delivery, and brains were collected 90 min after training (FIG. 9A). Brain slices were stained for c-Fos and DAPI (FIG. 9B). Expression of YFP control and eNpHR3.1 are shown. The CA1 region from which these images were taken is marked by a white square in FIG. 9C. Following training, eNpHR3.1-expressing mice demonstrated markedly reduced c-Fos expression specifically in CA1 compared with trained control animals (FIG. 9C-D; n=2 to 4 mice, 6 to 15 slices per group; $P<0.01$), but showed BLA activity equivalent to that of trained controls (FIG. 9C-D; $p<0.0001$) revealing the expected hippocampus-independent engagement of fear circuitry during training. Note that the bars and lines of FIGS. 9D, 9G, and 9H referenced by (900) are data of the "Control-None" group, (902) are data of the "NpHR-None" group, (904) are data of the "Control-Fear" group, and (906) are data of the "NpHR-Fear" group. No significant changes in ACC activity levels were observed at this time point. Representative images of CA1, ACC and BLA are shown. Anatomy is shown by DAPI nuclear staining, and the margins of the amygdala are marked with a dashed line. White scalebar: 150 μm.

Another group of mice was conditioned, and then re-exposed to the context 28 days after conditioning in the presence or absence of CA1 optogenetic inhibition; as before, the eNpHR3.1-expressing mice demonstrated impaired remote recall. 90 min later the brains were collected and stained for c-Fos (FIG. 9E) to capture putative memory-related brain-wide activity patterns under control of the hippocampus at this remote timepoint. Intriguingly, a small but significant increase in CA1 c-Fos was observed in control, but not eNpHR3.1 mice (FIG. 9F-G; $P<0.005$) following remote recall. Representative CA1, ACC and BLA images following remote memory are shown. White scalebar: 150 m. This population of CA1 cells appeared to be causally involved in recruiting brain-wide remote memory-related activity, as the increase in ACC activity ($P<0.0001$) at this remote timepoint observed in control animals was reduced in eNpHR3.1/CA1-inhibited mice ($P<0.0001$). Even more strikingly, activated cell populations in the BLA ($P<0.0001$) were observed in control mice (which recognized the context and expressed fear), but not in the CA1-inhibited eNpHR3.1 mice (which were moreover found to be unable to remember the context; FIG. 9F-G; $P<0.0001$). As depicted in FIG. 9G, remote recall 28 days following conditioning resulted in a small but significant increase in CA1 c-Fos expression in control mice, and highly increased activity levels in ACC and BLA. Light inhibition during exposure to the context completely blocked CA1 activity ($P<0.05$), and significantly reduced ACC and BLA activity, compared to control.

Additional observations point to the specificity of this CA1-recruited population at the remote timepoint. eNpHR3.1-expressing mice showed an elevation in prefrontal cortex activity equivalent to that of controls, and no significant changes in parietal cortex activity levels were observed in any of the groups. In contrast, as noted above, activity levels in the ACC were significantly recruited in remote memory only, and to a lesser extent in the setting of eNpHR3.1-mediated CA1 inhibition (FIG. 9H middle), also in agreement with previous reports (Bontempi et al., 1999; Frankland et al., 2004; Hall et al., 2001; Maviel et al., 2004). FIG. 9H depicts global patterns in brain activity between conditioning (day 0) and remote recall (day 28). Activity levels in CA1 significantly decreased in control ($P<0.005$) mice from day 0 to day 28. Activity levels in ACC significantly increased in both control ($P<0.0001$) and eNpHR3.1 ($P<0.001$) mice day 0 to day 28. Activity levels in BLA significantly increased in control ($P<0.001$) but not in eNHR3.1 mice. Together these data point to a role for this small population of CA1 neurons in organizing the brain-wide activity patterns associated with remote contextual memory.

Optogenetic Inhibition of ACC Inhibits Remote but not Recent Contextual Memory.

Figure 10:
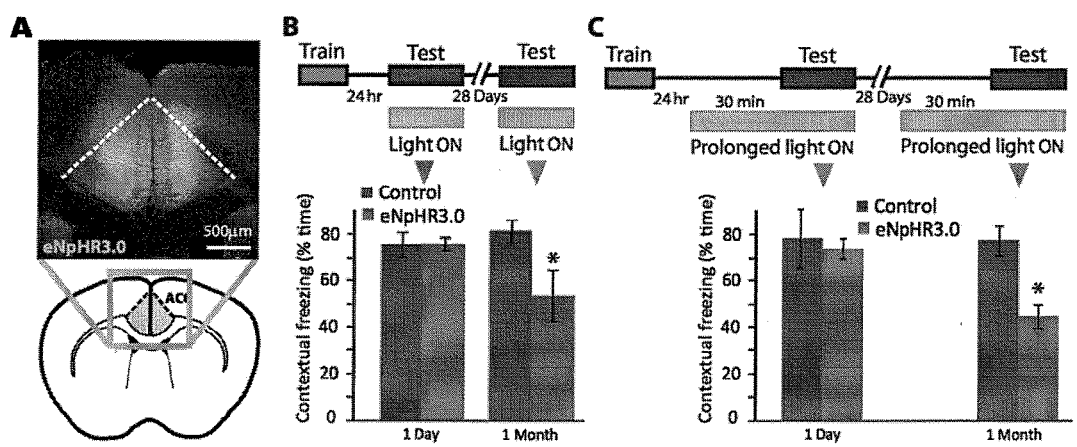
FIG. 10 depicts experimental data showing that precise and prolonged anterior cingulate cortex (ACC) optogenetic inhibition disrupts remote, but not recent, fear memory recall.

Since the population of CA1 neurons active during remote contextual memory was found to be causally involved in fully organizing ACC neuronal activity as shown above, and since previous research has implicated the ACC in remote fear memory storage (Bontempi et al., 1999; Fischer et al., 2007; Frankland et al., 2004; Maviel et al., 2004), optogenetic inhibition of memories was explored by targeting ACC directly either one day or one month following contextual FC. FIG. 10A depicts eNpHR3.0 expression in the anterior cingulate cortex (ACC). In full accordance with previous studies (Frankland et al., 2004), optogenetic inhibition of ACC had no effect on recent memory (75.9±5.4 vs. 76±2.9% freezing), but significantly impaired remote memory (FIG. 10B; Control n=5, 81.6±4.9% freezing; eNpHR3.0 n=5, 53.8±11% freezing; $P<0.05$).

The same experiment was repeated in a new group of mice, but this time delivered prolonged illumination for 30 min before testing and then during the test. Again it was found that optogenetic inhibition of ACC significantly impaired remote memory (Control n=3, 78.0±6.2% freezing; eNpHR3.0 n=8, 45.0±5.2% freezing; $P<0.05$), but had no effect on recent memory (FIG. 10C; 78.5±12.7 vs. 74.3±4.3% freezing). In contrast, when another major cortical input region was targeted for control purposes, the olfactory bulbs (OB), and the effect of optogenetic inhibition was tested during both recent and remote fear recall, it was found no effect on recall at either time point This result at once demonstrates that a sudden drop in a major source of synaptic input to cortex does not nonspecifically influence recall, and also points to the specificity of ACC in remote memory (consistent with prior work). Together, these findings support the remote importance of neocortex, and also illustrate that even following cortical reorganization, there exists a default requirement for the hippocampus in recalling remote memory traces.

Irreversible erasure of remote memories was recently demonstrated in the hippocampus and cortex by PKW administration (Migues et al; Pastalkova et al 2006; Shema et al 2009; Shema et al 2007) and in the amygdala by selective ablation of pre-tagged neurons (Han et al 2009). On the other hand, remote memory traces that were assumed to be lost due to neuronal damage became available for recall following environmental enrichment and chromatin modifications (Fischer et al 2007). Optogenetics, on the other hand, enables reversible recall prevention, without permanent memory erasure. The finding that the hippocampus is still the default activator of contextual fear memory recall may be due to the fact that many place cells (Moser et al 2008) in CA1 remap in response to fear conditioning (Moita et al 2004), and may contribute to a faster recognition of the context. Indeed, hippocampal lesions were repeatedly shown to induce retrograde amnesia for spatial memory (Broadbent et al 2006; Martin et al 2005).

When remote memories are retrieved they become available for reconsolidation, which renders them susceptible for disruption but may also strengthen the trace (Dudai 2006; Morris et al 2006; Nader and Hardt 2009; Tronson and Taylor 2007; Wang and Morris). The ability to reversibly shut down a remote fearful memory in real-time, before and after reconsolidation, and even in real-time after it had already been retrieved, may open an exciting therapeutic avenue for PTSD patients, in which a recurring disturbing memory may be stopped as it appears, without permanently affecting other memories. Additionally, memories related to drugs of abuse can be inhibited to reduce drug seeking behavior (Everitt et al 2001; Lee et al 2005; Robbins et al 2008). The ability to instantaneously affect cognition by optogenetic modulation of different brain areas may serve as a basis for future studies re-examining the role of specific neuronal populations in memory processes and enable a finer temporal, genetic and spatial dissection of the neuronal circuits that underlie them.

Although the foregoing invention has been described in some detail by way of illustration and example for purposes of clarity of understanding, the descriptions and examples should not be construed as limiting the scope of the invention.

REFERENCES

Adamantidis, A. R., Zhang, F., Aravanis, A. M., Deisseroth, K., and de Lecea, L. (2007). Neural substrates of awakening probed with optogenetic control of hypocretin neurons. Nature 450, 420-424.

Anagnostaras, S. G., Maren, S., and Fanselow, M. S. (1999). Temporally graded retrograde amnesia of contextual fear after hippocampal damage in rats: within-subjects examination. J Neurosci 19, 1106-1114.

Aravanis, A. M., Wang, L. P., Zhang, F., Meltzer, L. A., Mogri, M. Z., Schneider, M. B., and Deisseroth, K. (2007). An optical neural interface: in vivo control of rodent motor cortex with integrated fiberoptic and optogenetic technology. J Neural Eng 4, S143-156.

Bolhuis, J. J., Stewart, C. A., and Forrest, E. M. (1994). Retrograde amnesia and memory reactivation in rats with ibotenate lesions to the hippocampus or subiculum. Q J Exp Psychol B 47, 129-150.

Bontempi, B., Laurent-Demir, C., Destrade, C., and Jaffard, R. (1999). Time-dependent reorganization of brain circuitry underlying long-term memory storage. Nature 400, 671-675.

Boyden, E. S., Zhang, F., Bamberg, E., Nagel, G., and Deisseroth, K. (2005). Millisecond-timescale, genetically targeted optical control of neural activity. Nat Neurosci 8, 1263-1268.

Broadbent, N. J., Squire, L. R., and Clark, R. E. (2006). Reversible hippocampal lesions disrupt water maze performance during both recent and remote memory tests. Learn Mem 13, 187-191.

Cipolotti, L., and Bird, C. M. (2006). Amnesia and the hippocampus. Curr Opin Neurol 19, 593-598.

Debiec, J., LeDoux, J. E., and Nader, K. (2002). Cellular and systems reconsolidation in the hippocampus. Neuron 36, 527-538.

Deisseroth, K., Feng, G., Majewska, A. K., Miesenbock, G., Ting, A., and Schnitzer, M. J. (2006). Next-generation optical technologies for illuminating genetically targeted brain circuits. J Neurosci 26, 10380-10386.

Dudai, Y. (2006). Reconsolidation: the advantage of being refocused. Curr Opin Neurobiol 16, 174-178.

Everitt, B. J., Dickinson, A., and Robbins, T. W. (2001). The neuropsychological basis of addictive behaviour. Brain Res Brain Res Rev 36, 129-138.

Fanselow, M. S. (2000). Contextual fear, gestalt memories, and the hippocampus. Behav Brain Res 110, 73-81.

Fischer, A., Sananbenesi, F., Wang, X., Dobbin, M., and Tsai, L. H. (2007). Recovery of learning and memory is associated with chromatin remodelling. Nature 447, 178-182.

Frankland, P. W., and Bontempi, B. (2005). The organization of recent and remote memories. Nat Rev Neurosci 6,119-130.

Frankland, P. W., Bontempi, B., Talton, L. E., Kaczmarek, L., and Silva, A. J. (2004). The involvement of the anterior cingulate cortex in remote contextual fear memory. Science 304, 881-883.

Gradinaru, V., Thompson, K. R., Zhang, F., Mogri, M., Kay, K., Schneider, M. B., and Deisseroth, K. (2007). Targeting and readout strategies for fast optical neural control in vitro and in vivo. J Neurosci 27,14231-14238.

Gradinaru, V., Zhang, F., Ramakrishnan, C., Mattis, J., Prakash, R., Diester, I., Goshen, I., Thompson, K. R., and Deisseroth, K. (2010). Molecular and cellular approaches for diversifying and extending optogenetics. Cell 141, 154-165.

Hall, J., Thomas, K. L., and Everitt, B. J. (2001). Cellular imaging of zif268 expression in the hippocampus and amygdala during contextual and cued fear memory retrieval: selective activation of hippocampal CA1 neurons during the recall of contextual memories. J Neurosci 21, 2186-2193.

Han, J. H., Kushner, S. A., Yiu, A. P., Hsiang, H. L., Buch, T., Waisman, A., Bontempi, B., Neve, R. L., Frankland, P. W., and Josselyn, S. A. (2009). Selective erasure of a fear memory. Science 323, 1492-1496.

Johansen, J. P., Hamanaka, H., Monfils, M. H., Behnia, R., Deisseroth, K., Blair, H. T., and LeDoux, J. E. (2010). Optical activation of lateral amygdala pyramidal cells instructs associative fear learning. Proc Natl Acad Sci USA 107,12692-12697.

Killcross, S., Robbins, T. W., and Everitt, B. J. (1997). Different types of fear-conditioned behaviour mediated by separate nuclei within amygdala. Nature 388, 377-380.

Kim, J. J., and Fanselow, M. S. (1992). Modality-specific retrograde amnesia of fear. Science 256, 675-677.

Kitamura, T., Saitoh, Y., Takashima, N., Murayama, A., Niibori, Y., Ageta, H., Sekiguchi, M., Sugiyama, H., and Inokuchi, K. (2009). Adult neurogenesis modulates the hippocampus-dependent period of associative fear memory. Cell 139, 814-827.

LeDoux, J. E. (2000). Emotion circuits in the brain. Annu Rev Neurosci 23, 155-184.

Lee, J. L., Di Ciano, P., Thomas, K. L., and Everitt, B. J. (2005). Disrupting reconsolidation of drug memories reduces cocaine-seeking behavior. Neuron 47, 795-801.

Lee, J. L., Milton, A. L., and Everitt, B. J. (2006). Reconsolidation and extinction of conditioned fear: inhibition and potentiation. J Neurosci 26, 10051-10056.

Maren, S. (2001). Neurobiology of Pavlovian fear conditioning. Annu Rev Neurosci 24, 897-931.

Maren, S., Aharonov, G., and Fanselow, M. S. (1997). Neurotoxic lesions of the dorsal hippocampus and Pavlovian fear conditioning in rats. Behav Brain Res 88, 261-274.

Maren, S., and Quirk, G. J. (2004). Neuronal signalling of fear memory. Nat Rev Neurosci 5, 844-852.

Martin, S. J., de Hoz, L., and Morris, R. G. (2005). Retrograde amnesia: neither partial nor complete hippocampal lesions in rats result in preferential sparing of remote spatial memory, even after reminding. Neuropsychologia 43, 609-624.

Maviel, T., Durkin, T. P., Menzaghi, F., and Bontempi, B. (2004). Sites of neocortical reorganization critical for remote spatial memory. Science 305, 96-99.

McHugh, T. J., Jones, M. W., Quinn, J. J., Balthasar, N., Coppari, R., Elmquist, J. K., Lowell, B. B., Fanselow, M. S., Wilson, M. A., and Tonegawa, S. (2007). Dentate gyrus NMDA receptors mediate rapid pattern separation in the hippocampal network. Science 317, 94-99.

McHugh, T. J., and Tonegawa, S. (2007). Spatial exploration is required for the formation of contextual fear memory. Behav Neurosci 121, 335-339.

Moita, M. A., Rosis, S., Zhou, Y., LeDoux, J. E., and Blair, H. T. (2004). Putting fear in its place: remapping of hippocampal place cells during fear conditioning. J Neurosci 24, 7015-7023.

Morris, R. G., Inglis, J., Ainge, J. A., Olverman, H. J., Tulloch, J., Dudai, Y., and Kelly, P. A. (2006). Memory reconsolidation: sensitivity of spatial memory to inhibition of protein synthesis in dorsal hippocampus during encoding and retrieval. Neuron 50, 479-489.

Moscovitch, M., Nadel, L., Winocur, G., Gilboa, A., and Rosenbaum, R. S. (2006). The cognitive neuroscience of remote episodic, semantic and spatial memory. Curr Opin Neurobiol 16, 179-190.

Moser, E. I., Kropff, E., and Moser, M. B. (2008). Place cells, grid cells, and the brain's spatial representation system. Annu Rev Neurosci 31, 69-89.

Nadel, L., and Moscovitch, M. (1997). Memory consolidation, retrograde amnesia and the hippocampal complex. Curr Opin Neurobiol 7, 217-227.

Nader, K., and Hardt, O. (2009). A single standard for memory: the case for reconsolidation. Nat Rev Neurosci 10, 224-234.

Nakashiba, T., Young, J. Z., McHugh, T. J., Buhl, D. L., and Tonegawa, S. (2008). Transgenic inhibition of synaptic transmission reveals role of CA3 output in hippocampal learning. Science 319, 1260-1264.

Phelps, E. A., and LeDoux, J. E. (2005). Contributions of the amygdala to emotion processing: from animal models to human behavior. Neuron 48, 175-187.

Riedel, G., Micheau, J., Lam, A. G., Roloff, E. L., Martin, S. J., Bridge, H., de Hoz, L., Poeschel, B., McCulloch, J., and Morris, R. G. (1999). Reversible neural inactivation reveals hippocampal participation in several memory processes. Nat Neurosci 2, 898-905.

Robbins, T. W., Ersche, K. D., and Everitt, B. J. (2008). Drug addiction and the memory systems of the brain. Ann N Y Acad Sci 1141, 1-21.

Shimizu, E., Tang, Y. P., Rampon, C., and Tsien, J. Z. (2000). NMDA receptor-dependent synaptic reinforcement as a crucial process for memory consolidation. Science 290, 1170-1174.

Squire, L. R., and Alvarez, P. (1995). Retrograde amnesia and memory consolidation: a neurobiological perspective. Curr Opin Neurobiol 5, 169-177.

Squire, L. R., and Bayley, P. J. (2007). The neuroscience of remote memory. Curr Opin Neurobiol 17, 185-196.

Sutherland, R. J., O'Brien, J., and Lehmann, H. (2008). Absence of systems consolidation of fear memories after dorsal, ventral, or complete hippocampal damage. Hippocampus 18, 710-718.

Sutherland, R. J., Sparks, F. T., and Lehmann, H. (2010). Hippocampus and retrograde amnesia in the rat model: a modest proposal for the situation of systems consolidation. Neuropsychologia 48, 2357-2369.

Tronson, N. C., and Taylor, J. R. (2007). Molecular mechanisms of memory reconsolidation. Nat Rev Neurosci 8, 262-275.

Wang, H., Shimizu, E., Tang, Y. P., Cho, M., Kyin, M., Zuo, W., Robinson, D. A., Alaimo, P. J., Zhang, C., Morimoto, H., et al. (2003). Inducible protein knockout reveals temporal requirement of CaMKII reactivation for memory consolidation in the brain. Proc Natl Acad Sci USA 100, 4287-4292.

Wang, S. H., and Morris, R. G. (2010). Hippocampal-neocortical interactions in memory formation, consolidation, and reconsolidation. Annu Rev Psychol 61, 49-79, C41-44.

Wang, S. H., Teixeira, C. M., Wheeler, A. L., and Frankland, P. W. (2009). The precision of remote context memories does not require the hippocampus. Nat Neurosci 12, 253-255.

Wiltgen, B. J., Zhou, M., Cai, Y., Balaji, J., Karlsson, M. G., Parivash, S. N., Li, W., and Silva, A. J. (2010). The Hippocampus Plays a Selective Role in the Retrieval of Detailed Contextual Memories. Curr Biol 20, 1336-1344.

Winocur, G., Frankland, P. W., Sekeres, M., Fogel, S., and Moscovitch, M. (2009). Changes in context-specificity during memory reconsolidation: selective effects of hippocampal lesions. Learn Mem 16, 722-729.

Winocur, G., Moscovitch, M., and Bontempi, B. (2010). Memory formation and long-term retention in humans and animals: convergence towards a transformation account of hippocampal-neocortical interactions. Neuropsychologia 48, 2339-2356.

Winocur, G., Moscovitch, M., and Sekeres, M. (2007). Memory consolidation or transformation: context manipulation and hippocampal representations of memory. Nat Neurosci 10, 555-557.

Zhang, F., Wang, L. P., Brauner, M., Liewald, J. F., Kay, K., Watzke, N., Wood, P. G., Bamberg, E., Nagel, G., Gottschalk, A., et al. (2007). Multimodal fast optical interrogation of neural circuitry. Nature 446, 633-639.

What is claimed is:

1. A method for reversibly inhibiting the formation of a fearful memory associated with contextual fear conditioning or retrieval of a fearful memory associated with contextual fear conditioning in an individual, the method comprising:
   a) administering a recombinant viral expression vector comprising a nucleotide sequence encoding a light-activated protein directly to the dorsal CA1 field of the hippocampus, wherein the nucleotide sequence is operably linked to a neuron-specific promoter, wherein light-activated protein is expressed on the cell membrane of the excitatory neurons in the dorsal CA1 field of the hippocampus, wherein the light-activated protein is responsive to light and is capable of inhibiting depolarization of the neurons when the neurons are illuminated with the light, and wherein the light-activated protein comprises, in order from amino terminus to carboxyl terminus:
      i) a core amino acid sequence that is at least 85% identical to the NpHR amino acid sequence set forth in SEQ ID NO:3;
      ii) an endoplasmic reticulum (ER) export signal; and
      iii) a membrane trafficking signal; and
   b) activating the light-activated protein by light using an implantable light source implanted adjacent to the neurons expressing the light-activated protein, whereby activating the protein by the light reversibly inhibits formation or retrieval of the fearful memory in the individual.

2. The method of claim 1, wherein the recombinant viral expression vector is selected from the group consisting of an adenoassociated virus vector, a retroviral vector, an adenoviral vector, a herpes simplex virus vector, and a lentiviral vector.

3. The method of claim 1, wherein the individual is a human.

4. The method of claim 1, wherein the individual is a non-human mammal.

5. The method of claim 1, wherein the core amino acid sequence is at least 90% identical to the NpHR amino acid sequence set forth in SEQ ID NO:3.

6. The method of claim 1, wherein core the amino acid sequence is linked to the ER export signal and the membrane trafficking signal through a linker.

7. The method of claim 1, wherein the ER export signal comprises the amino acid sequence FCYENEV (SEQ ID NO:9).

8. The method of claim 1, wherein the membrane trafficking signal comprise the amino acid sequence KSRITSEGEYIPLDQIDINV (SEQ ID NO:10).

9. The method of claim 1, wherein the neuron-specific promoter is a CaMKII promoter.

* * * * *

UNITED STATES PATENT AND TRADEMARK OFFICE
CERTIFICATE OF CORRECTION

PATENT NO.       : 10,086,012 B2
APPLICATION NO.  : 13/882705
DATED            : October 2, 2018
INVENTOR(S)      : Deisseroth et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 188 days.

Signed and Sealed this
Eighteenth Day of June, 2019

Andrei Iancu
*Director of the United States Patent and Trademark Office*

SEQUENCE LISTING

<160> NUMBER OF SEQ ID NOS: 10

<210> SEQ ID NO 1
<211> LENGTH: 223
<212> TYPE: PRT
<213> ORGANISM: Guillardia theta

<400> SEQUENCE: 1

Ala Ser Ser Phe Gly Lys Ala Leu Leu Glu Phe Val Phe Ile Val Phe
1               5                   10                  15

Ala Cys Ile Thr Leu Leu Leu Gly Ile Asn Ala Ala Lys Ser Lys Ala

```
            20                  25                  30
Ala Ser Arg Val Leu Phe Pro Ala Thr Phe Val Thr Gly Ile Ala Ser
        35                  40                  45

Ile Ala Tyr Phe Ser Met Ala Ser Gly Gly Gly Trp Val Ile Ala Pro
 50                  55                  60

Asp Cys Arg Gln Leu Phe Val Ala Arg Tyr Leu Asp Trp Leu Ile Thr
 65                  70                  75                  80

Thr Pro Leu Leu Leu Ile Asp Leu Gly Leu Val Ala Gly Val Ser Arg
                 85                  90                  95

Trp Asp Ile Met Ala Leu Cys Leu Ser Asp Val Leu Met Ile Ala Thr
                100                 105                 110

Gly Ala Phe Gly Ser Leu Thr Val Gly Asn Val Lys Trp Val Trp Trp
                115                 120                 125

Phe Phe Gly Met Cys Trp Phe Leu His Ile Ile Phe Ala Leu Gly Lys
                130                 135                 140

Ser Trp Ala Glu Ala Ala Lys Ala Lys Gly Gly Asp Ser Ala Ser Val
145                 150                 155                 160

Tyr Ser Lys Ile Ala Gly Ile Thr Val Ile Thr Trp Phe Cys Tyr Pro
                165                 170                 175

Val Val Trp Val Phe Ala Glu Gly Phe Gly Asn Phe Ser Val Thr Phe
                180                 185                 190

Glu Val Leu Ile Tyr Gly Val Leu Asp Val Ile Ser Lys Ala Val Phe
                195                 200                 205

Gly Leu Ile Leu Met Ser Gly Ala Ala Thr Gly Tyr Glu Ser Ile
                210                 215                 220

<210> SEQ ID NO 2
<211> LENGTH: 270
<212> TYPE: PRT
<213> ORGANISM: Artificial Sequence
<220> FEATURE:
<223> OTHER INFORMATION: Synthetic peptide

<400> SEQUENCE: 2

Met Asp Tyr Gly Gly Ala Leu Ser Ala Val Gly Arg Glu Leu Leu Phe
 1                   5                  10                  15

Val Thr Asn Pro Val Val Asn Gly Ser Val Leu Val Pro Glu Asp
                 20                  25                  30

Gln Cys Tyr Cys Ala Gly Trp Ile Glu Ser Arg Gly Thr Asn Gly Ala
                 35                  40                  45

Ser Ser Phe Gly Lys Ala Leu Leu Glu Phe Val Phe Ile Val Phe Ala
 50                  55                  60

Cys Ile Thr Leu Leu Leu Gly Ile Asn Ala Ala Lys Ser Lys Ala Ala
 65                  70                  75                  80

Ser Arg Val Leu Phe Pro Ala Thr Phe Val Thr Gly Ile Ala Ser Ile
                 85                  90                  95

Ala Tyr Phe Ser Met Ala Ser Gly Gly Gly Trp Val Ile Ala Pro Asp
                100                 105                 110

Cys Arg Gln Leu Phe Val Ala Arg Tyr Leu Asp Trp Leu Ile Thr Thr
                115                 120                 125

Pro Leu Leu Leu Ile Asp Leu Gly Leu Val Ala Gly Val Ser Arg Trp
                130                 135                 140

Asp Ile Met Ala Leu Cys Leu Ser Asp Val Leu Met Ile Ala Thr Gly
145                 150                 155                 160

Ala Phe Gly Ser Leu Thr Val Gly Asn Val Lys Trp Val Trp Trp Phe
```

```
                         165                 170                 175
Phe Gly Met Cys Trp Phe Leu His Ile Ile Phe Ala Leu Gly Lys Ser
            180                 185                 190

Trp Ala Glu Ala Ala Lys Ala Lys Gly Gly Asp Ser Ala Ser Val Tyr
            195                 200                 205

Ser Lys Ile Ala Gly Ile Thr Val Ile Thr Trp Phe Cys Tyr Pro Val
            210                 215                 220

Val Trp Val Phe Ala Glu Gly Phe Gly Asn Phe Ser Val Thr Phe Glu
225                 230                 235                 240

Val Leu Ile Tyr Gly Val Leu Asp Val Ile Ser Lys Ala Val Phe Gly
                245                 250                 255

Leu Ile Leu Met Ser Gly Ala Ala Thr Gly Tyr Glu Ser Ile
            260                 265                 270

<210> SEQ ID NO 3
<211> LENGTH: 273
<212> TYPE: PRT
<213> ORGANISM: Natronomonas pharaonis

<400> SEQUENCE: 3

Val Thr Gln Arg Glu Leu Phe Glu Phe Val Leu Asn Asp Pro Leu Leu
1               5                   10                  15

Ala Ser Ser Leu Tyr Ile Asn Ile Ala Leu Ala Gly Leu Ser Ile Leu
            20                  25                  30

Leu Phe Val Phe Met Thr Arg Gly Leu Asp Asp Pro Arg Ala Lys Leu
            35                  40                  45

Ile Ala Val Ser Thr Ile Leu Val Pro Val Val Ser Ile Ala Ser Tyr
        50                  55                  60

Thr Gly Leu Ala Ser Gly Leu Thr Ile Ser Val Leu Glu Met Pro Ala
65              70                  75                  80

Gly His Phe Ala Glu Gly Ser Ser Val Met Leu Gly Gly Glu Glu Val
            85                  90                  95

Asp Gly Val Val Thr Met Trp Gly Arg Tyr Leu Thr Trp Ala Leu Ser
            100                 105                 110

Thr Pro Met Ile Leu Leu Ala Leu Gly Leu Leu Ala Gly Ser Asn Ala
            115                 120                 125

Thr Lys Leu Phe Thr Ala Ile Thr Phe Asp Ile Ala Met Cys Val Thr
            130                 135                 140

Gly Leu Ala Ala Ala Leu Thr Thr Ser Ser His Leu Met Arg Trp Phe
145                 150                 155                 160

Trp Tyr Ala Ile Ser Cys Ala Cys Phe Leu Val Val Leu Tyr Ile Leu
                165                 170                 175

Leu Val Glu Trp Ala Gln Asp Ala Lys Ala Ala Gly Thr Ala Asp Met
            180                 185                 190

Phe Asn Thr Leu Lys Leu Leu Thr Val Val Met Trp Leu Gly Tyr Pro
            195                 200                 205

Ile Val Trp Ala Leu Gly Val Glu Gly Ile Ala Val Leu Pro Val Gly
            210                 215                 220

Val Thr Ser Trp Gly Tyr Ser Phe Leu Asp Ile Val Ala Lys Tyr Ile
225                 230                 235                 240

Phe Ala Phe Leu Leu Leu Asn Tyr Leu Thr Ser Asn Glu Ser Val Val
                245                 250                 255

Ser Gly Ser Ile Leu Asp Val Pro Ser Ala Ser Gly Thr Pro Ala Asp
            260                 265                 270
```

Asp

<210> SEQ ID NO 4
<211> LENGTH: 291
<212> TYPE: PRT
<213> ORGANISM: Artificial Sequence
<220> FEATURE:
<223> OTHER INFORMATION: Synthetic peptide

<400> SEQUENCE: 4

```
Met Thr Glu Thr Leu Pro Pro Val Thr Glu Ser Ala Val Ala Leu Gln
1               5                   10                  15

Ala Glu Val Thr Gln Arg Glu Leu Phe Glu Phe Val Leu Asn Asp Pro
                20                  25                  30

Leu Leu Ala Ser Ser Leu Tyr Ile Asn Ile Ala Leu Ala Gly Leu Ser
            35                  40                  45

Ile Leu Leu Phe Val Phe Met Thr Arg Gly Leu Asp Asp Pro Arg Ala
50                  55                  60

Lys Leu Ile Ala Val Ser Thr Ile Leu Val Pro Val Val Ser Ile Ala
65                  70                  75                  80

Ser Tyr Thr Gly Leu Ala Ser Gly Leu Thr Ile Ser Val Leu Glu Met
                85                  90                  95

Pro Ala Gly His Phe Ala Glu Gly Ser Ser Val Met Leu Gly Gly Glu
            100                 105                 110

Glu Val Asp Gly Val Val Thr Met Trp Gly Arg Tyr Leu Thr Trp Ala
        115                 120                 125

Leu Ser Thr Pro Met Ile Leu Leu Ala Leu Gly Leu Leu Ala Gly Ser
130                 135                 140

Asn Ala Thr Lys Leu Phe Thr Ala Ile Thr Phe Asp Ile Ala Met Cys
145                 150                 155                 160

Val Thr Gly Leu Ala Ala Ala Leu Thr Thr Ser Ser His Leu Met Arg
                165                 170                 175

Trp Phe Trp Tyr Ala Ile Ser Cys Ala Cys Phe Leu Val Val Leu Tyr
            180                 185                 190

Ile Leu Leu Val Glu Trp Ala Gln Asp Ala Lys Ala Ala Gly Thr Ala
        195                 200                 205

Asp Met Phe Asn Thr Leu Lys Leu Leu Thr Val Val Met Trp Leu Gly
210                 215                 220

Tyr Pro Ile Val Trp Ala Leu Gly Val Glu Gly Ile Ala Val Leu Pro
225                 230                 235                 240

Val Gly Val Thr Ser Trp Gly Tyr Ser Phe Leu Asp Ile Val Ala Lys
                245                 250                 255

Tyr Ile Phe Ala Phe Leu Leu Leu Asn Tyr Leu Thr Ser Asn Glu Ser
            260                 265                 270

Val Val Ser Gly Ser Ile Leu Asp Val Pro Ser Ala Ser Gly Thr Pro
        275                 280                 285

Ala Asp Asp
        290
```

<210> SEQ ID NO 5
<211> LENGTH: 559
<212> TYPE: PRT
<213> ORGANISM: Artificial Sequence
<220> FEATURE:
<223> OTHER INFORMATION: Synthetic peptide

<400> SEQUENCE: 5

-continued

```
Met Thr Glu Thr Leu Pro Pro Val Thr Glu Ser Ala Val Ala Leu Gln
 1               5                  10                  15

Ala Glu Val Thr Gln Arg Glu Leu Phe Glu Phe Val Leu Asn Asp Pro
            20                  25                  30

Leu Leu Ala Ser Ser Leu Tyr Ile Asn Ile Ala Leu Ala Gly Leu Ser
        35                  40                  45

Ile Leu Leu Phe Val Phe Met Thr Arg Gly Leu Asp Asp Pro Arg Ala
 50                  55                  60

Lys Leu Ile Ala Val Ser Thr Ile Leu Val Pro Val Ser Ile Ala
 65                  70                  75                  80

Ser Tyr Thr Gly Leu Ala Ser Gly Leu Thr Ile Ser Val Leu Glu Met
                85                  90                  95

Pro Ala Gly His Phe Ala Glu Gly Ser Ser Val Met Leu Gly Gly Glu
            100                 105                 110

Glu Val Asp Gly Val Val Thr Met Trp Gly Arg Tyr Leu Thr Trp Ala
            115                 120                 125

Leu Ser Thr Pro Met Ile Leu Leu Ala Leu Gly Leu Leu Ala Gly Ser
        130                 135                 140

Asn Ala Thr Lys Leu Phe Thr Ala Ile Thr Phe Asp Ile Ala Met Cys
145                 150                 155                 160

Val Thr Gly Leu Ala Ala Ala Leu Thr Thr Ser Ser His Leu Met Arg
                165                 170                 175

Trp Phe Trp Tyr Ala Ile Ser Cys Ala Cys Phe Leu Val Val Leu Tyr
            180                 185                 190

Ile Leu Leu Val Glu Trp Ala Gln Asp Ala Lys Ala Ala Gly Thr Ala
        195                 200                 205

Asp Met Phe Asn Thr Leu Lys Leu Leu Thr Val Val Met Trp Leu Gly
        210                 215                 220

Tyr Pro Ile Val Trp Ala Leu Gly Val Glu Gly Ile Ala Val Leu Pro
225                 230                 235                 240

Val Gly Val Thr Ser Trp Gly Tyr Ser Phe Leu Asp Ile Val Ala Lys
                245                 250                 255

Tyr Ile Phe Ala Phe Leu Leu Leu Asn Tyr Leu Thr Ser Asn Glu Ser
            260                 265                 270

Val Val Ser Gly Ser Ile Leu Asp Val Pro Ser Ala Ser Gly Thr Pro
        275                 280                 285

Ala Asp Asp Ala Ala Ala Lys Ser Arg Ile Thr Ser Glu Gly Glu Tyr
        290                 295                 300

Ile Pro Leu Asp Gln Ile Asp Ile Asn Val Val Ser Lys Gly Glu Glu
305                 310                 315                 320

Leu Phe Thr Gly Val Val Pro Ile Leu Val Glu Leu Asp Gly Asp Val
                325                 330                 335

Asn Gly His Lys Phe Ser Val Ser Gly Glu Gly Glu Gly Asp Ala Thr
            340                 345                 350

Tyr Gly Lys Leu Thr Leu Lys Phe Ile Cys Thr Thr Gly Lys Leu Pro
        355                 360                 365

Val Pro Trp Pro Thr Leu Val Thr Thr Phe Gly Tyr Gly Leu Gln Cys
        370                 375                 380

Phe Ala Arg Tyr Pro Asp His Met Lys Gln His Asp Phe Phe Lys Ser
385                 390                 395                 400

Ala Met Pro Glu Gly Tyr Val Gln Glu Arg Thr Ile Phe Phe Lys Asp
                405                 410                 415

Asp Gly Asn Tyr Lys Thr Arg Ala Glu Val Lys Phe Glu Gly Asp Thr
```

```
                420             425             430
Leu Val Asn Arg Ile Glu Leu Lys Gly Ile Asp Phe Lys Glu Asp Gly
            435                 440                 445
Asn Ile Leu Gly His Lys Leu Glu Tyr Asn Tyr Asn Ser His Asn Val
        450                 455                 460
Tyr Ile Met Ala Asp Lys Gln Lys Asn Gly Ile Lys Val Asn Phe Lys
465                 470                 475                 480
Ile Arg His Asn Ile Glu Asp Gly Ser Val Gln Leu Ala Asp His Tyr
                485                 490                 495
Gln Gln Asn Thr Pro Ile Gly Asp Gly Pro Val Leu Leu Pro Asp Asn
            500                 505                 510
His Tyr Leu Ser Tyr Gln Ser Ala Leu Ser Lys Asp Pro Asn Glu Lys
        515                 520                 525
Arg Asp His Met Val Leu Leu Glu Phe Val Thr Ala Ala Gly Ile Thr
    530                 535                 540
Leu Gly Met Asp Glu Leu Tyr Lys Phe Cys Tyr Glu Asn Glu Val
545                 550                 555

<210> SEQ ID NO 6
<211> LENGTH: 542
<212> TYPE: PRT
<213> ORGANISM: Artificial Sequence
<220> FEATURE:
<223> OTHER INFORMATION: Synthetic peptide

<400> SEQUENCE: 6

Met Val Thr Gln Arg Glu Leu Phe Glu Phe Val Leu Asn Asp Pro Leu
1               5                   10                  15
Leu Ala Ser Ser Leu Tyr Ile Asn Ile Ala Leu Ala Gly Leu Ser Ile
            20                  25                  30
Leu Leu Phe Val Phe Met Thr Arg Gly Leu Asp Asp Pro Arg Ala Lys
        35                  40                  45
Leu Ile Ala Val Ser Thr Ile Leu Val Pro Val Ser Ile Ala Ser
    50                  55                  60
Tyr Thr Gly Leu Ala Ser Gly Leu Thr Ile Ser Val Leu Glu Met Pro
65                  70                  75                  80
Ala Gly His Phe Ala Glu Gly Ser Ser Val Met Leu Gly Gly Glu Glu
                85                  90                  95
Val Asp Gly Val Val Thr Met Trp Gly Arg Tyr Leu Thr Trp Ala Leu
            100                 105                 110
Ser Thr Pro Met Ile Leu Leu Ala Leu Gly Leu Leu Ala Gly Ser Asn
        115                 120                 125
Ala Thr Lys Leu Phe Thr Ala Ile Thr Phe Asp Ile Ala Met Cys Val
    130                 135                 140
Thr Gly Leu Ala Ala Ala Leu Thr Thr Ser Ser His Leu Met Arg Trp
145                 150                 155                 160
Phe Trp Tyr Ala Ile Ser Cys Ala Cys Phe Leu Val Val Leu Tyr Ile
                165                 170                 175
Leu Leu Val Glu Trp Ala Gln Asp Ala Lys Ala Ala Gly Thr Ala Asp
            180                 185                 190
Met Phe Asn Thr Leu Lys Leu Leu Thr Val Val Met Trp Leu Gly Tyr
        195                 200                 205
Pro Ile Val Trp Ala Leu Gly Val Glu Gly Ile Ala Val Leu Pro Val
    210                 215                 220
Gly Val Thr Ser Trp Gly Tyr Ser Phe Leu Asp Ile Val Ala Lys Tyr
```

```
                225                 230                 235                 240
Ile Phe Ala Phe Leu Leu Asn Tyr Leu Thr Ser Asn Glu Ser Val
                    245                 250                 255

Val Ser Gly Ser Ile Leu Asp Val Pro Ser Ala Ser Gly Thr Pro Ala
                260                 265                 270

Asp Asp Ala Ala Ala Lys Ser Arg Ile Thr Ser Glu Gly Glu Tyr Ile
                275                 280                 285

Pro Leu Asp Gln Ile Asp Ile Asn Val Val Ser Lys Gly Glu Leu
            290                 295                 300

Phe Thr Gly Val Val Pro Ile Leu Val Glu Leu Asp Gly Asp Val Asn
305                 310                 315                 320

Gly His Lys Phe Ser Val Ser Gly Glu Gly Glu Gly Asp Ala Thr Tyr
                        325                 330                 335

Gly Lys Leu Thr Leu Lys Phe Ile Cys Thr Thr Gly Lys Leu Pro Val
                    340                 345                 350

Pro Trp Pro Thr Leu Val Thr Thr Phe Gly Tyr Gly Leu Gln Cys Phe
                355                 360                 365

Ala Arg Tyr Pro Asp His Met Lys Gln His Asp Phe Phe Lys Ser Ala
370                 375                 380

Met Pro Glu Gly Tyr Val Gln Glu Arg Thr Ile Phe Phe Lys Asp Asp
385                 390                 395                 400

Gly Asn Tyr Lys Thr Arg Ala Glu Val Lys Phe Glu Gly Asp Thr Leu
                    405                 410                 415

Val Asn Arg Ile Glu Leu Lys Gly Ile Asp Phe Lys Glu Asp Gly Asn
                420                 425                 430

Ile Leu Gly His Lys Leu Glu Tyr Asn Tyr Asn Ser His Asn Val Tyr
                435                 440                 445

Ile Met Ala Asp Lys Gln Lys Asn Gly Ile Lys Val Asn Phe Lys Ile
            450                 455                 460

Arg His Asn Ile Glu Asp Gly Ser Val Gln Leu Ala Asp His Tyr Gln
465                 470                 475                 480

Gln Asn Thr Pro Ile Gly Asp Gly Pro Val Leu Leu Pro Asp Asn His
                    485                 490                 495

Tyr Leu Ser Tyr Gln Ser Ala Leu Ser Lys Asp Pro Asn Glu Lys Arg
                500                 505                 510

Asp His Met Val Leu Leu Glu Phe Val Thr Ala Ala Gly Ile Thr Leu
            515                 520                 525

Gly Met Asp Glu Leu Tyr Lys Phe Cys Tyr Glu Asn Glu Val
530                 535                 540

<210> SEQ ID NO 7
<211> LENGTH: 262
<212> TYPE: PRT
<213> ORGANISM: Halobacterium helobium

<400> SEQUENCE: 7

Met Leu Glu Leu Leu Pro Thr Ala Val Glu Gly Val Ser Gln Ala Gln
1               5                   10                  15

Ile Thr Gly Arg Pro Glu Trp Ile Trp Leu Ala Leu Gly Thr Ala Leu
                20                  25                  30

Met Gly Leu Gly Thr Leu Tyr Phe Leu Val Lys Gly Met Gly Val Ser
            35                  40                  45

Asp Pro Asp Ala Lys Lys Phe Tyr Ala Ile Thr Thr Leu Val Pro Ala
50                  55                  60
```

```
Ile Ala Phe Thr Met Tyr Leu Ser Met Leu Leu Gly Tyr Gly Leu Thr
 65                  70                  75                  80

Met Val Pro Phe Gly Gly Glu Gln Asn Pro Ile Tyr Trp Ala Arg Tyr
                 85                  90                  95

Ala Asp Trp Leu Phe Thr Thr Pro Leu Leu Leu Asp Leu Ala Leu
            100                 105                 110

Leu Val Asp Ala Asp Gln Gly Thr Ile Leu Ala Leu Val Gly Ala Asp
        115                 120                 125

Gly Ile Met Ile Gly Thr Gly Leu Val Gly Ala Leu Thr Lys Val Tyr
    130                 135                 140

Ser Tyr Arg Phe Val Trp Trp Ala Ile Ser Thr Ala Ala Met Leu Tyr
145                 150                 155                 160

Ile Leu Tyr Val Leu Phe Phe Gly Phe Thr Ser Lys Ala Glu Ser Met
                165                 170                 175

Arg Pro Glu Val Ala Ser Thr Phe Lys Val Leu Arg Asn Val Thr Val
            180                 185                 190

Val Leu Trp Ser Ala Tyr Pro Val Val Trp Leu Ile Gly Ser Glu Gly
        195                 200                 205

Ala Gly Ile Val Pro Leu Asn Ile Glu Thr Leu Leu Phe Met Val Leu
    210                 215                 220

Asp Val Ser Ala Lys Val Gly Phe Gly Leu Ile Leu Leu Arg Ser Arg
225                 230                 235                 240

Ala Ile Phe Gly Glu Ala Glu Ala Pro Glu Pro Ser Ala Gly Asp Gly
                245                 250                 255

Ala Ala Ala Thr Ser Asp
            260

<210> SEQ ID NO 8
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (2)..(2)
<223> OTHER INFORMATION: xaa = any amino acid

<400> SEQUENCE: 8

Phe Xaa Tyr Glu Asn Glu
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 9

Phe Cys Tyr Glu Asn Glu Val
1               5

<210> SEQ ID NO 10
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 10
```

-continued

```
Lys Ser Arg Ile Thr Ser Glu Gly Glu Tyr Ile Pro Leu Asp Gln Ile
1               5                   10                  15

Asp Ile Asn Val
            20
```